(12) United States Patent
Zhang et al.

(10) Patent No.: US 11,116,817 B2
(45) Date of Patent: Sep. 14, 2021

(54) ANTIMICROBIAL AGENTS AND COMPOSITIONS COMPRISING THE SAME

(71) Applicants: Shuping Zhang, Columbia, MO (US); Ming Yang, Columbia, MO (US)

(72) Inventors: Shuping Zhang, Columbia, MO (US); Ming Yang, Columbia, MO (US)

(73) Assignee: THE CURATORS OF THE UNIVERSITY OF MISSOURI, Columbia, MO (US)

( * ) Notice: Subject to any disclaimer, the term of this patent is extended or adjusted under 35 U.S.C. 154(b) by 0 days.

(21) Appl. No.: 16/486,243

(22) PCT Filed: Feb. 16, 2018

(86) PCT No.: PCT/US2018/000053
§ 371 (c)(1),
(2) Date: Aug. 15, 2019

(87) PCT Pub. No.: WO2018/151839
PCT Pub. Date: Aug. 23, 2018

(65) Prior Publication Data
US 2019/0365850 A1 Dec. 5, 2019

Related U.S. Application Data

(60) Provisional application No. 62/460,398, filed on Feb. 17, 2017.

(51) Int. Cl.
| *A61K 38/17* | (2006.01) |
| *A61K 38/08* | (2019.01) |
| *A61K 38/10* | (2006.01) |
| *A61K 38/16* | (2006.01) |
| *C07K 7/06* | (2006.01) |
| *C07K 7/08* | (2006.01) |
| *C07K 14/00* | (2006.01) |

(52) U.S. Cl.
CPC ................ *A61K 38/1703* (2013.01)

(58) Field of Classification Search
CPC .... A61K 38/1703; A61K 38/17; A61K 38/08; A61K 38/10; A61K 38/16; C07K 14/465; C07K 7/06; C07K 7/08; C07K 14/00
USPC .......... 530/300, 324, 326, 327; 514/1.1, 2.4, 514/2.3, 2.8, 21.3, 21.6, 21.4
See application file for complete search history.

(56) References Cited

U.S. PATENT DOCUMENTS

| 4,966,848 | A | * | 10/1990 | Smith | .............. | C12N 9/1029 |
| | | | | | | 435/193 |
| 5,223,421 | A | * | 6/1993 | Smith | .............. | C12N 9/1029 |
| | | | | | | 435/193 |
| 5,242,902 | A | | 9/1993 | Murphy et al. | | |
| 5,635,594 | A | | 6/1997 | Lehrer et al. | | |
| 5,837,218 | A | * | 11/1998 | Peers | .............. | A61K 51/088 |
| | | | | | | 424/1.69 |
| 6,545,140 | B1 | | 4/2003 | Harmon et al. | | |
| 6,703,491 | B1 | * | 3/2004 | Homburger | ........ | A01K 67/0333 |
| | | | | | | 435/252.3 |
| 7,214,786 | B2 | * | 5/2007 | Kovalic | .............. | A01G 22/00 |
| | | | | | | 536/23.6 |
| 9,029,636 | B2 | * | 5/2015 | Wu | .......... | A01H 5/10 |
| | | | | | | 800/285 |
| 2003/0041348 | A1 | | 2/2003 | Simmons et al. | | |
| 2005/0277589 | A1 | | 12/2005 | Arranz | | |
| 2011/0131679 | A2 | * | 6/2011 | La Rosa | ............... | C07K 14/415 |
| | | | | | | 800/278 |
| 2012/0020940 | A1 | | 1/2012 | Durner et al. | | |
| 2013/0225481 | A1 | | 8/2013 | Yang et al. | | |

OTHER PUBLICATIONS

Yang et al., "Antimicrobial efficacy and toxicity of novel CAMPs against P. aeruginosa infection in a murine skin wound infection model," BMC Microbiology, 2019, 19: 293, 1-12. (Year: 2019).*
Yang et al., "Beta-defensin derived cationic antimicrobial peptides with potent killing activity against gram negative and gram positive bacteria," BMC Microbiology, 2018, 18: 54, 1-14. (Year: 2018).*
International Preliminary Report on Patentability for PCT Application No. PCT/US2018/000053, dated Aug. 29, 2019, 7 pages.
Goffredi et al "Genomic versatility and functional variation between two dominant heterotrophic symbionts of deep-sea Osedax worms", 17 pages, Apr. 2014, The ISME Journal, Epub Nov. 14, 2013, No. 8, vol. 4; pp. 908-924; Genbank supplement, p. 1; DOI: 10.1038/ismej.2013.201.
Zhang, G. and Sunkara, L.T., 2014. Avian antimicrobial host defense peptides: from biology to therapeutic applications. Pharmaceuticals, 7(3), pp. 220-247.
Fang, M., Zhang, C., Zhang, X., Zhang, M.Z., Rottinghaus, G.E. and Zhang, S., 2016. Structure-function analysis of Avian β-defensin-6 and β-defensin-12: role of charge and disulfide bridges. BMC microbiology, 16(1), pp. 1-18.
Ma, D., Lin, L., Zhang, K., Han, Z., Shao, Y., Liu, X. and Liu, S., 2011. Three novel Anas platyrhynchos avian βdefensins, upregulated by duck hepatitis virus, with antibacterial and antiviral activities. Molecular immunology, 49 (1-2), pp. 84-96.
Klüver, E., Schulz-Maronde, S., Scheid, S., Meyer, B., Forssmann, W.G. and Adermann, K., 2005. Structure—activity relation of human β-defensin 3: influence of disulfide bonds and cysteine substitution on antimicrobial activity and cytotoxicity. Biochemistry, 44(28), pp. 9804-9816.

* cited by examiner

*Primary Examiner* — Julie Ha
(74) *Attorney, Agent, or Firm* — Shook, Hardy & Bacon L.L.P.

(57) ABSTRACT

The present invention is directed to antimicrobial agents and compositions including the same. The antimicrobial agent can include a polypeptide or a peptidomimetic of the polypeptide. The polypeptide can have a net positive charge of at least about 3 at a pH of 7.0, and a hydrophobicity of greater than 25%.

19 Claims, 47 Drawing Sheets
Specification includes a Sequence Listing.

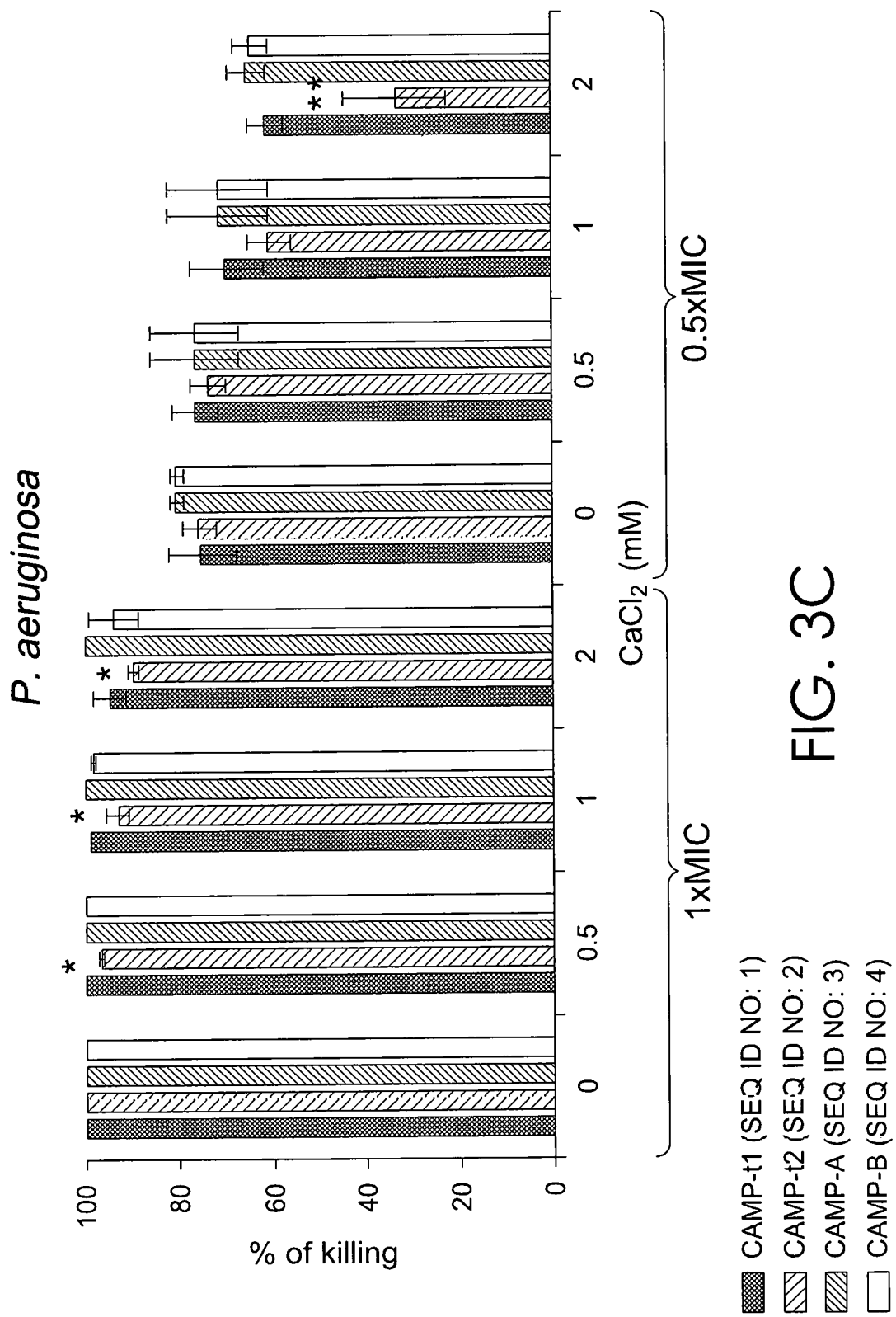

CAMP-A
(SEQ ID NO: 3)

SEQUENCE LISTING

```
<160> NUMBER OF SEQ ID NOS: 13

<210> SEQ ID NO 1
<211> LENGTH: 25
<212> TYPE: PRT
<213> ORGANISM: Artificial Sequence
<220> FEATURE:
<223> OTHER INFORMATION: Synthetic Design

<400> SEQUENCE: 1

Arg Lys Phe Leu Arg Arg Arg Gly Glu Val Ala His Phe Ser Gln Lys
1               5                   10                  15

Ser Leu Gly Leu Tyr Cys Trp Trp Trp
            20                  25

<210> SEQ ID NO 2
<211> LENGTH: 17
<212> TYPE: PRT
<213> ORGANISM: Artificial Sequence
<220> FEATURE:
<223> OTHER INFORMATION: Synthetic Design

<400> SEQUENCE: 2

Pro Ile His Arg Arg Ile Pro Pro Arg Trp Pro Arg Leu Lys Arg Arg
1               5                   10                  15

Trp
```

```
<210> SEQ ID NO 3
<211> LENGTH: 20
<212> TYPE: PRT
<213> ORGANISM: Artificial Sequence
<220> FEATURE:
<223> OTHER INFORMATION: Synthetic Design

<400> SEQUENCE: 3

Leu Arg Arg Leu Lys Pro Leu Ile Arg Pro Trp Leu Arg Pro Leu Arg
1               5                   10                  15

Arg Trp Trp Trp
            20

<210> SEQ ID NO 4
<211> LENGTH: 11
<212> TYPE: PRT
<213> ORGANISM: Artificial Sequence
<220> FEATURE:
<223> OTHER INFORMATION: Synthetic Design

<400> SEQUENCE: 4

Arg Arg Arg Trp Arg Lys Arg Arg Trp Trp Trp
1               5                   10

<210> SEQ ID NO 5
<211> LENGTH: 45
<212> TYPE: PRT
<213> ORGANISM: Gallus gallus

<400> SEQUENCE: 5

Gly Pro Asp Ser Cys Asn His Asp Arg Gly Leu Cys Arg Val Gly Asn
1               5                   10                  15

Cys Asn Pro Gly Glu Tyr Leu Ala Lys Tyr Cys Phe Glu Pro Val Ile
            20                  25                  30

Leu Cys Cys Lys Pro Leu Ser Pro Thr Pro Thr Lys Thr
        35                  40                  45

<210> SEQ ID NO 6
<211> LENGTH: 45
<212> TYPE: PRT
<213> ORGANISM: Artificial Sequence
<220> FEATURE:
<223> OTHER INFORMATION: Synthetic Design

<400> SEQUENCE: 6

Gly Pro His Ser Ala Asn His Val Arg Gly Leu Ala Arg Val Gly Asn
1               5                   10                  15

Ala Asn Pro Gly Leu Tyr Leu Ala Lys Tyr Ala Phe Ile Pro Val Ile
            20                  25                  30

Leu Ala Ala Lys Pro Leu Ser Pro Thr Pro Thr Lys Thr
        35                  40                  45

<210> SEQ ID NO 7
<211> LENGTH: 45
<212> TYPE: PRT
<213> ORGANISM: Artificial Sequence
<220> FEATURE:
<223> OTHER INFORMATION: Synthetic Design
```

<400> SEQUENCE: 7

Gly Pro Arg Ser Ser Asn His Lys Arg Gly Leu Ser Arg Val Gly Asn
1               5                   10                  15

Ser Asn Pro Gly Lys Tyr Leu Ala Lys Tyr Ala Phe Arg Pro Val Ile
            20                  25                  30

Leu Ala Ala Lys Pro Leu Ser Pro Thr Pro Thr Lys Thr
        35                  40                  45

<210> SEQ ID NO 8
<211> LENGTH: 45
<212> TYPE: PRT
<213> ORGANISM: Artificial Sequence
<220> FEATURE:
<223> OTHER INFORMATION: Synthetic Design

<400> SEQUENCE: 8

Gly Pro Arg Ser Ala Asn His Lys Arg Gly Leu Ala Arg Val Gly Asn
1               5                   10                  15

Ala Asn Pro Gly Lys Tyr Leu Ala Lys Tyr Ser Phe Arg Pro Val Ile
            20                  25                  30

Leu Ser Ser Lys Pro Leu Ser Pro Thr Pro Thr Lys Thr
        35                  40                  45

<210> SEQ ID NO 9
<211> LENGTH: 45
<212> TYPE: PRT
<213> ORGANISM: Artificial Sequence
<220> FEATURE:
<223> OTHER INFORMATION: Synthetic Design
<220> FEATURE:
<221> NAME/KEY: MOD_RES
<222> LOCATION: (5)..(5)
<223> OTHER INFORMATION: Abu
<220> FEATURE:
<221> NAME/KEY: MOD_RES
<222> LOCATION: (34)..(34)
<223> OTHER INFORMATION: Abu

<400> SEQUENCE: 9

Gly Pro Asp Ser Xaa Asn His Asp Arg Gly Leu Cys Arg Val Gly Asn
1               5                   10                  15

Cys Asn Pro Gly Glu Tyr Leu Ala Lys Tyr Cys Phe Glu Pro Val Ile
            20                  25                  30

Leu Xaa Cys Lys Pro Leu Ser Pro Thr Pro Thr Lys Thr
        35                  40                  45

<210> SEQ ID NO 10
<211> LENGTH: 45
<212> TYPE: PRT
<213> ORGANISM: Artificial Sequence
<220> FEATURE:
<223> OTHER INFORMATION: Synthetic Design
<220> FEATURE:
<221> NAME/KEY: MOD_RES
<222> LOCATION: (5)..(5)
<223> OTHER INFORMATION: Abu
<220> FEATURE:
<221> NAME/KEY: MOD_RES
<222> LOCATION: (12)..(12)
<223> OTHER INFORMATION: Abu
<220> FEATURE:
<221> NAME/KEY: MOD_RES
<222> LOCATION: (27)..(27)
<223> OTHER INFORMATION: Abu
<220> FEATURE:
<221> NAME/KEY: MOD_RES
<222> LOCATION: (34)..(34)
<223> OTHER INFORMATION: Abu

<400> SEQUENCE: 10

Gly Pro Asp Ser Xaa Asn His Asp Arg Gly Leu Xaa Arg Val Gly Asn
1               5                   10                  15

Cys Asn Pro Gly Glu Tyr Leu Ala Lys Tyr Xaa Phe Glu Pro Val Ile
            20                  25                  30

Leu Xaa Cys Lys Pro Leu Ser Pro Thr Pro Thr Lys Thr
        35                  40                  45

<210> SEQ ID NO 11
<211> LENGTH: 45
<212> TYPE: PRT
<213> ORGANISM: Artificial Sequence
<220> FEATURE:
<223> OTHER INFORMATION: Synthetic Design
<220> FEATURE:
<221> NAME/KEY: MOD_RES
<222> LOCATION: (5)..(5)
<223> OTHER INFORMATION: Abu
<220> FEATURE:
<221> NAME/KEY: MOD_RES
<222> LOCATION: (12)..(12)
<223> OTHER INFORMATION: Abu
<220> FEATURE:
<221> NAME/KEY: MOD_RES
<222> LOCATION: (17)..(17)
<223> OTHER INFORMATION: Abu
<220> FEATURE:
<221> NAME/KEY: MOD_RES
<222> LOCATION: (27)..(27)
<223> OTHER INFORMATION: Abu
<220> FEATURE:
<221> NAME/KEY: MOD_RES
<222> LOCATION: (34)..(34)
<223> OTHER INFORMATION: Abu
<220> FEATURE:
<221> NAME/KEY: MOD_RES
<222> LOCATION: (35)..(35)
<223> OTHER INFORMATION: Abu

<400> SEQUENCE: 11

Gly Pro Asp Ser Xaa Asn His Asp Arg Gly Leu Xaa Arg Val Gly Asn
1               5                   10                  15

Xaa Asn Pro Gly Glu Tyr Leu Ala Lys Tyr Xaa Phe Glu Pro Val Ile
            20                  25                  30

Leu Xaa Xaa Lys Pro Leu Ser Pro Thr Pro Thr Lys Thr
        35                  40                  45

<210> SEQ ID NO 12
<211> LENGTH: 45
<212> TYPE: PRT
<213> ORGANISM: Artificial Sequence
<220> FEATURE:
<223> OTHER INFORMATION: Synthetic Design

<400> SEQUENCE: 12

Gly Pro His Ser Cys Asn His Gln Arg Gly Leu Cys Arg Val Gly Asn
1               5                   10                  15

Cys Asn Pro Gly Tyr Tyr Leu Ala Lys Tyr Cys Phe Ser Pro Val Ile
            20                  25                  30

Leu Cys Cys Lys Pro Leu Ser Pro Thr Pro Thr Lys Thr
        35                  40                  45

```
<210> SEQ ID NO 13
<211> LENGTH: 42
<212> TYPE: PRT
<213> ORGANISM: Gallus gallus

<400> SEQUENCE: 13

Ser Pro Ile His Ala Cys Arg Tyr Gln Arg Gly Val Cys Ile Pro Gly
1               5                   10                  15

Pro Cys Arg Trp Pro Tyr Tyr Arg Val Gly Ser Cys Gly Ser Gly Leu
            20                  25                  30

Lys Ser Cys Cys Val Arg Asn Arg Trp Ala
            35                  40
```

ANTIMICROBIAL AGENTS AND COMPOSITIONS COMPRISING THE SAME

CROSS REFERENCE TO RELATED APPLICATIONS

This application is a 35 U.S.C. § 371 national stage application of PCT Application Number PCT/US2018/000053, filed Feb. 16, 2018, and entitled "ANTIMICROBIAL AGENTS AND COMPOSITIONS COMPRISING THE SAME", which claims the benefit of priority of U.S. Application No. 62/460,398, filed on Feb. 17, 2017, and entitled "COMPOSITIONS COMPRISING AVIAN BETA DEFENSIN ANALOGUES". The entirety of each of the aforementioned applications is incorporated by reference herein.

FIELD OF THE INVENTION

The present invention relates to an antimicrobial agent.

SEQUENCE LISTING

A text file in compliance with ASCII and havening a ".txt" extension has been electronically submitted via EFS-Web. The text file is named "SequenceListing", was created on Feb. 15, 2018, and is 6.21 KB. The text file is expressly incorporated by reference in its entirety.

BACKGROUND OF THE INVENTION

Rapid emergence of antimicrobial resistance poses a major global threat to public health and economy. Excessive use and misuse of antibiotics in medicine and food production contribute to the rise of drug resistant pathogens. Control and prevention of antibiotic resistance call for holistic strategies, including judicious use of antimicrobials, effective diagnostic tools, and novel therapeutic agents that are less likely to trigger resistance.

BRIEF DESCRIPTION OF THE DRAWING

Aspects are described in detail below with reference to the attached drawing figures.

FIG. 1C presents a predicted three dimensional structure of CAMP-A (SEQ ID NO: 3) further derived from CAMP-t2 (SEQ ID NO: 2), wherein positively charged amino acid residues are shown in red, hydrophobic amino acid residues are shown in blue, and prolines are shown in green, in accordance with an aspect of the present invention;

FIG. 1D presents a predicted three dimensional structure of CAMP-B (SEQ ID NO: 4) further derived from CAMP-t2 (SEQ ID NO: 2), with positively charged amino acid residues (red), hydrophobic amino acid residues (blue), and prolines (green), in accordance with an aspect of the present invention;

FIG. 3C is a bar graph that show the effect of salt on the antibacterial activity of CAMPs (SEQ ID NOs: 1, 2, 3, and 4) at 1×MIC and 0.5×MIC against *P. aeruginosa*, represented as a percent of killing at 0, 0.5, 1, and 2 mM CaCl2, in accordance with an aspect of the present invention;

DETAILED DESCRIPTION OF THE INVENTION

Figure 1A:
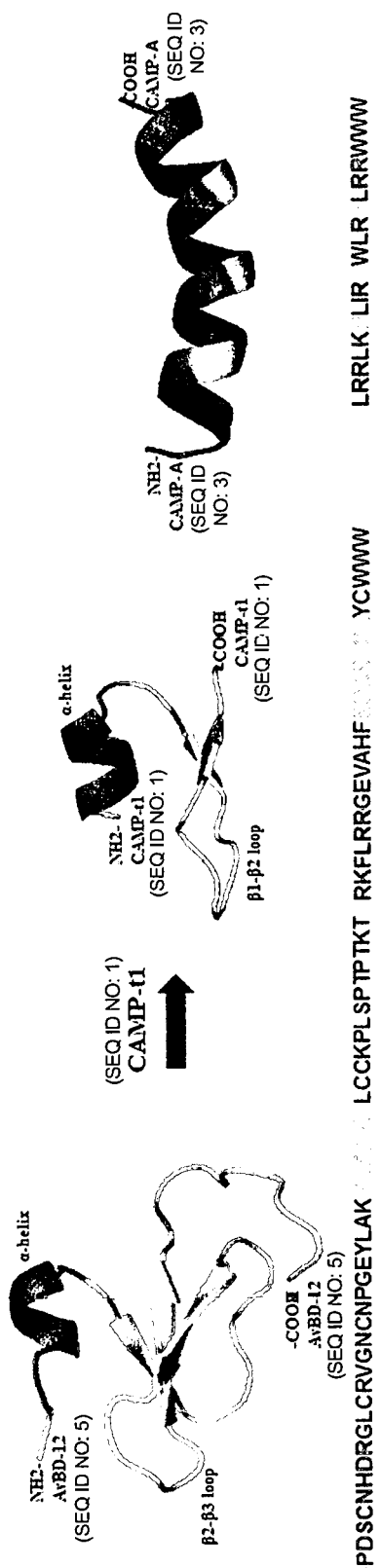
FIG. 1A presents predicted three dimensional structure of CAMP-t1 (SEQ ID NO: 1) derived from AvBD-12 (SEQ ID NO: 5), having α-helix (red) and loop (β2-β3 loop in AvBD-12 [SEQ ID NO: 5], β1-β2 loop in template CAMP-t1 [SEQ ID NO: 1]) (green), in accordance with an aspect of the present invention.

Although the present disclosure has been described with reference to preferred aspects, workers skilled in the art will recognize that changes may be made in form and detail without departing from the spirit and scope of the disclosure.

The rapid emergence and spread of antimicrobial resistance, particularly those associated with *Pseudomonas aeruginosa* and *Staphylococcus* spp., have become a serious threat to public health. The Centers for Disease Control and Prevention (CDC) estimated that each year in the United States there are approximately 88,000 cases and 11,000 deaths due to infections with methicillin-resistant *Staphylococcus aureus* (MRSA). Various studies have been conducted to search for new classes of antimicrobial therapeutic agents or antibiotic alternatives with novel targets and modes of action.

Beta-defensins are small, cationic, antimicrobial peptides that constitute a first line of innate defense against pathogenic bacteria, fungi, and viruses. Beta-defensins possess various biological properties, including broad-spectrum microbicidal activity, neutralization of LPS, activation of macrophages and dendritic cells, chemo-attraction of dendritic cells, monocytes, and T lymphocytes to the site of infection.

Avian β-defensins ("AvBD") are cationic antimicrobial peptides ("CAMPs") with broad-spectrum antimicrobial activity, chemotactic property and low host cytotoxicity. However, their bactericidal activity is greatly compromised under physiological salt concentrations which limits the use of these peptides as antimicrobial therapeutic agents. Additionally, the length and the complex structure of AvBDs (SEQ ID NOs: 5, 6, 7, 8, 9, 10, 11, 12, and 13), involving β-sheets and three conserved disulfide bridges, resulted in a high cost of production. Accordingly, salt sensitivity is a major obstacle to the application of AvBDs (SEQ ID NOs: 5, 6, 7, 8, 9, 10, 11, 12, and 13) as chemotherapeutic agents. Other means than disclosed herein were previously unsuccessful in solving the problems of salt sensitivity. Protease susceptibility is also an obstacle to the application of AvBDs (SEQ ID NOs: 5, 6, 7, 8, 9, 10, 11, 12, and 13). Increasing protease resistance by other means than disclosed herein were previously unsuccessful regarding AvBDs (SEQ ID NOs: 5, 6, 7, 8, 9, 10, 11, 12, and 13) because said means resulted in detrimentally elevated hemolytic activity and prohibitively increased manufacturing costs.

As discussed further below, the antimicrobial agents and compositions comprising the same disclosed herein alleviate one or more of the problems discussed above. For instance, in certain aspects, the antimicrobial agents and compositions comprising the same disclosed herein can exhibit unexpectedly potent antimicrobial activity, much improved resistance to salts and proteases, and reduced cytotoxicity to host cells.

Throughout this disclosure, the terms "peptide" and "polypeptide" are used interchangeably. Thus, unless specifically noted otherwise, "peptide" and "polypeptide" shall not limit one or the other, but shall be construed to have the same, broadest meaning. Additionally, as used herein, unless otherwise specified, the term "peptidomimetic" refers to a compound designed to mimic a peptide or polypeptide, inclusive in this definition is a polypeptide comprising one or more D-amino acids. Unless otherwise specified, the term "peptoid" refers to one type of a peptidomimetic, as used herein, where the side chains of the amino acids are attached to the nitrogen atom of the peptide backbone, rather than to the α-carbons. As used herein, unless otherwise specified, the term "β-peptide" refers to one type of a peptidomimetic that comprises β amino acids, which have their amino group bonded to the β carbon rather than the α carbon. As used herein, the hydrophobicity % refers to the number of aromatic amino acids and aliphatic amino acids in a polypeptide relative to the total number of amino acids in the polypeptide (×100).

Throughout this disclosure, abbreviations, acronyms and shorthand notations are used to aid the understanding of certain concepts pertaining to the present invention and are solely intended for the purpose of providing an easy methodology of communicating the ideas expressed herein and are in no way meant to limit the scope of the aspects of the invention. The following is a list of several of these acronyms:

ANOVA One-way analysis of variance
BSA Bovine serum albumin
CFU Colony-forming unit
C.I. Chemotaxis index
DCs Dendritic cells
ESI-MS Electrospray ionization mass spectrometry
FBS Fetal bovine serum
fMLF N-Formyl-methionyl-leucyl-phenylalan
Fmoc 9-fluorenyl-methoxycarbonyl
GFP Green fluorescent protein
GM-CSF Granulocyte macrophage colony-stimulating factor
hBD6 Human β-defensin 6
LB Luria-Bertani
LPS Lipopolysaccharides
LTA Lipoteichoic acid
MIC Minimum inhibitory concentration
MBC Minimum bactericidal concentration
MRSA Methicillin-resistant *Staphylococcus aureus*
MRSP Methicillin resistant *Staphylococcus pseudintermedius*
PBS Phosphate buffered saline
mRBCs Mouse Red blood cells
RP-HPLC Reversed-phase high performance liquid chromatography
SD Standard deviation
SEM Scanning electron microscopy
TSA Trypticase soy agar As discussed above, aspects of the present invention relate to antimicrobial agents and compositions comprising one or more of the antimicrobial agents. In some aspects, the antimicrobial agent comprises a polypeptide, a peptidomimetic of the polypeptide, or a combination thereof.

Antimicrobial Agents Comprising a Short Polypeptide, or a Peptidomimetic of the Polypeptide In various aspects, the polypeptide may exhibit a net positive charge. The polypeptide may exhibit a net positive charge that is at least +3 at a pH of 7.0, in one aspect. In another aspect, the polypeptide may exhibit a net positive charge that is at least +5 at a pH of 7.0. In one aspect, the polypeptide may exhibit a net positive charge that is at least +7 at a pH of 7.0. In some aspects, the polypeptide may exhibit a net positive charge from +3 to +9. The polypeptide may exhibit a net positive charge from +4 to +7, in some aspects. The net charge of polypeptides at pH 7.0 can be determined by one skilled in the art knowing the pKa of the various functional groups of the individual amino acids in the polypeptide sequence, which are identified in common biochemistry texts, such as Biochemistry, 2nd edition, Donald Voet and Judith G. Voet, 1995, published by Wiley, and herein incorporated by reference in its entirety. Furthermore, the net charge for a polypeptide can be calculated using an online peptide property calculator, found at PepCalc.com.

In various aspects, the polypeptide may exhibit a hydrophobicity that is greater than 20%, or greater than 25%. In aspects, the polypeptide may exhibit a hydrophobicity between about 20% and 60%. In some aspects, the polypeptide may exhibit a hydrophobicity of about 25% to 50%. As used herein, hydrophobicity expressed as a percent refers to the number of aromatic amino acids and aliphatic amino acids in a polypeptide relative to the total number of amino acids in that polypeptide, times 100. Aromatic amino acids and aliphatic amino acids are known to one skilled in the art and are also identified in common biochemistry texts, such as Biochemistry, 2nd edition, Donald Voet and Judith G. Voet, 1995, published by Wiley, and herein incorporated by reference in its entirety.

In aspects of the present invention, the polypeptide may have at least one C-terminal tryptophan amino acid. In another aspect, the polypeptide may have at least two C-terminal tryptophan amino acids. The polypeptide may have three or more C-terminal tryptophan amino acids, in further aspects. In the same or alternative aspects, the C-terminal amino acid of the polypeptide is amidated. In other embodiments, the C-terminal amino acid of the polypeptide may not be amidated or may optionally be amidated. The polypeptide, in some aspects, may have an N-terminal amino acid that is acetylated. In other embodiments, the N-terminal amino acid of the polypeptide may not be acetylated or may optionally be acetylated.

In one aspect, the polypeptide is 40 amino acids or less in length. In an aspect, the polypeptide is 30 amino acids or less in length. In another aspect, the polypeptide comprises at least 10 amino acids in length. In a preferred aspect, the polypeptide comprises at least about 10 amino acids and less than 30 amino acids in length.

In aspects, the polypeptide comprises an amino acid sequence having at least 80%, 90%, 95%, or 99% sequence identity to at least one of SEQ ID NOs: 1, 2, 3, and/or 4. In various aspects, the polypeptide is selected from the group consisting of SEQ ID NOs: 1, 2, 3, and/or 4. In certain aspects, the antimicrobial agent can be a peptidomimetic of the polypeptide.

As discussed above, the polypeptide may comprise an amino acid sequence having at least about 80%, 90%, 95%, or 99% sequence identity to at least one of SEQ ID NOs: 1, 2, 3, and/or 4. In such aspects to arrive at a polypeptide with less than 100% sequence identity to at least one of SEQ ID NOs: 1, 2, 3, and/or 4, any of the amino acids may be substituted on the basis of similarity in polarity, charge, solubility, hydrophobicity, hydrophilicity, and/or the amphipathic nature of the residues involved. For example: nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. In certain aspects, amino acid substitutions may be made on the basis of the hydropathic index of amino acids. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The use of the hydropathic amino acid index in conferring interactive biological function on a protein is understood in the art (Kyte and Doolittle, J. Mol. Biol. 157:105-132, 1982). It is known that in certain instances, certain amino acids may be substituted for other amino acids having a similar hydropathic index or score and still retain a similar biological activity. In making changes based upon the hydropathic index, in certain aspects the substitution of amino acids whose hydropathic indices are within ±2 is included, while in other, aspects amino acid substitutions that are within ±1 are included, and in yet other aspects amino acid substitutions within ±0.5 are included.

In certain aspects, at least a portion of the polypeptide is adapted to form an alpha-helical structure in physiological conditions. Example physiological conditions can include a pH of about 6 to about 8. In the same or alternative aspects, under physiological conditions two or more of the positive charges of the positively charged amino acids can be positioned on the same side of a helical surface.

In aspects, the polypeptide may exhibit greater antimicrobial activity than an endogenous beta-defensin compound, such as avian beta-defensin 6 (AvBD-6 [SEQ ID NO: 13]). In aspects, the polypeptide may exhibit greater antimicrobial activity against $P.$ $aeruginosa$ than an endogenous beta-defensin compound, such as avian beta-defensin 6 (AvBD-6 [SEQ ID NO: 13]). In various aspects, the polypeptide may exhibit a Minimum Inhibitory Concentration of less than 250 μg/ml, 150 μg/ml, and/or 75 μg/ml against $P.$ $aeruginosa$, as determined according to the Antimicrobial Activity Assay specified in the Example One. In some aspects, the polypeptide may exhibit a Minimum Inhibitory Concentration of less than 250 μg/ml, 150 μg/ml, and/or 75 μg/ml against one or more multidrug-resistant $P.$ $aeruginosa$ strains, as determined according to the Antimicrobial Activity Assay specified in Example One. Example multidrug resistant $P.$ $aeruginosa$ strains include strains that exhibit resistance to chloramphenicol, tetracycline, sulfamethoxazole, and/or β-lactam antibiotics (e.g., amoxicillin, ampicillin and cefazolin). In one aspect, the polypeptide may exhibit a Minimum Inhibitory Concentration of 64 μg/ml or less against $P.$ $aeruginosa$ and/or one or more multidrug-resistant $P.$ $aeruginosa$ strains, as determined according to the Antimicrobial Activity Assay specified in Example One.

In aspects, the polypeptide may exhibit greater antimicrobial activity against than an endogenous beta-defensin compound. For example in one aspect, the polypeptide may exhibit a Minimum Inhibitory Concentration of less than 250 μg/ml, 150 μg/ml, and/or 75 μg/ml against $S.$ $pseudintermedius$ as determined according to the Antimicrobial Activity Assay specified in Example One. In some aspects, the polypeptide may exhibit a Minimum Inhibitory Concentration of less than 250 μg/ml, 150 μg/ml, and/or 75 μg/ml against one or more methicillin resistant $S.$ $pseudintermedius$ (MRSP) strains, as determined according to the Antimicrobial Activity Assay specified in Example One. In one aspect, the polypeptide may exhibit a Minimum Inhibitory Concentration of about 64 μg/ml or less against $S.$ $pseudintermedius$ and/or one or more methicillin resistant $S.$ $pseudintermedius$ (MRSP) strains, as determined according to the Antimicrobial Activity Assay specified in Example One.

In aspects, the polypeptide may exhibit greater antimicrobial activity against $S.$ $aureus$ than an endogenous beta-defensin compound. For instance, in one aspect, the polypeptide may exhibit a Minimum Inhibitory Concentration of less than 250 μg/ml, 150 μg/ml, and/or 75 μg/ml against $S.$ $aureus$ as determined according to the Antimicrobial Activity Assay specified in the Example One. In one aspect, the polypeptide may exhibit a Minimum Inhibitory Concentration of about 32 μg/ml or less against $S.$ $aureus$, as determined according to the Antimicrobial Activity Assay specified in Example One.

In aspects, the polypeptide may exhibit greater salt resistance than an endogenous beta-defensin-type compound. In such aspects, this greater salt resistance can be exhibited as little to no reduction in antimicrobial activity in the presence of a salt. In one embodiment, the polypeptide may exhibit a same or similar Minimum Inhibitory Concentration against one or more of $P.$ $aeruginosa$ and $S.$ $aureus$ at concentrations of 0 to 150 mM NaCl or 0 to 2 mM $CaCl_2$, as determined according to the Antimicrobial Activity Assay specified in Example One.

In aspects, the polypeptide may exhibit low hemolytic activity and low cytotoxicity to mouse RBCs. In an aspect, the polypeptide may exhibit a Minimum Hemolytic Concentration (MHC) that is greater than or about 128 µg/ml or greater than about 512 µg/ml in the presence of mRBCs, as determined in the Hemolytic Assay of Example One. In one aspect, the polypeptide produced hemolysis in less than or about 5% of mRBCs at a concentration of about 512 µg/ml, as determined in the Hemolytic Assay of Example One. In another embodiment, the polypeptide produced hemolysis in less than or about 20% of mouse RBCs at concentrations of about 250 µg/ml and/or 150 µg/ml, as determined in the Hemolytic Assay of Example One.

In some aspects, the polypeptide may produce no changes to cell viability or exhibit very low negative impacts on cell viability. In one aspect, the polypeptide does not produce negative changes to cell viability of murine immature dendritic cell line JAWSII and or CHO-K1 cells at concentrations of 64, 128, 256, and/or 512 µg/ml, as determined using the Cell Cytotoxicity Assay Example One.

In aspects, the polypeptide may exhibit greater protease resistance than an endogenous beta-defensin-type compound. Example proteases include chrymotrypsin, elastase, matrilysin, elastase, and/or cathepsin B. In one aspect, the polypeptide may not be cleaved by metalloproteinases matrilysin, elastase, and/or cathepsin B up to concentrations of about 20 µg/ml. In one aspect, the polypeptide may exhibit about a 90% percent killing against one or more of $P.$ $aeruginosa$ and $S.$ $aureus$ after exposure to one or more proteases at concentrations below or about 0.12 µg/ml. The polypeptide may exhibit, in one aspect, about 80% percent killing against $P.$ $aeruginosa$ after exposure to one or more proteases at concentrations below or about 0.66 µg/ml. In one more aspect, the polypeptide may exhibit about 90% percent killing against $S.$ $aureus$ after exposure to one or more proteases at concentrations below or about 0.66 µg/ml. In yet another aspect, the polypeptide may exhibit about 80% percent killing against $S.$ $aureus$ after exposure to one or more proteases at concentrations below or about 1.2 µg/ml.

The polypeptide or peptidomimetic of the polypeptide may include one or more of any of the previously-described characteristics, either alone or in combination. As such, the polypeptide is may exhibit a combination of characteristics and properties involving net charges, hydrophobicity, Minimum Inhibitory Concentrations, and/or any other features and combinations of features discussed above, for example.

Antimicrobial Agents Comprising a Longer Polypeptide or a Peptidomimetic of the Polypeptide Certain aspects of the present invention relate to antimicrobial agents having longer polypeptides or peptidomimetics of the same than those discussed in the preceding section. In certain aspects, the composition can comprise a synthetic avian beta-defensin analogue. In aspects, the avian beta-defensin analogue or the synthetic avian beta-defensin analogue comprises a polypeptide.

The polypeptide may, in various aspects, exhibit a net positive charge. The polypeptide may exhibit a net positive charge that is at least about +5 at a pH of 7.0, in one aspect. In another aspect, the polypeptide may exhibit a net positive charge that is at least about +7 at a pH of 7.0. In one aspect, the polypeptide may exhibit a net positive charge that is about +9 at a pH of 7.0. In some aspects, the polypeptide may exhibit a net positive charge from about +7 to about +9. The net positive charge can be determined as described above.

In various aspects, the polypeptide may exhibit a hydrophobicity that is equal to or greater than about 33%. In some aspects, the polypeptide may exhibit a hydrophobicity of about 40% or more. The polypeptide may exhibit a hydrophobicity between about 30% and about 60%, in various aspects. The hydrophobicity can be determined as described above.

In one aspect, the polypeptide comprises about 30 to about 50 amino acids. In another aspect, the polypeptide comprises about 40 to about 50 amino acids in length. In an aspect, the polypeptide is about 50 amino acids or less in length. In one aspect, the polypeptide may be linear.

In some aspects, the polypeptide has an amino acid sequence that is at least, or about, 80% or 90% identical to SEQ ID NO: 5 (AvBD-12 wt). In a preferred aspect, the polypeptide is selected from a group consisting of SEQ ID NO: 6, 7, and 8 (AvBD12-A1, AvBD12-A2, AvBD12-A3, respectively). In yet a more preferred aspect, the polypeptide is selected from a group consisting of SEQ ID NO: 6, 7, 8 and a sequence having at least about 90%, 95%, or 99% amino acid sequence identity to one of SEQ ID NOs: 6, 7, 8.

In certain aspects, the polypeptide contains less than three Cysteine amino acids, less than two Cysteine amino acids, or one Cysteine amino acid. In one aspect, the polypeptide does not contain a Cysteine amino acid. In certain aspects, the polypeptide contains less than three disulfide bonds, less than two disulfide bonds, or one disulfide bond. In one aspect, polypeptide does not contain a disulfide bond.

As discussed above, the polypeptide may comprise an amino acid sequence having at least about 80%, 90%, 95%, or 99% sequence identity to at least one of SEQ ID NOs: 6, 7, or 8. In such aspects to arrive at a polypeptide with less than 100% sequence identity to at least one of SEQ ID NOs: 6, 7, or 8, any of the amino acids may be substituted on the basis of similarity in polarity, charge, solubility, hydrophobicity, hydrophilicity, and/or the amphipathic nature of the residues involved. For example: nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine. and glutamine; positively charged (basic) amino acids include arginine, lysine, and histidine; and negatively charged (acidic) amino acids include aspartic acid and glutamic acid. In certain aspects, amino acid substitutions may be made on the basis of the hydropathic index of amino acids. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The use of the hydropathic amino acid index in conferring interactive biological function on a protein is understood in the art (Kyte and Doolittle, J. Mol. Biol. 157:105-132, 1982). It is known that in certain instances, certain amino acids may be substituted for other amino acids having a similar hydropathic index or score and still retain a similar biological activity. In making changes based upon the hydropathic index, in certain aspects the substitution of amino acids whose hydropathic indices are within ±2 is included, while in other, aspects amino acid substitutions that are within ±1 are included, and in yet other aspects amino acid substitutions within ±0.5 are included.

In aspects, the polypeptide may exhibit greater antimicrobial activity than an endogenous beta-defensin compound, such as avian beta-defensin 12 (AvBD-12 [SEQ ID NO: 5]). In aspects, the polypeptide may exhibit greater antimicrobial activity against *P. aeruginosa* than an endogenous beta-defensin compound. The polypeptide may exhibit about an 80% killing of *P. aeruginosa* in 150 mM NaCl when the polypeptide is present in a concentration of 32 µg/ml as determined by the Antimicrobial Activity Assay of Example Two. In one aspect the polypeptide comprises an amino acid of SEQ ID NOs: 7 or 8 and may exhibit at least about 90% killing of *P. aeruginosa* in 150 mM NaCl when the polypeptide is present in a concentration of 16 µg/ml as determined by the Antimicrobial Activity Assay of Example Two. In some aspects, the polypeptide may exhibit a Minimum Inhibitory Concentration of less than 250 µg/ml, 150 µg/ml, and/or 75 µg/ml against *P. aeruginosa* in low salt conditions, defined as about 5 mM NaCl. In a further aspect, the polypeptide may exhibit a Minimum Inhibitory Concentration of about 20 µg/ml or less against *P. aeruginosa* in low salt conditions and may comprise an amino acid sequence that has at least 90%, 95%, 99%, or 100% sequence identity to one of SEQ ID NOs: 7 or 8.

In aspects, the polypeptide may exhibit greater antimicrobial activity against *E. coli* than an endogenous beta-defensin compound, such as avian beta-defensin 12 (AvBD-12 [SEQ ID NO: 5]). In one aspect, the polypeptide may exhibit at least about 80% killing of *E. coli* in 150 mM NaCl when the polypeptide is present in a concentration of at least 16 µg/ml as determined by the Antimicrobial Activity Assay Example Two. In another aspect, the polypeptide may exhibit at least about 80% killing of *E. coli* in 150 mM NaCl when the polypeptide is present in a concentration of at least 16 µg/ml as determined by the Antimicrobial Activity Assay of Example Two and may have an amino acid sequence that has at least 90%, 95%, 99%, or 100% sequence identity to one of SEQ ID NOs: 6, 7, or 8. In some aspects, the polypeptide may exhibit a Minimum Inhibitory Concentration of less than 250 µg/ml, 150 µg/ml, and/or 75 µg/ml against *E. coli* in low salt conditions, defined as about 5 mM NaCl.

In aspects, the polypeptide may exhibit greater antimicrobial activity against *S. Typhimurium* than an endogenous beta-defensin compound, such as avian beta-defensin 12 (AvBD-12 [SEQ ID NO: 5]). In another aspect, the polypeptide may exhibit about 70% killing against *S. Typhimurium* in 150 mM NaCl when the polypeptide is present in a concentration of at least 16 µg/ml as determined by the Antimicrobial Activity Assay Example Two. In one aspect, the polypeptide comprises an amino acid sequence of one of SEQ ID NOs: 6, 7 or 8 and may exhibit about at least about 90% killing of *S. Typhimurium* in 150 mM NaCl when the polypeptide is present in a concentration of at least 16 µg/ml as determined by the Antimicrobial Activity Assay of Example Two. In a further aspect, the polypeptide may exhibit a Minimum Inhibitory Concentration of about 20 µg/ml or less against *S. Typhimurium* in low salt conditions.

In aspects, the polypeptide may exhibit greater antimicrobial activity against *S. aureus* than an endogenous beta-defensin compound, such as avian beta-defensin 12 (AvBD-12 [SEQ ID NO: 5]). In one aspect, the polypeptide may exhibit about at least about 70% killing of *S. aureus* in 150 mM NaCl when the polypeptide is present in a concentration of 16 µg/ml as determined by the Antimicrobial Activity Assay of Example Two. In another aspect, the polypeptide comprises an amino acid sequence identity of one of SEQ ID NO: 6, 7 or 8 and may exhibit about at least about 70% killing of *S. aureus* in 150 mM NaCl when the polypeptide is present in a concentration of 16 µg/ml as determined by the Antimicrobial Activity Assay of Example Two. In some aspects, the polypeptide may exhibit a Minimum Inhibitory Concentration of less than 250 µg/ml, 150 µg/ml, and/or 75 µg/ml against *S. aureus* in low salt conditions, defined as about 5 mM NaCl.

In some aspects, the polypeptide may exhibit greater salt resistance than an endogenous beta-defensin-type compound, such as avian beta-defensin 12 (AvBD-12 [SEQ ID NO: 5]). For example, in one aspect, the polypeptide may exhibit a same or similar Minimum Inhibitory Concentration against one or more of *E. coli, S. Typhimurium P. aeruginosa*, and *S. aureus* at concentrations of 0 to 150 mM NaCl. In some aspects, the polypeptide may exhibit about 80% killing of *E. coli* and *P. aeruginosa* at concentrations of 0 to 150 mM NaCl.

In aspects, the polypeptide may exhibit low cytotoxicity to cells. Exemplary avian and mammalian cells include chicken macrophage cell lines HD11 and MQ-NCSU, murine dendritic cell line JAWSII, and CHO-K1 cells. In one aspect, the polypeptide may not produce negative changes to cell viability of one or more of chicken macrophage cell lines HD11 and MQ-NCSU, murine dendritic cell line JAWSII, and CHO-K1 cells at polypeptide concentrations of up to about 256 µg/ml.

The polypeptide or peptidomimetic of the polypeptide may include one or more of any of the previously-described characteristics, either alone or in combination. As such, the polypeptide is may exhibit a combination of characteristics and properties involving net charges, hydrophobicity, Minimum Inhibitory Concentrations, and/or any other features and combinations of features discussed above, for example.

Compositions and Methods of Use

In aspects, one or more of the antimicrobial agents or compositions comprising the antimicrobial agents described herein may be used as an antibiotic or component of an antibiotic composition. In such aspects, the one or more of the antimicrobial agents or compositions comprising the antimicrobial agents described herein can be utilized in a method of treatment, e.g., a method of treating a subject, which can include administering a therapeutically effective amount of the one or more of the antimicrobial agents or compositions comprising the antimicrobial agents. In certain aspects, a therapeutically effective amount can be an amount sufficient to provide a biologically beneficial effect to the subject such as by producing a beneficial change in a disease state or inhibiting the progression of a disease, such as a bacterial infection, which may include, but is not limited to, infection by any of the bacteria mentioned herein. In one or more aspects, the subject for treatment can be a human or other animal. The one or more of the antimicrobial agents or compositions comprising the antimicrobial agents described herein may be administered by any number of methods known to those of ordinary skill in the art including, but not limited to subcutaneous (subq), intravenous (I.V.), intraperitoneal (I.P.), orally, parenternaly, etc. In one aspects, a pharmaceutically acceptable carrier or formulation material may be added to the antimicrobial agent prior to or during administration. Example pharmaceutically acceptable carriers or formulation materials are described below.

In certain aspects, one or more of the antimicrobial agents or compositions comprising the antimicrobial agents described herein may be used as a food preservative or component of a food preservative. In such aspects, the one or more of the antimicrobial agents or compositions comprising the antimicrobial agents described herein may be utilized in a method of preserving a food substance or in a method of forming a food preservative. In such aspects, the methods can include combining one or more of the antimicrobial agents or compositions comprising the antimicrobial agents with a food substance. In aspects, the methods can include combining one or more of the antimicrobial agents or compositions comprising the antimicrobial agents with, optionally, one or more other components to form a food preservative. In various aspects, formulation materials may be combined with the antimicrobial agents for use in any of the methods described herein. Example formulation materials are described below.

In another aspect, one or more of the antimicrobial agents or compositions comprising the antimicrobial agents described herein may be used as a vaccine preservative or component of a vaccine preservative composition. In such aspects, the one or more of the antimicrobial agents or compositions comprising the antimicrobial agents described herein may be utilized in a method of preserving or forming a vaccine or in a method of forming a vaccine preservative composition. In such aspects, the methods can include combining one or more of the antimicrobial agents or compositions comprising the antimicrobial agents with one or more additional vaccine components. In aspects, the methods can include combining one or more of the antimicrobial agents or compositions comprising the antimicrobial agents with, optionally, one or more other components to form a vaccine preservative composition. In various aspects, formulation materials or pharmaceutically acceptable carriers may be combined with the antimicrobial agents for use in any of the methods described herein. Example pharmaceutically acceptable carriers or formulation materials are described below.

In some aspects, one or more of the antimicrobial agents or compositions comprising the antimicrobial agents described herein may be used as a vaccine adjuvant or a component of a vaccine adjuvant composition. In such aspects, the one or more of the antimicrobial agents or compositions comprising the antimicrobial agents described herein may be utilized in a method of preserving or forming a vaccine or in a method of forming a vaccine adjuvant composition. In such aspects, the methods can include combining one or more of the antimicrobial agents or compositions comprising the antimicrobial agents with one or more additional vaccine components. In aspects, the methods can include combining one or more of the antimicrobial agents or compositions comprising the antimicrobial agents with, optionally, one or more other components to form a vaccine adjuvant composition. In various aspects, formulation materials or pharmaceutically acceptable carriers may be combined with the antimicrobial agents for use in any of the methods described herein. Example pharmaceutically acceptable carriers or formulation materials are described below.

In aspects, formulation materials and pharmaceutically acceptable carriers may be used for modifying, maintaining, or preserving, for example, the pH, osmolarity, viscosity, clarity, color, isotonicity, odor, sterility, stability, rate of dissolution or release, adsorption or penetration of one or more of the compositions or agents discussed above. Suitable materials include, but are not limited to amino acids (for example, glycine, glutamine, asparagine, arginine and lysine); antimicrobials; antioxidants (for example, ascorbic acid, sodium sulfite and sodium hydrogen-sulfite); buffers (for example, borate, bicarbonate, Tris-HCl, citrates, phosphates and other organic acids); bulking agents (for example, mannitol and glycine); chelating agents (for example, ethylenediamine tetraacetic acid (EDTA)); complexing agents (for example, caffeine, polyvinylpyrrolidone, beta-cyclodextrin, and hydroxypropyl-beta-cyclodextrin); fillers; monosaccharides, disaccharides, and other carbohydrates (for example, glucose, mannose and dextrins); proteins (for example, serum albumin, gelatin and immunoglobulins); coloring, flavoring, and diluting agents; emulsifying agents; hydrophilic polymers (for example, polyvinylpyrrolidone); low molecular weight peptides; salt-forming counterions (for example, sodium); preservatives (for example, benzalkonium chloride, benzoic acid, salicylic acid, thimerosal, phenethyl alcohol, methylparaben, propylparaben, chlorhexidine, sorbic acid and hydrogen peroxide); solvents (for example, glycerin, propylene glycol and polyethylene glycol); sugar alcohols (for example, mannitol and sorbitol); suspending agents; surfactants or wetting agents (for example, pluronics, PEG, sorbitan esters, polysorbates (for example, polysorbate 20 and polysorbate 80), triton, tromethamine, lecithin, cholesterol, and tyloxapal); stability enhancing agents (for example, sucrose and sorbitol); tonicity enhancing agents (for example, alkali metal halides (for example, sodium or potassium chloride), mannitol, and sorbitol); delivery vehicles; diluents; excipients; and pharmaceutical adjuvants ("Remington's Pharmaceutical Sciences", 18'h Ed. (Gennaro, ed., Mack Publishing Company, Easton, Pa., 1990)).

Example One

Properties of Antimicrobial Agents Comprising a Short

Polypeptide, or a Peptidomimetic of the Polypeptide

Experiments were conducted to illustrate the properties robust antimicrobial activity, improved salt resistance, increased protease resistance, and reduced cytotoxicity regarding peptides, said peptides including the amino acid sequences of SEQ ID NOs: 1, 2, 3, and 4.

Statistical analysis on some or all of the data in Example One may include the following. Data presented were the means±standard deviation (SD). Differences between groups were analyzed using the one-way analysis of variance (ANOVA) followed by Duncan's test for multiple comparisons using software SPSS version 19.0 (IBM Corp., Armonk, N.Y.). Differences at p<0.05 level were considered statistically significant, and at p<0.01 level were considered extremely significant.

Example One

Design and Synthesis of Exemplary Antimicrobial Agent

Two CAMPs (CAMP-t1 [SEQ ID NO: 1] and CAMP-t2 [SEQ ID NO: 2]) have been designed to retain antimicrobial and chemotactic properties at least similar to that of wild-type AvBD-6 (SEQ ID NO: 13) and AvBD-12 (SEQ ID NO: 5), respectively. The first CAMP "template" (CAMP-t1 [SEQ ID NO: 1]) was comprised of a structural domain (N-terminal α-helix and β2-β3 loop) that is the same or similar to AvBD-12 (SEQ ID NO: 5) and which appeared to be related to the broad chemotactic activity of AvBD-12 (SEQ ID NO: 5). The second CAMP "template" (CAMP-t2 [SEQ ID NO: 2]) comprised the same or similar amino acid residues that are believed to contribute the surface charge and hydrophobicity of AvBD-6 (SEQ ID NO: 13). CAMP-t2 (SEQ ID NO: 2), the shorter peptide, was subjected to modifications using the following criteria: (1) short in length (≤20 amino acid residues), (2) optimized amphipathicity with hydrophobic and hydrophilic residues on the opposite sides of the peptide which are believed to facilitate pore formation in bacterial membranes, (3) an absence of cutting sites for one or more protease families, such as aspartic protease, cysteine protease, metalloprotease, and/or serine proteases, (4) N-terminal acetylation and C-terminal amidation believed to increase the metabolic stability, and (5) addition of C-terminal poly-tryptophan (Trp) tail to promote membrane permeabilization. The charge and hydrophobicity of the newly designed CAMPs (SEQ ID NOs: 1, 2, 3, and 4) at neutral pH were calculated using an online Peptide property calculator (PepCalc.com). Protease cutting sites were predicted by using PROSPER (https://prosper.erc.monash.edu.au) and SignalP 4.1 server (http://www.cbs.dtu.dk/services/SignalP/). The three dimensional structures of AvBDs (AvBD-12 [SEQ ID NO: 5] and AvBD-6 [SEQ ID NO: 13]) and the newly designed templates were analyzed by using the I-TASSER (Iterative Threading Assembly Refinement) protein structure and function prediction program (http://zhanglab.ccmb.med.umich.edu/I-TASSER). The distribution of selected amino acid residues were evaluated using PyMOL, a user-sponsored molecular visualization system (https://www.pymol.org/). All peptides were custom synthesized using a solid phase 9-fluorenylmethoxycarbonyl (Fmoc) method as previously synthesizing wild-type AvBDs (AvBD-12 [SEQ ID NO: 5] and AvBD-6 [SEQ ID NO: 13]) and purified by reverse phase high performance liquid chromatography (RP-HPLC) (Lifetein, Hillsborough, N.J.). The purity of the synthetic CAMPs (SEQ ID NOs: 1, 2, 3, and 4) was greater than 98.5% as verified by liquid chromatography-mass spectrometry (LC-MS) (Lifetein, Hillsborough, N.J.).

Figure 1B:
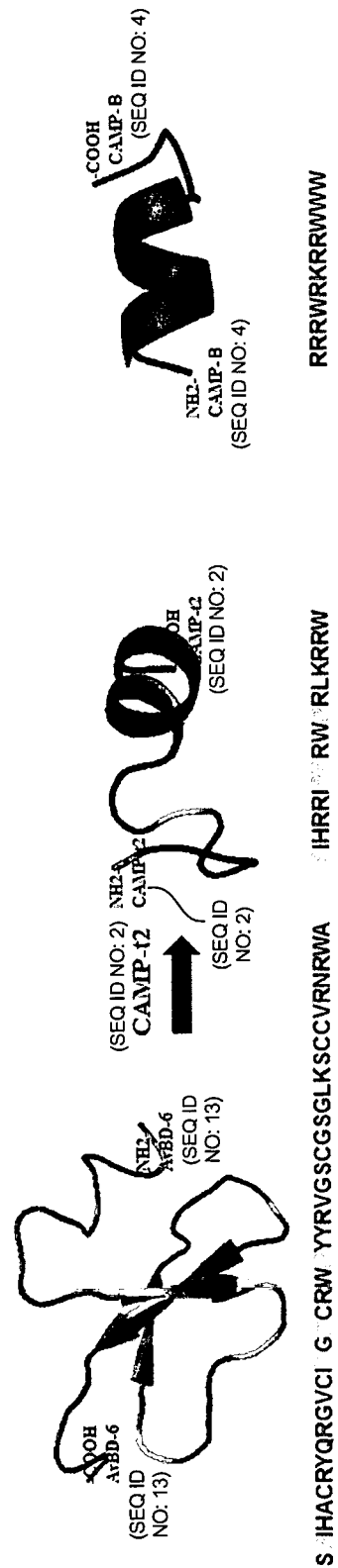
FIG. 1B presents a predicted three dimensional structure of CAMP-t2 (SEQ ID NO: 2) derived from AvBD-6 (SEQ ID NO: 13), in accordance with an aspect of the present invention.

The first CAMP template (CAMP-t1 [SEQ ID NO: 1]) was designed to retain the N-terminal α-helix and loop domain of AvBD-12 (SEQ ID NO: 5) as well as its analogues AvBD-12A2 (SEQ ID NO: 7) and AvBD-12A3 (SEQ ID NO: 8). To increase the net positive charge, the negatively charged amino acid residues Asp (D) and Glu (E) were substituted with positively charged amino acid residues Lys (K) or Arg (R). To enhance membrane permeabilizing ability, a poly-Trp (W) tail was incorporated to the C-terminus of the peptide. CAMP-t1 (SEQ ID NO: 1) included 25 amino acid residues: RKFLRRRGEVAHFSQKSLGLYCWWW. As shown in FIG. 1A, the predicted three dimensional structure of CAMP-t1 (SEQ ID NO: 1) mimics that of AvBD-12 (SEQ ID NO: 5). The second CAMP template (CAMP-t2 [SEQ ID NO: 2]) comprised amino acid residues of AvBD-6 (SEQ ID NO: 13): PIHRRIPPRWPRLKRRW. CAMP-t2 (SEQ ID NO: 2) is predicted to exhibit a coil and alpha-helix structure as shown in FIG. 1B. To optimize the antimicrobial function, CAMP-t2 (SEQ ID NO: 2) was modified based on the integrated criteria mentioned above. The resulting peptides, CAMP-A (SEQ ID NO: 3) and CAMP-B (SEQ ID NO: 4), were predicted to exhibit the alpha-helix structure as shown in FIG. 1C and FIG. 1D, respectively. Their net positive charge amino acid residues were aligned, generally, at one side of helical surface and the C-termini were coated with poly-Trp tails. The amino acid sequences and relevant biochemical characteristics of all CAMPs (CAMP-t1 [SEQ ID NO: 1], CAMP-t2 [SEQ ID NO: 2], CAMP-A [SEQ ID NO: 3], and CAMP-B [SEQ ID NO: 4]) were presented in Table 1 (contd on next page).

TABLE 1

Characteristics of newly designed peptides

| Peptide* | Amino acid | Length | Molecular Weight | Charge | Hydrophobicity |
|---|---|---|---|---|---|
| CAMP-t1 SEQ ID NO: 1 | RKFLRRRGEVAHF SQKSLGLYCWWW | 25 | 3251.84 | +4 | 44% |
| CAMP-t2 SEQ ID NO: 2 | PIHRRIPPRVVPR LKRRW | 17 | 2361.90 | +7 | 29% |
| CAMP-A SEQ ID NO: 3 | LRRLKPLIRPVVL RPLRRWWW | 20 | 2839.55 | +7 | 50% |
| CAMP-B SEQ ID NO: 4 | RRRWRKRRWWW | 11 | 1869.24 | +7 | 36% |

*CAMP-t1 (SEQ ID NO: 1), CAMP-t2 (SEQ ID NO: 2), and CAMP-B (SEQ ID NO: 4) are linked to a Trp-tail. N-terminal acetylation and C-terminal amidation were introduced to all peptides.

Example One

Membrane Permeability Assay

The membrane permeabilizing ability was determined using the propidium iodide (PI) uptake assay. PI is a fluorescent molecule that can only penetrate impaired microbial membranes and intercalate double-stranded DNA. PI staining was done according to the manufacture's instruction (Sigma Aldrich). In brief, mid-logarithmic culture of *P. aeruginosa* (ATCC 27853) was harvested by centrifugation at 1000×g for 10 minutes and re-suspended in PBS ($1 \times 10^8$ CFU/ml). The bacteria were treated with each CAMP (SEQ ID NOs: 1, 2, 3, and 4) at a concentration of 1×MIC for 15, 30, 60, and 90 minutes, respectively. After the addition of PI, the suspension was further incubated for 5 minutes at room temperature and shielded from light. The bacterial mixture was coated on a microscope slide for analysis of red fluorescence. Images were captured using a Nikon fluorescent microscope with Olympus DP2-BSE software (ECLIPSE E600, Japan) and the number of florescent cells per field was counted by the ImageJ software (NIH, Bethesda, Md.). The Membrane Permeability Assay was performed in triplicate.

Figure 2A:
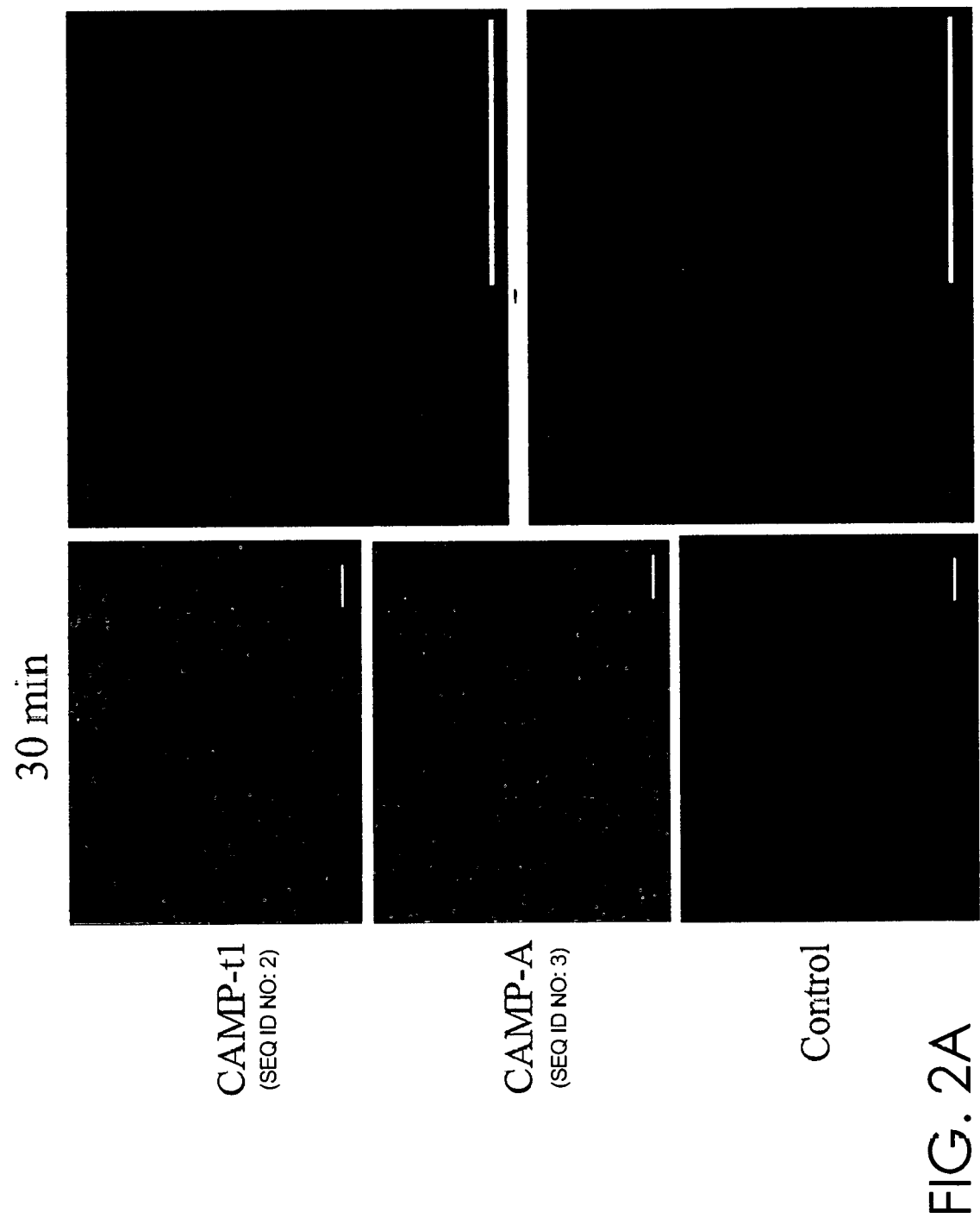
FIG. 2A is fluorescence microscopy image of membrane permeabilizing activity of CAMPs (SEQ ID NOs: 1, 2, 3, and 4) in bacteria treated with CAMPs (SEQ ID NOs: 1, 2, 3, and 4) and control bacteria, with enlargement, in accordance with an exemplary aspect of the present invention.
Figure 2B:
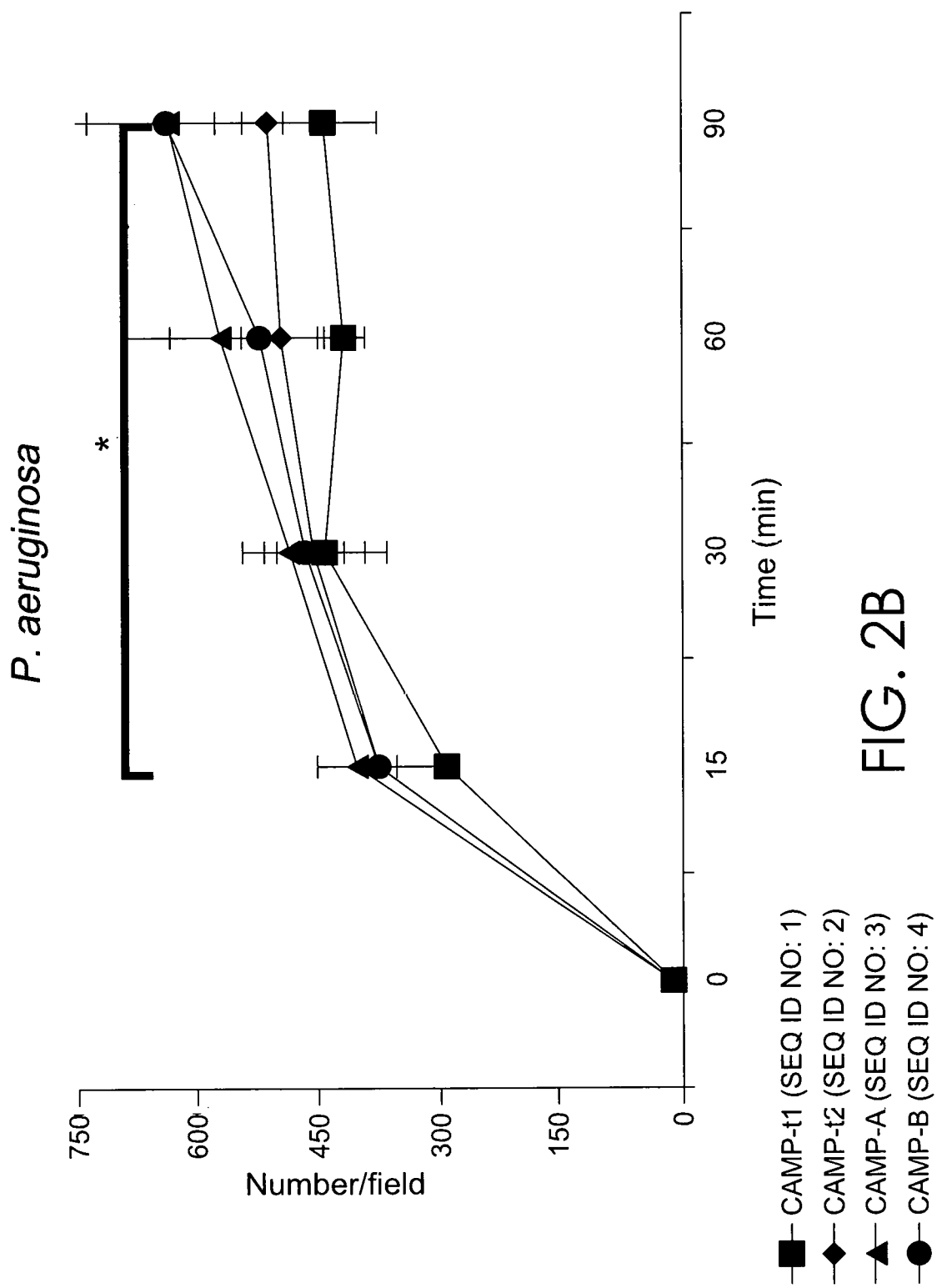
FIG. 2B is a plot of a number per field of positively stained *P. aeruginosa* at various times post treatment with CAMPs (SEQ ID NOs: 1, 2, 3, and 4), in accordance with an aspect of the present invention.
Figure 2C:
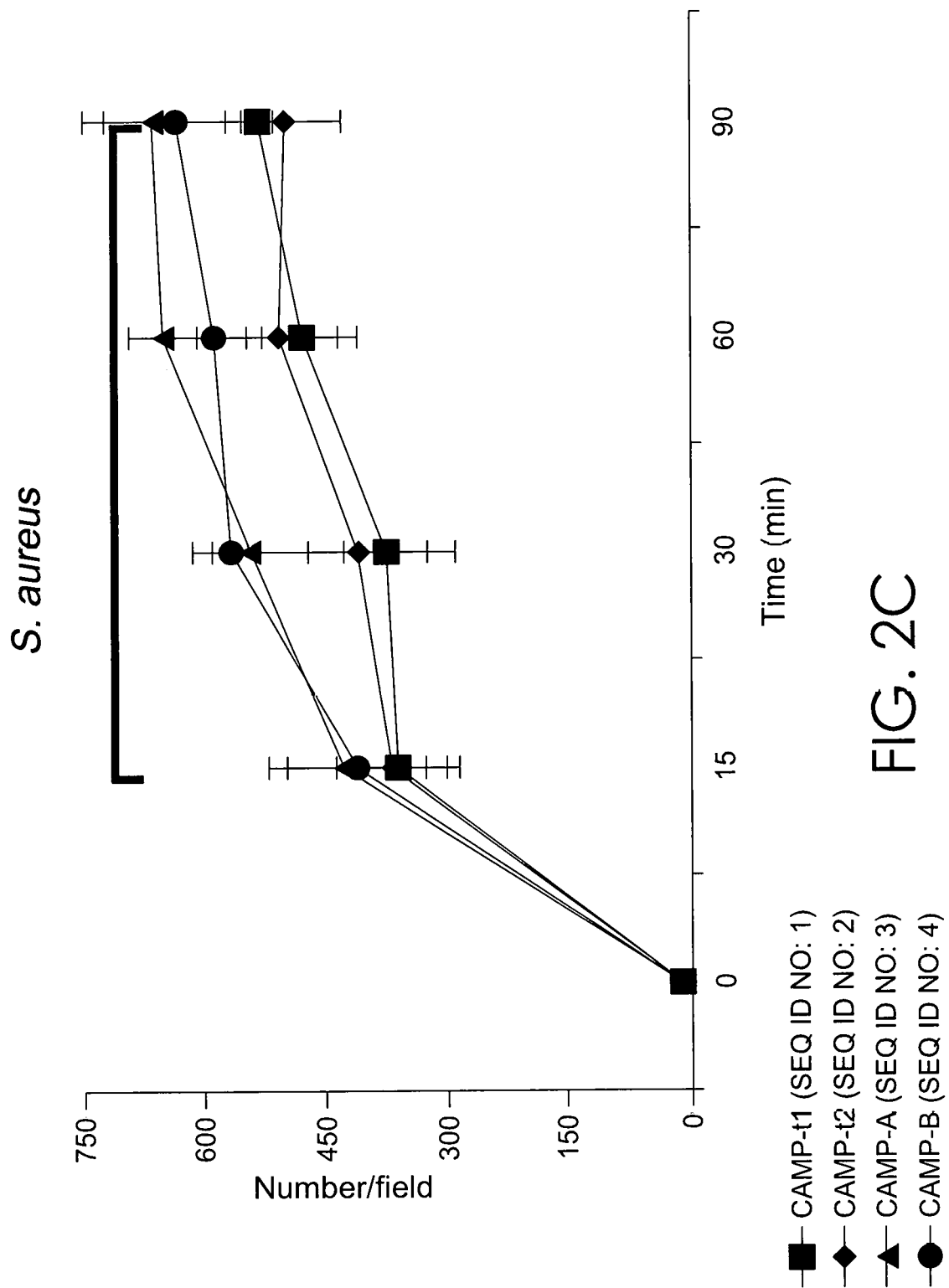
FIG. 2C is a plot of a number per field of positively stained of *S. aureus* at various times post treatment with CAMPs (SEQ ID NOs: 1, 2, 3, and 4), in accordance with an aspect of the present invention.
Figure 3A:
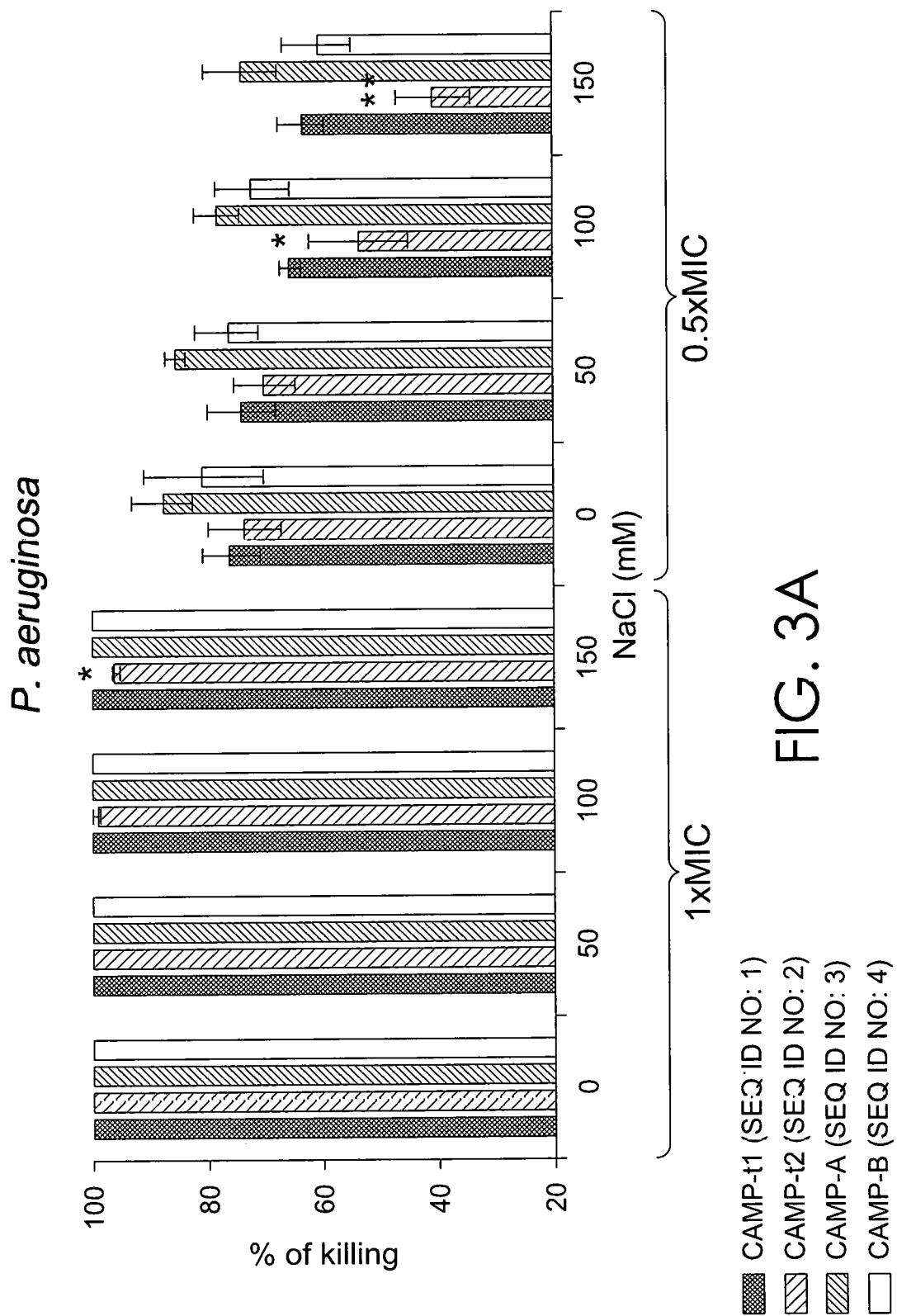
FIG. 3A is a bar graph showing the effect of salt on the antibacterial activity of CAMPs (SEQ ID NOs: 1, 2, 3, and 4) at 1×MIC and 0.5×MIC against *P. aeruginosa*, represented as a percent of killing at 0, 50, 100, and 150 mM NaCl, in accordance with an aspect of the present invention.
Figure 3B:
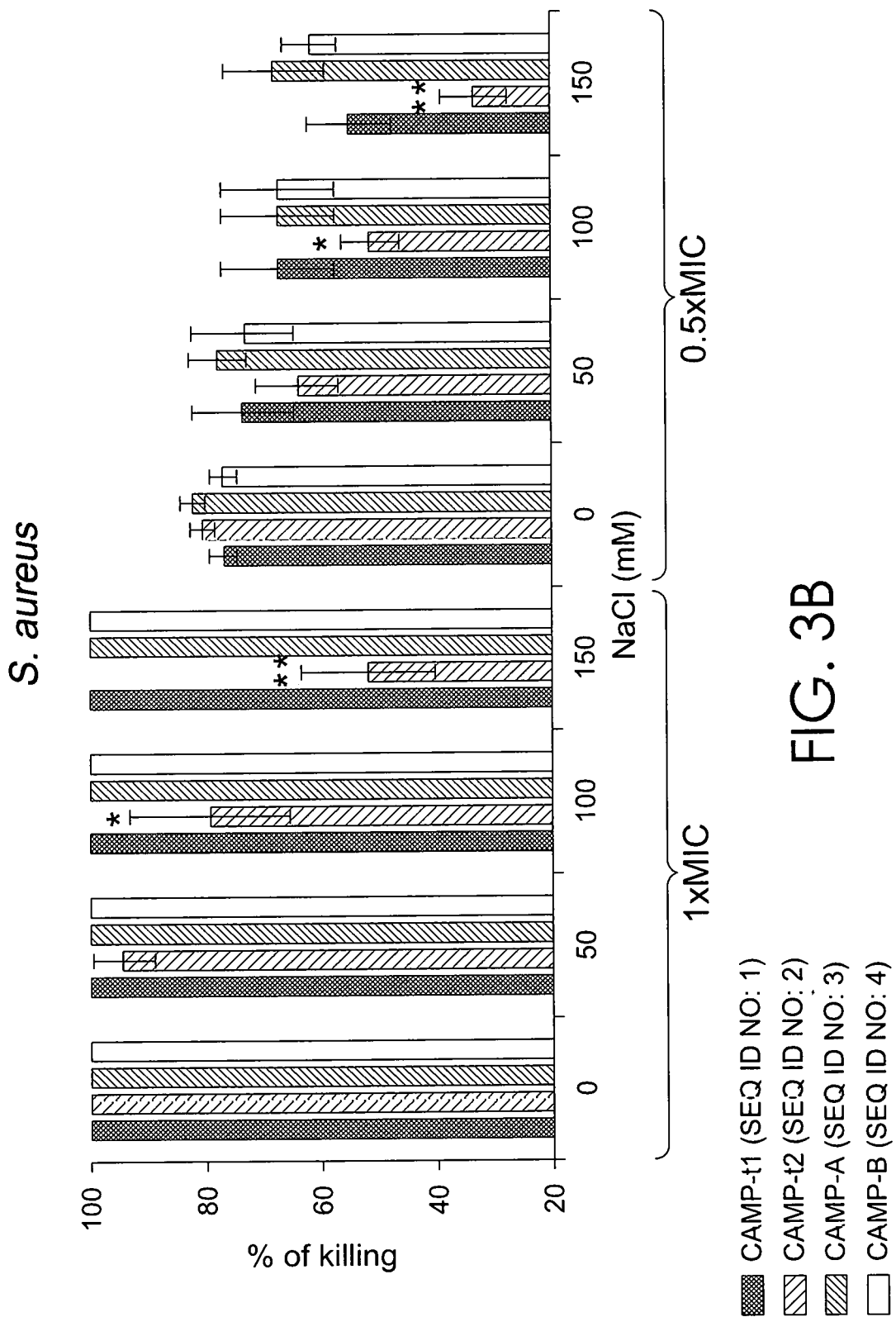
FIG. 3B is a bar graph showing the effect of salt on the antibacterial activity of CAMPs (SEQ ID NOs: 1, 2, 3, and 4) at 1×MIC and 0.5×MIC against *S. aureus*, represented as a percent of killing at 0, 50, 100, and 150 mM NaCl, in accordance with an aspect of the present invention.
Figure 3D:
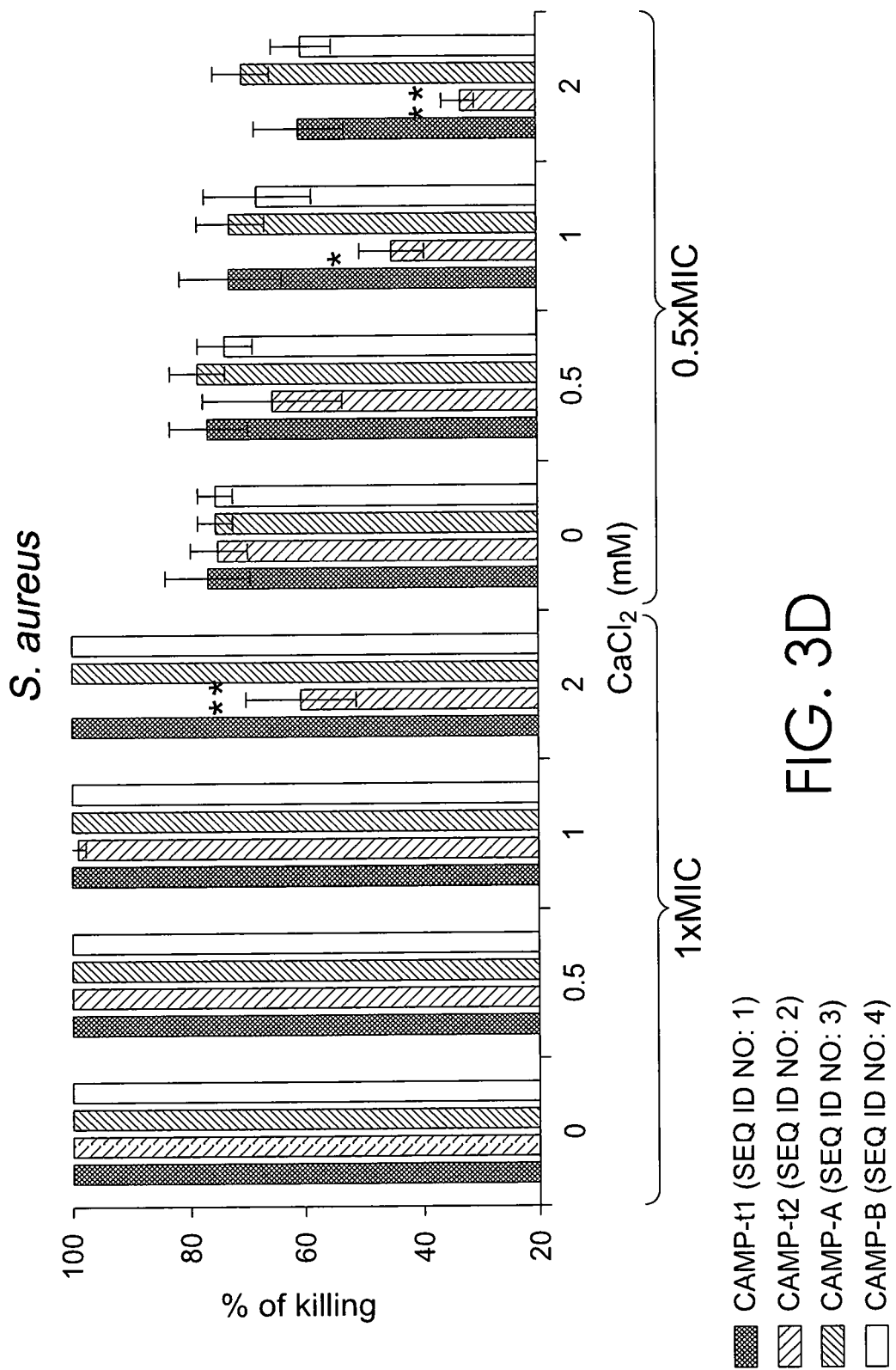
FIG. 3D is a bar graph showing the effect of salt on the antibacterial activity of CAMPs (SEQ ID NOs: 1, 2, 3, and 4) at 1×MIC and 0.5×MIC against *S. aureus*, represented as a percent of killing at 0, 0.5, 1, and 2 mM CaCl2, in accordance with an aspect of the present invention.

As shown in FIG. 2A, *P. aeruginosa* treated with CAMP-t1 (SEQ ID NO: 1) and CAMP-A (SEQ ID NO: 3) were stained red, indicating that bacterial membranes were damaged by these CAMPs (SEQ ID NOs: 1 and 3). In contrast, untreated bacteria did not show red fluorescence. When the permeabilizing ability was assessed based on the numbers of red cells per field, a time-dependent increase was observed from 15 to 90 minutes (FIGS. 2B and 2C). The number of red bacteria did not increase significantly after 30 minutes, indicating a fast-action mode of CAMPs (SEQ ID NOs: 1, 2, 3, and 4). Similar results were obtained for all CAMPs (SEQ ID NOs: 1, 2, 3, and 4) and both bacterial pathogens (FIG. 2B [*P. aeruginosa*] and FIG. 2C [*S. aureus*]).

Example One

Antimicrobial Activity Assay and Results

The minimum inhibitory concentrations (MICs) of CAMPs (SEQ ID NOs: 1, 2, 3, and 4) were determined according to the guidelines of the Clinical and Laboratory Standards Institute (CLSI). The Muller Hinton (MH) II broth used in MIC assay was supplemented with 20-25 mg/L of calcium and 10-12.5 mg/L of magnesium. In brief, peptides were two-fold serially diluted (2 to 256 μg/ml) in a 96-well microtiter plate (Nunc™, Thermo Fisher Scientific) and an equal volume (μl) of bacterial suspension was added to each well of the plate. The final bacterial concentration in the wells was $5 \times 10^5$ CFU/ml. The plate was incubated at 37° C. for 24 h, and the lowest concentration that completely inhibited visible bacterial growth was recorded. All assays were conducted in triplicate.

The Minimum Inhibitory Concentration(s) of the CAMPs (SEQ ID NOs: 1, 2, 3, and 4) against *P. aeruginosa* and *S. aureus* ATCC reference strains and multidrug-resistant *P. aeruginosa* and methicillin-resistant *S. pseudintermedius* (MRSP) strains were compared to that of AvBD-6 (SEQ ID NO: 13), having antimicrobial activity under low salt conditions (Table 2). CAMP-t1 (SEQ ID NO: 1) showed greater anti-*Pseudomonas* activity with MIC values 4-fold (for ATCC reference strain) and 2-fold (clinical isolates) lower than that of AvBD-6 (SEQ ID NO: 13). CAMP-t1 (SEQ ID NO: 1) showed greater antimicrobial activity against *S. aureus* ATCC reference strain (MIC was 4-fold lower than that of AvBD-6 [SEQ ID NO: 13]), but lesser improvements against MRSP clinical isolates as evidenced by its MIC values relative to AvBD-6 (SEQ ID NO: 13). CAMP-t2 (SEQ ID NO: 2) demonstrated excellent antimicrobial activity against *Pseudomonas* strains and *Staphylococcus* as well. The MICs of CAMP-t2 (SEQ ID NO: 2) against *S. aureus* and MRSP strains were up to 4-fold lower than that of AvBD-6 (SEQ ID NO: 13). Compared to CAMP-t2 (SEQ ID NO: 2), CAMP-A (SEQ ID NO: 3) exhibited higher hydrophobicity and higher antimicrobial activity against *P. aeruginosa* and *S. aureus* reference strains, multidrug resistant *P. aeruginosa* and MRSP clinical isolates. The MICs of CAMP-A (SEQ ID NO: 3) against *P. aeruginosa* and MRSP isolates were 4-fold to 32-fold lower than that of AvBD-6 (SEQ ID NO: 13). CAMP-B (SEQ ID NO: 4) also showed significantly improved antimicrobial activity against *P. aeruginosa* and *Staphylococcus* spp. The MICs of CAMP-B (SEQ ID NO: 4) against *Pseudomonas* spp. and methicillin resistant *S. pseudintermedius* were 2-fold to 3-fold higher than that of CAMP-A (SEQ ID NO: 3) (Table 2) (contd on next page).

TABLE 2

Minimum Inhibitory Concentrations (MIC)

| Bacteria (strain identification) | CAMP-t1 SEQ ID NO: 1 MIC (μg/ml) | CAMP-t2 SEQ ID NO: 2 MIC (μg/ml) | CAMP-A SEQ ID NO: 3 MIC (μg/ml) | CAMP-B SEQ ID NO: 4 MIC (μg/ml) | AvBD-6 SEQ ID NO: 13 MIC (μg/ml) |
|---|---|---|---|---|---|
| *P. aeruginosa* (ATCC 27853) | 64 | 64 | 16 | 32 | >256 |
| *P. aeruginosa* (1704173)[#] | 128 | 64 | 16 | 32 | >256 |
| *P. aeruginosa* (1703357)[#] | 128 | 128 | 16 | 64 | >256 |
| *P. aeruginosa* (1703511)[#] | 128 | 128 | 16 | 64 | >256 |
| *P. aeruginosa* (1703000)[#] | 128 | 64 | 8 | 32 | >256 |
| *P. aeruginosa* (1703002)[#] | 128 | 256 | 16 | 64 | >256 |
| *P. aeruginosa* (1703451)[#] | 128 | 64 | 16 | 64 | >256 |
| *P. aeruginosa* (1703949)[#] | 128 | 128 | 16 | 64 | >256 |
| *P. aeruginosa* (1703290)[#] | 128 | 128 | 16 | 64 | >256 |
| *P. aeruginosa* (1703983)[#] | 128 | 256 | 16 | 64 | >256 |
| *P. aeruginosa* (1704175)[#] | 128 | 64 | 16 | 32 | >256 |
| MIC$_{Average\ G-}$ | 122 ± 19[a] | 122 ± 73[a] | 15 ± 2[c] | 52 ± 16[b] | >256 |
| *S. aureus* (ATCC 29213) | 64 | 64 | 32 | 32 | 256 |
| *S. pseudintermedius*(13164006)* | 256 | 32 | 16 | 32 | >256 |
| *S. pseudintermedius*(13203008)* | 256 | 32 | 16 | 64 | 256 |
| *S. pseudintermedius*(13178007)* | 256 | 64 | 16 | 64 | 256 |
| *S. pseudintermedius*(13267017)* | 128 | 32 | 16 | 32 | >256 |
| *S. pseudintermedius*(13252001)* | 64 | 32 | 16 | 32 | 256 |
| *S. pseudintermedius*(13269013)* | 256 | 32 | 32 | 32 | >256 |
| *S. pseudintermedius*(13193006)* | 256 | 128 | 32 | 32 | >256 |
| *S. pseudintermedius*(13228005)* | 256 | 32 | 16 | 64 | >256 |
| *S. pseudintermedius*(13207007)* | 256 | 32 | 16 | 64 | >256 |
| *S. pseudintermedius*(13250111)* | 256 | 32 | 32 | 64 | 256 |
| MIC$_{Average\ G+}$ | 209 ± 81[a] | 47 ± 30[b] | 22 ± 8[c] | 47 ± 17[b] | ≥256 |

[#]Multidrug resistant clinical isolates of *P. aeruginosa* were resistant to chloramphenicol, tetracycline, sulfamethoxazole, and β-lactam antibiotics: amoxicillin, ampicillin and cefazolin.

*Methicillin-resistant *S. pseudintermedius* (MRSP).

Superscripts a, b, and c indicate significant difference ($p < 0.05$) in MICs among the four CAMPs (SEQ ID NOs: 1, 2, 3, and 4).

Example One

Salt Resistance Assay and Results

A major hindrance to clinical application of defensin peptides is the interference of function by cationic salts, often referred to as salt sensitivity. The effect of salt on antimicrobial activity of CAMPs (SEQ ID NOs: 1, 2, 3, and 4) against *P. aeruginosa* ATCC 27853 and *S. aureus* ATCC 29213 was determined by a colony count assay, in the presence of either 0, 50, 100, and 150 mM NaCl or 0, 0.5, 1, and 2 mM $CaCl_2$. In brief, bacterial colonies from an overnight culture plate were re-suspended in assay medium (10-fold diluted Mueller Hinton II broth) to obtain a final concentration of $2 \times 10^5$ CFU/ml. Twenty-five microliters of bacterial suspension and 25 µl of CAMP (SEQ ID NOs: 1, 2, 3, and 4) were mixed in the wells of a 96-well polypropylene microtiter plate (Nunc™, Thermo Fisher Scientific). Two peptide concentrations, 0.5×MIC and 1×MIC, were included in salt resistance assay and medium without CAMP (SEQ ID NOs: 1, 2, 3, and 4) served as a negative control. The bacteria-peptide mixtures were incubated at 37° C. for 2 hours, 10-fold serially diluted and plated on LB agar plates. The number of bacteria colonies was enumerated after 16 hours of incubation at 37° C. Antimicrobial activity was expressed as percent of killing using the following formula: $(CFU_{control} - CFU_{treated})/CFU_{control} \times 100\%$. All assays were performed in triplicate.

As shown in FIGS. 3A, 3B, 3C, and 3D, increasing NaCl and $CaCl_2$ concentrations had little to no impact, generally, on the bactericidal activity of CAMP-t1 (SEQ ID NO: 1), which is believed to exhibit a C-terminal poly-Trp tail. The bactericidal activity of CAMP-B (SEQ ID NO: 4), which is believed to lack a C-terminal poly-Trp tail, was somewhat impacted by the increased salt concentrations. At the physiological conditions of NaCl (100 to 150 mM) and $CaCl_2$ (1 to 2 mM), CAMP-t2 (SEQ ID NO: 2) retained approximately 40% of its killing activity against *P. aeruginosa* and *S. aureus*, compared to the results obtained at salt free conditions. The salt-resistance pattern of CAMP-t2 (SEQ ID NO: 2) was similar at two different peptide concentrations. Similar to CAMP-t1 (SEQ ID NO: 1), CAMP-A (SEQ ID NO: 3), and CAMP-B (SEQ ID NO: 4) with a Trp tail exhibited strong tolerance to NaCl and CaCl2 (FIGS. 3A, 3B, 3C, and 3D).

Example One

Hemolytic Assay and Cell Cytotoxicity Assay and Results

The Hemolytic Assay includes the following procedures. Briefly, mouse red blood cells (RBCs, Innovative research, Novi, Mich.) were washed three times with phosphate-buffered saline (PBS, pH 7.4), centrifuged at 1000×g for 10 minutes, and re-suspended in PBS to 10% (v/v). The RBCs were treated with CAMPs (SEQ ID NOs: 1, 2, 3, and 4) at various concentrations ranging from 4 to 512 µg/ml (2-fold serial dilutions) at 37° C. for 1 hours. PBS and 0.2% Triton X-100 were used as negative and positive controls, respectively. The supernatant was transferred to a 96-well flat-bottomed polystyrene plate (Thermo Fisher Scientific), and the amount of hemoglobin released into the supernatant was determined by measuring the absorbance with a spectrophotometer at 540 nm. Hemolytic activity was expressed as the percentage of hemolysis and calculated using the following equation: hemolysis $(\%) = (A_s - A0)/(A100 - A0) \times 100$, where $A_s$ is the absorbance of the sample, $A_{100}$ is the absorbance of completely lysed RBCs in 0.2% Triton X-100, and $A_0$ is the absorbance in the complete absence of hemolysis (PBS treatment). The assay was performed in triplicate. Therapeutic index (T.I.) was calculated according to a previously published formula: $T.I. = MHC/MIC_{GM}$. MHC was the minimum hemolytic concentration that caused 5% hemolysis of mouse RBCs. The $MIC_{GM}$ was the minimum inhibitory concentration of the peptide concentrations against bacterial growth after the geometric mean was calculated. $MI_{CG-}$ was the $MIC_{GM}$ for Gram-negative bacteria; $MIC_{G+}$ was the $MIC_{GM}$ for Gram-positive bacteria.

The Cell Cytotoxicity Assay includes the following procedures. Mouse immature dendritic cell line, JAWSII (ATCC CRL-11904™), was cultured in Alpha minimum essential medium with ribonucleosides, deoxyribonucleosides, 4 mM L-glutamine, 1 mM sodium pyruvate, and 5 ng/ml murine Granulocyte macrophage colony-stimulating factor (GM-CSF) then supplemented with 20% FBS, 100 U/ml penicillin, and 100 µg/ml streptomycin at 37° C. in humidified air with 5% CO2. CCR-2 transfected CHO-K1 cells were cultured in RPMI-1640 supplemented with 10% FBS, 2 mM L-glutamine, 100 units/ml penicillin and streptomycin, and 500 µg/ml G418 at 37° C. in humidified air with 5% CO2. The cytotoxicity of CAMPs (SEQ ID NOs: 1, 2, 3, and 4) to JASWII and CHO-K1 cells was determined using MTT (3-(4,5-dimethylthiazol-2-yl)-2,5-diphenyltetrazolium bromide, Thermo Fisher Scientific) cell proliferation assay. Cells ($5 \times 10^3$ cells/well) in 96-well microtiter plates were treated with peptides at 64, 128, 256, and 512 µg/ml for 4, 12, 24, and 48 hours at 37° C. After treatment, 20 µl of 12 mM MTT solution was added to each well and the plate was incubated for 4 hours. The medium in each well was replaced with 100 µl of dimethyl sulfoxide (DMSO, Sigma-Aldrich) to dissolve MTT crystals. The plates were read using a spectrophotometer at 540 nm. The viability of treated cells was expressed as the percentage of viability relative to the untreated control. The experiment was performed in triplicate.

Figure 4:
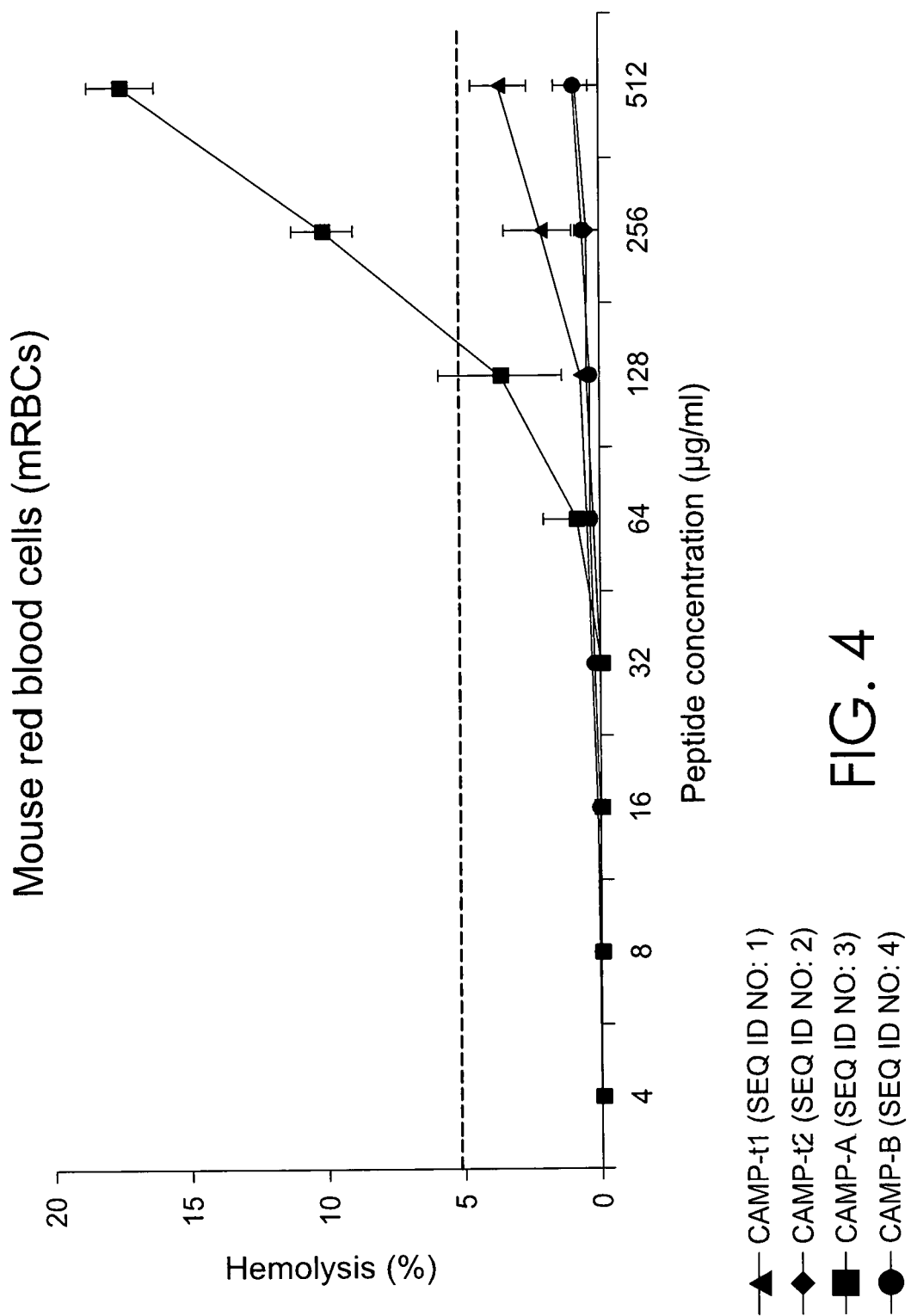
FIG. 4 is a graph showing a percentage of complete CAMP (SEQ ID NOs: 1, 2, 3, and 4) induced hemolysis of mouse red blood cells at various concentrations; in accordance with an aspect of the present invention.
Figure 5A:
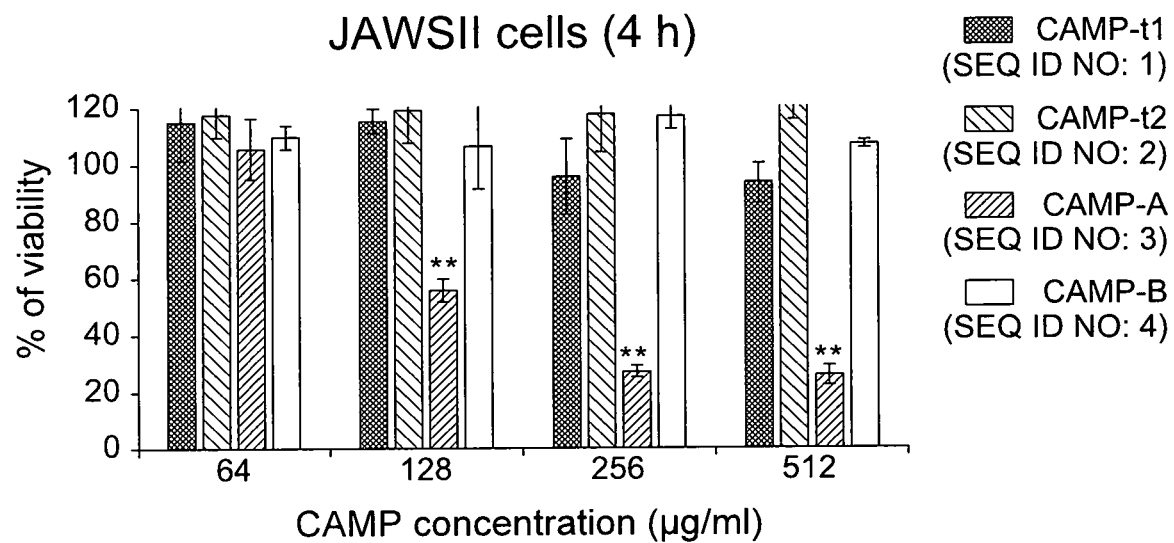
FIGS. 5A and 5C are bar graphs showing cytotoxicity effects of CAMPs (SEQ ID NOs: 1, 2, 3, and 4) on the viability of mouse immature dendritic JAWSII cells at 4 and 48 hours of incubation with peptide at the concentration of 64 to 512 µg/ml, represented as a percentage of viable cells relative to the untreated control cells, in accordance with an aspect of the present invention.
Figure 5B:
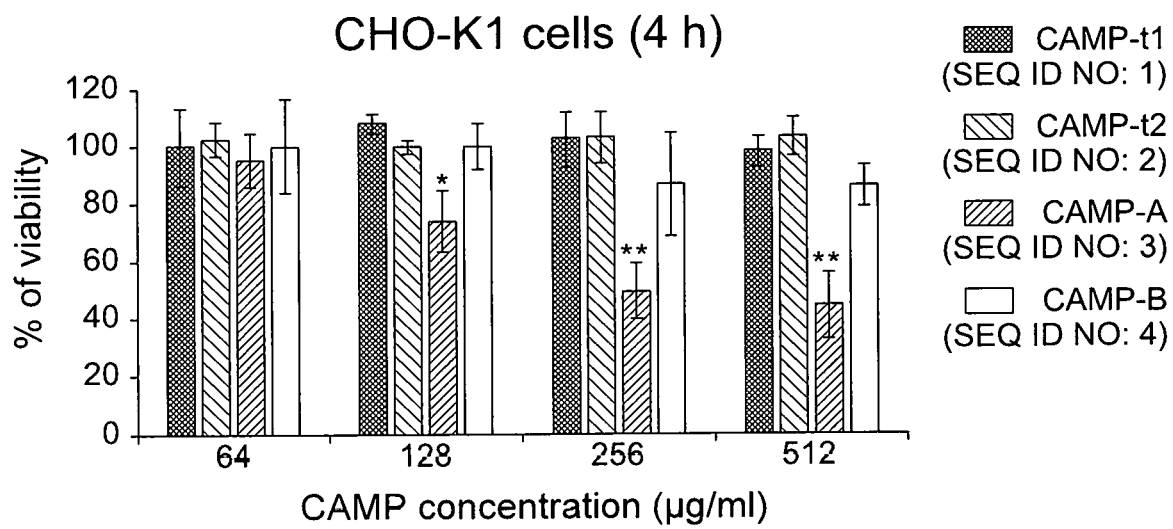
FIGS. 5B and 5D are bar graphs showing cytotoxicity effects of (SEQ ID NOs: 1, 2, 3, and 4) at 64 to 512 µg/ml on the viability of hamster ovary CHO-K1 cells at 4 and 48 hours of incubation with peptide at the concentration of 64 to 512 µg/ml, represented as a percentage of viable cells relative to the untreated control cells, in accordance with an aspect of the present invention.
Figure 5C:
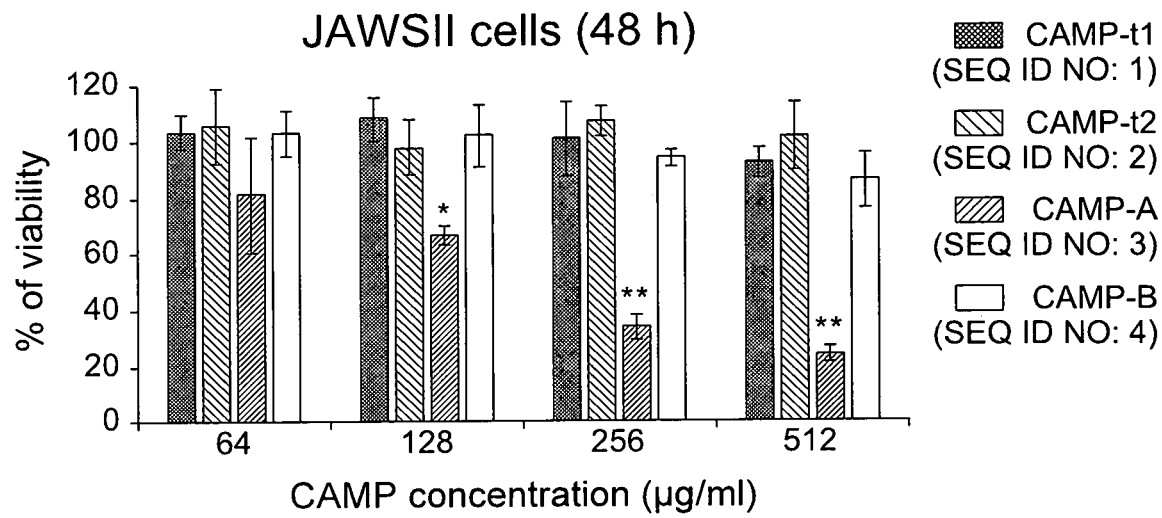
Figure 5D:
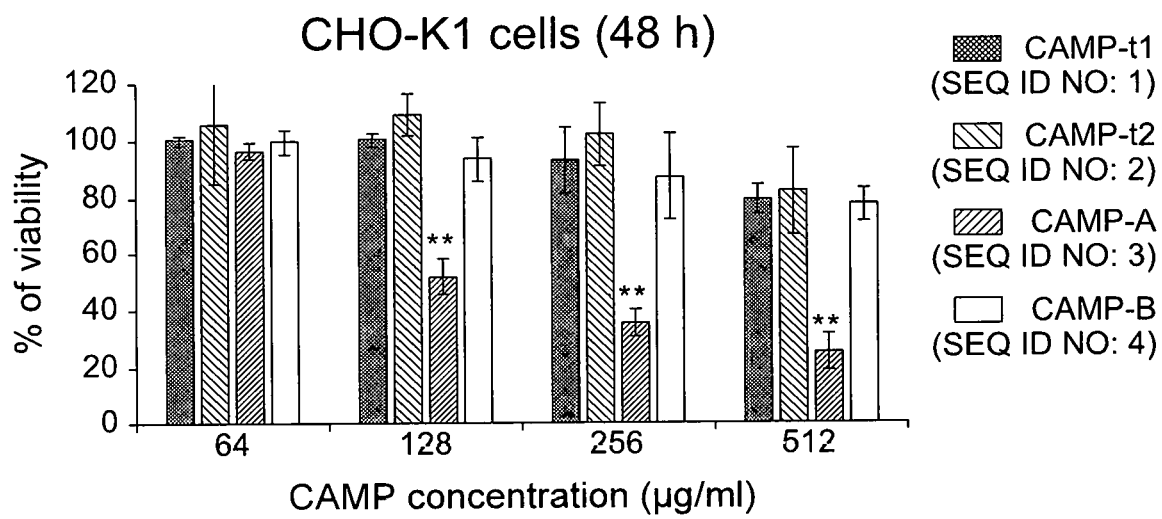

The results of the hemolytic activity of CAMPs (SEQ ID NOs: 1, 2, 3, and 4) to mouse RBCs is shown in FIG. 4. At high concentrations, CAMP-A (SEQ ID NO: 3) lysed approximately 3.6% of mRBCs at 128 m/ml, 10.1% of mRBCs at 256 µg/ml, and 17.5% of mRBCs at 512 µg/ml. CAMP-t1 (SEQ ID NO: 1), CAMP-t2 (SEQ ID NO: 2), and CAMP-B (SEQ ID NO: 4) cause about but generally no more than 5% of mRBCs to lyse at the polypeptide concentrations of 512 µg/ml. The minimum hemolytic concentration (MHC), geometric means of the MIC ($MIC_{GM}$), and therapeutic index (T.I.) were determined for each CAMP (SEQ ID NOs: 1, 2, 3, and 4) (Table 3). The average T.I. of CAMP-A (SEQ ID NO: 3) and CAMP-B (SEQ ID NO: 4) against *P. aeruginosa* were, generally, 8.72±2.41 and >10.90±4.0, respectively. The T.I. of CAMP-A (SEQ ID NO: 3) and CAMP-B (SEQ ID NO: 4) against *S. aureus* were 6.54±2.01 and >12.36±4.18, respectively.

TABLE 3

Therapeutic index of new antimicrobial peptides

| Peptides | CAMP-t1 SEQ ID NO: 1 | CAMP-t2 SEQ ID NO: 2 | CAMP-A SEQ ID NO: 3 | CAMP-B SEQ ID NO: 4 |
| --- | --- | --- | --- | --- |
| MHC | >512 | >512 | 128 | >512 |
| $MIC_{Average\ G-}$ | 122.18 ± 19.29 | 122.18 ± 72.71 | 15.27 ± 2.41 | 52.36 ± 16.14 |
| $MIC_{Average\ G+}$ | 209.45 ± 81.41 | 46.55 ± 29.89 | 21.82 ± 8.07 | 46.55 ± 16.71 |

TABLE 3-continued

Therapeutic index of new antimicrobial peptides

| Peptides | CAMP-t1<br>SEQ ID NO: 1 | CAMP-t2<br>SEQ ID NO: 2 | CAMP-A<br>SEQ ID NO: 3 | CAMP-B<br>SEQ ID NO: 4 |
|---|---|---|---|---|
| T.I. of G− | >4.36 ± 1.21 | >5.45 ± 2.54 | 8.72 ± 2.41 | >10.90 ± 4.0 |
| T.I. of G+ | >3.27 ± 2.41 | >13.45 ± 4.48 | 6.54 ± 2.01 | >12.36 ± 4.18 |

Therapeutic index (T.I.) is defined as the ratio of MHC to $MIC_{GM}$. MHC (µg/ml) is the minimum hemolytic concentration that caused about 5% hemolysis of mRBCs. The $MIC_{GM}$ (µg/ml) means the geometric mean (GM) of the MIC values of the peptides against bacteria. $MIC_{Average\ G-}$ is the $MIC_{GM}$ for Gram-negative bacteria. $MIC_{Average\ G+}$ is the $MIC_{GM}$ for Gram-positive bacteria.

Cell cytotoxicity data of the newly designed CAMPs (SEQ ID NOs: 1, 2, 3, and 4) is shown in FIGS. 5A, 5B, 5C, and 5D. Exposure of murine immature dendritic cell line JAWSII (FIGS. 5A and 5C) and CHO-K1 (FIGS. 5B and 5D) cells to CAMP-t1 (SEQ ID NO: 1), CAMP-t2 (SEQ ID NO: 2), and/or CAMP-B (SEQ ID NO: 4) at concentrations of 64, 128, 256, and 512 µg/ml for 4 to 48 hours did not significantly affect cell viability. The viability of both JAWSII and CHO-K1 cells was somewhat decreased by treatment with CAMP-A (SEQ ID NO: 3) at a concentration at about 128 µg/ml or greater. After treatment with CAMP-A (SEQ ID NO: 3), a significant difference in the percentage of cell viability was not observed between 4 hours treatment and 48 hours treatment.

Chemotaxis Assay and Results

Migration of JAWSII and CCR-2 transfected CHO-K1 cells in response to CAMPs (SEQ ID NOs: 1, 2, 3, and 4) was determined using a 48-well microchemotaxis chamber technique as previously described. Chemotaxis buffer (Minimum Essential Medium containing 0.1% BSA, 100 U/ml penicillin, and 100 µg/ml streptomycin) and bacterial peptide N-Formyl-methionyl-leucyl-phenylalanine (fMLF, Sigma-Aldrich) were included as negative and positive controls, respectively. The results were presented as chemotactic index (C.I.)=number of migrated cells induced by CAMPs (SEQ ID NOs: 1, 2, 3, and 4)/number of migrated cells induced by chemotactic buffer. The assay was repeated five times.

Figure 6A:
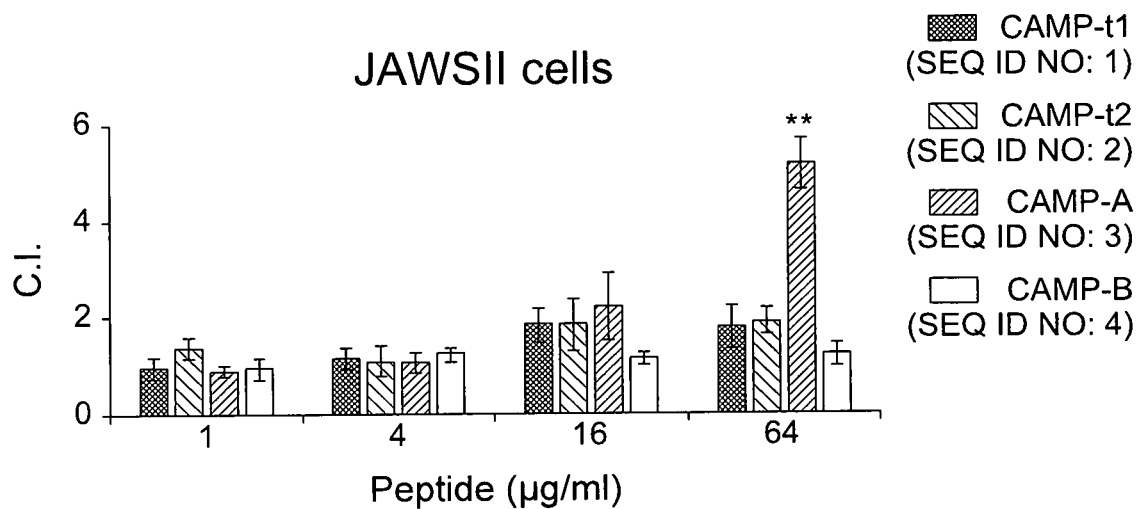
FIG. 6A is a bar graph showing chemotactic activity of mouse immature dendritic JAWSII cells induced by CAMPs (SEQ ID NOs: 1, 2, 3, and 4) at concentrations of 1, 4, 16, and 64 µg/ml, represented as a number of migrated cells induced by CAMP (SEQ ID NOs: 1, 2, 3, and 4) relative to a number of migrated cells in response to chemotactic buffer, in accordance with an aspect of the present invention.
Figure 6B:
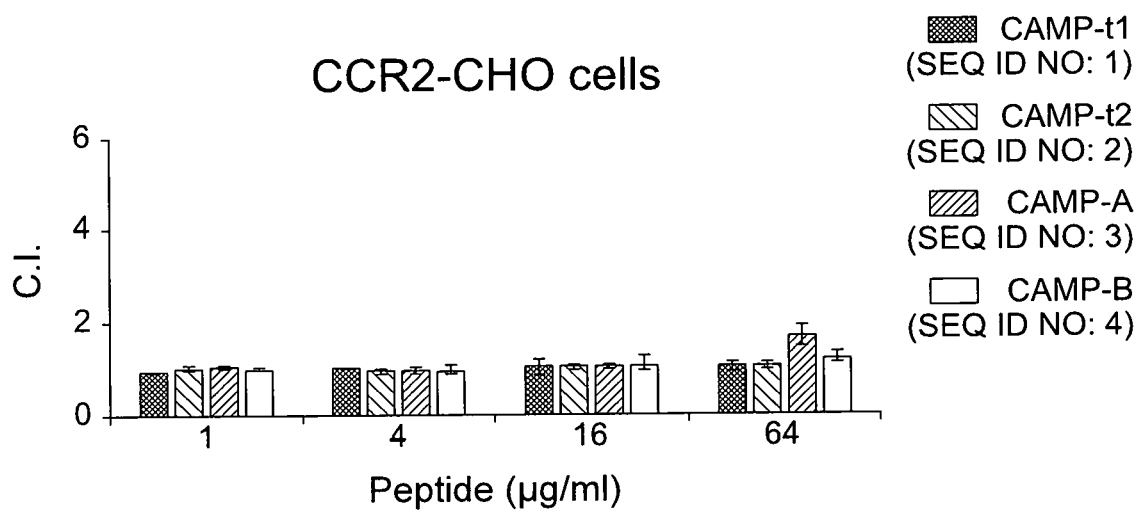
FIG. 6B is a bar graph showing chemotactic activity of CHO-K1 cells expressing avian CCR2 induced by CAMPs (SEQ ID NOs: 1, 2, 3, and 4) at concentrations of 1, 4, 16, and 64 µg/ml, represented as a number of migrated cells induced by CAMP (SEQ ID NOs: 1, 2, 3, and 4) relative to a number of migrated cells in response to chemotactic buffer, in accordance with an aspect of the present invention.
Figure 6C:
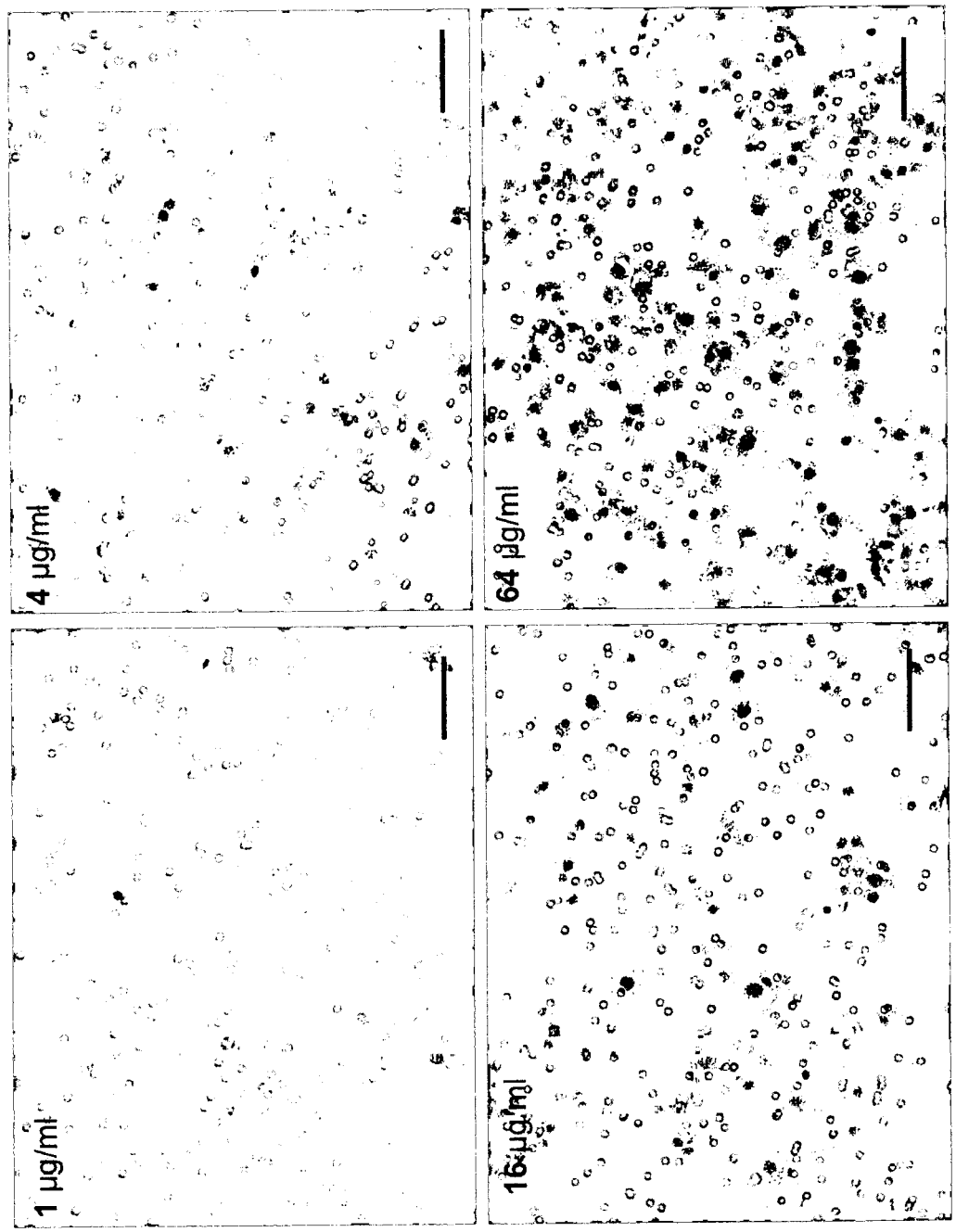
FIG. 6C is an image showing JAWSII cell migration induced by CAMP-A (SEQ ID NO: 3) with increasing peptide concentrations, ranging from 1 to 64 in accordance with an aspect of the present invention.

The chemotactic activity data of the CAMPs (SEQ ID NOs: 1, 2, 3, and 4) for JAWSII and CCR2-tranfected CHO-K1 cells is shown in FIG. 6A and FIG. 6B, respectively. The results indicated that CAMP-t1 (SEQ ID NO: 1), predicted to have an N-terminal helix-loop structure similar or the same as AvBD-12 (SEQ ID NO: 5), did not appear to produce chemotactic activity to either cell line (FIGS. 6A and 6B). CAMP-A (SEQ ID NO: 3), which exhibited excellent overall antimicrobial activity, showed mild chemotactic activity at a concentration of 64 µg/ml (C.I.=5.13; 77.5% of wild type AvBD-12 [SEQ ID NO: 5], C.I.=6.62) for JAWSII cells. As shown in FIG. 6C, JAWSII cell migration was induced by CAMP-A (SEQ ID NO: 3) with increasing peptide concentrations, ranging from 1 to 64 µg/ml. No significant chemotactic activity for CCR-2 transfected CHO-K1 cells was detected (FIG. 6B). CAMP-t2 (SEQ ID NO: 2) and CAMP-B (SEQ ID NO: 4) did not show appear to show any increased chemotactic activity for either JAWSII or CCR2-CHO-K1 cells.

Protease Resistance Assay and Results

Protease resistance was evaluated by using sodium dodecyl sulfate polyacrylamide gel electrophoresis (SDS-PAGE) followed by antimicrobial assays. CAMPs (SEQ ID NOs: 1, 2, 3, and 4) (10 µg) were treated with various proteases at various concentrations comparable to or higher than that found in host or bacterial culture, including 0.12, 0.6, and 1.2 µg/ml of α-chymotrypsin (Thermo Fisher Scientific), 0.4, 4.4, and 20 µg/ml of matrilysin (metalloproteinase-7, Sigma-Aldrich), 0.2, 2, and 20 µg/ml elastase (Thermo Fisher Scientific), or 0.2, 2, and 20 µg/ml of cathepsin B (Thermo Fisher Scientific). Protease digestion assay was carried out in 20 ml of digestion buffer (25 mM Tris and 150 mM NaCl, pH 7.8) for 1 hour at 37° C. After treatment, the digestion mixture was analyzed by SDS-PAGE on 16.5% polyacrylamide gel. To determine the effect of protease digestion on the antimicrobial activity of two most active CAMPs (SEQ ID NOs: 1, 2, 3, and 4), each peptide was first treated with a protease for 1 hour at 37° C. The mixture was then diluted to 1×MIC of the peptide and subjected to colony count assay as described above. Assay buffer containing protease but not peptide and buffer containing untreated peptide were included as controls. Protease inhibition of antimicrobial activity of CAMPs (SEQ ID NO: 1, 2, 3, and 4) was expressed as percentage of killing by protease treated peptide in relevance to untreated peptide. The experiment was repeated three times with triplicate in each assay.

Figure 7A:
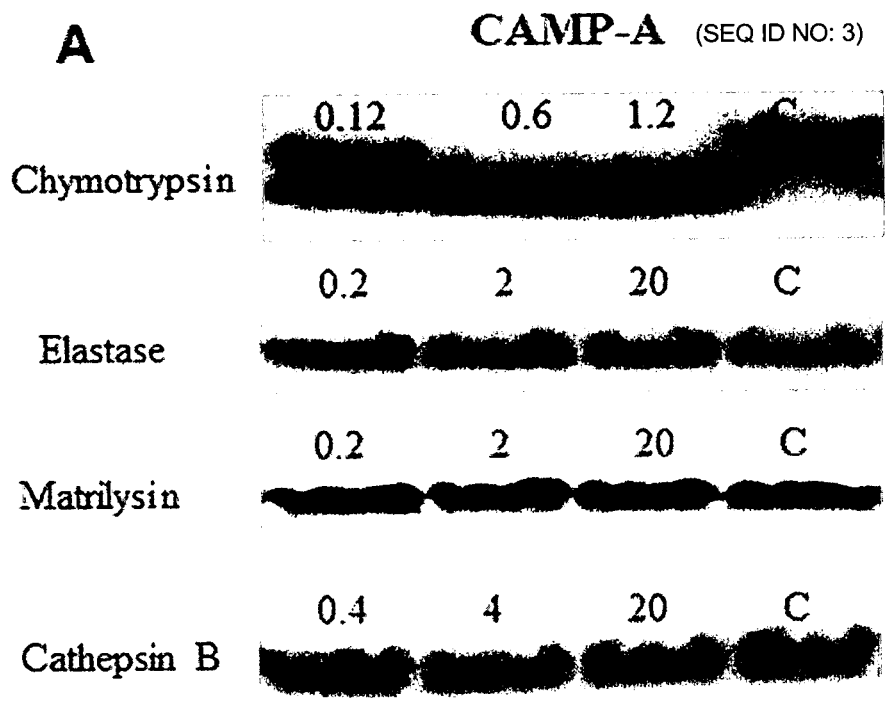
FIG. 7A is and SDS-PAGE showing the effects of protease treatments of α-chymotrypsin, elastase, matrilysin, and cathepsin on antimicrobial activity of CAMP-A (SEQ ID NO: 3) against *P. aeruginosa* and *S. aureus*, expressed as percent killing by digested peptides over untreated peptides, in accordance with an aspect of the present invention.
Figure 7B:
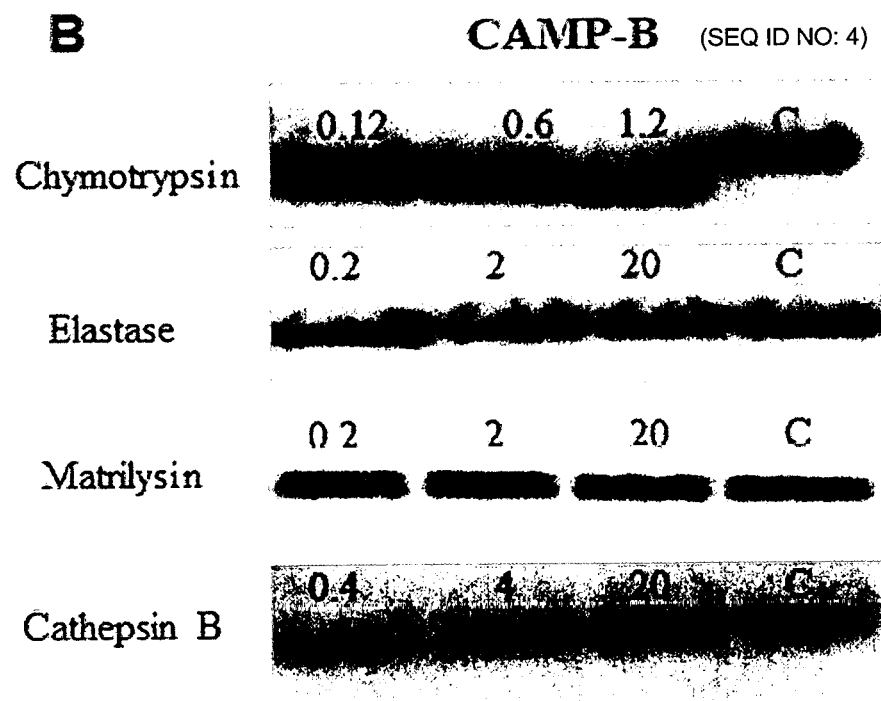
FIG. 7B is and SDS-PAGE showing effects of protease treatments of α-chymotrypsin, elastase, matrilysin, and cathepsin on antimicrobial activity of CAMP-B (SEQ ID NO: 4) against *P. aeruginosa* and *S. aureus*, expressed as percent killing by digested peptides over untreated peptides, in accordance with an aspect of the present invention.
Figure 7C:
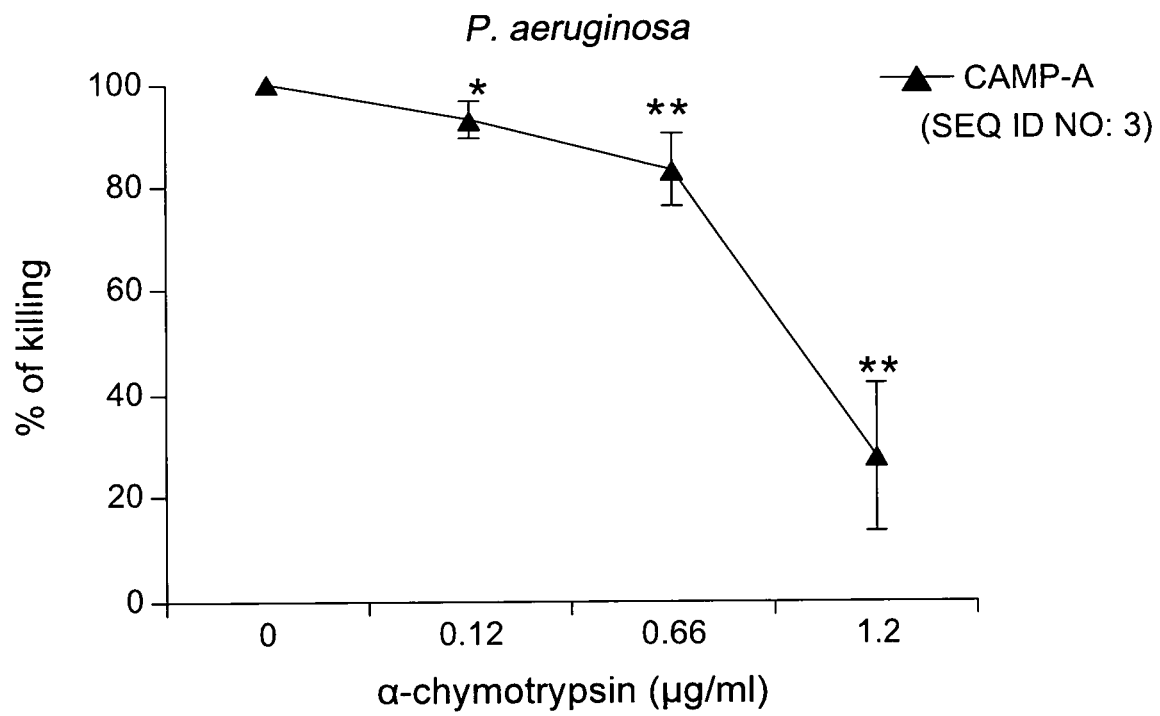
FIG. 7C is a graph showing the antimicrobial activity of CAMP-A (SEQ ID NO: 3) and CAMP-B (SEQ ID NO: 4) against *P. aeruginosa* post-digestion by α-chymotrypsin at the concentration of 0.12, 0.66, and 1.2 µg/ml, in accordance with an aspect of the present invention.
Figure 7C:
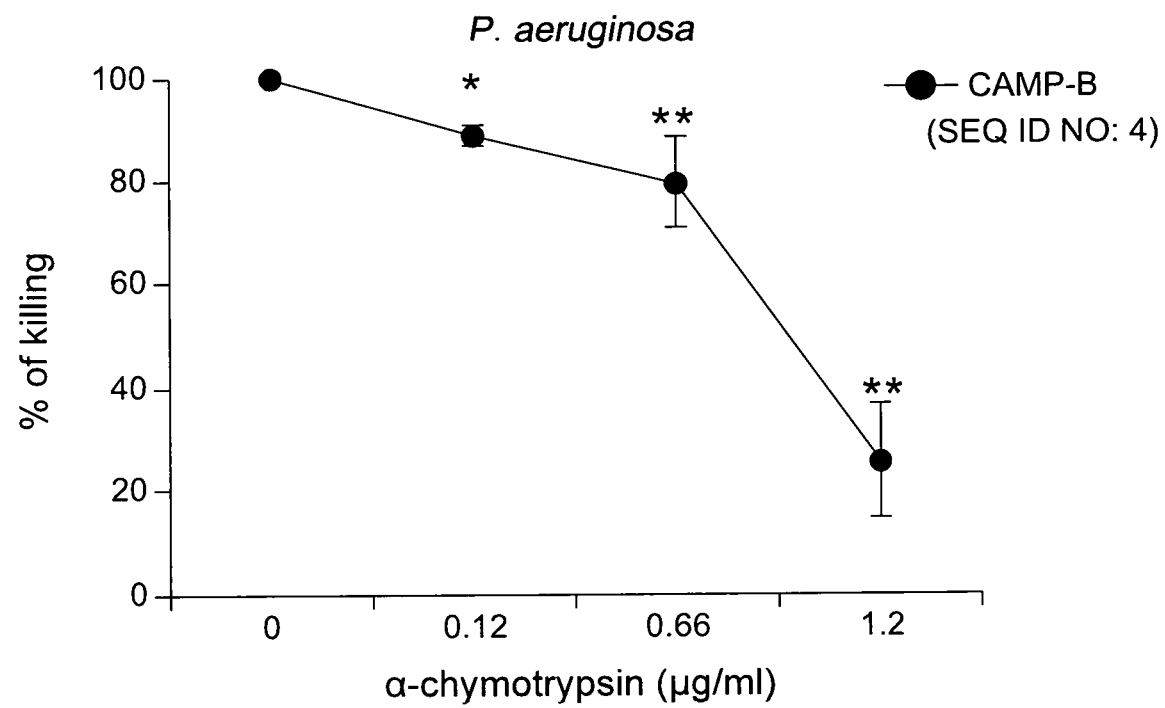
Figure 7D:
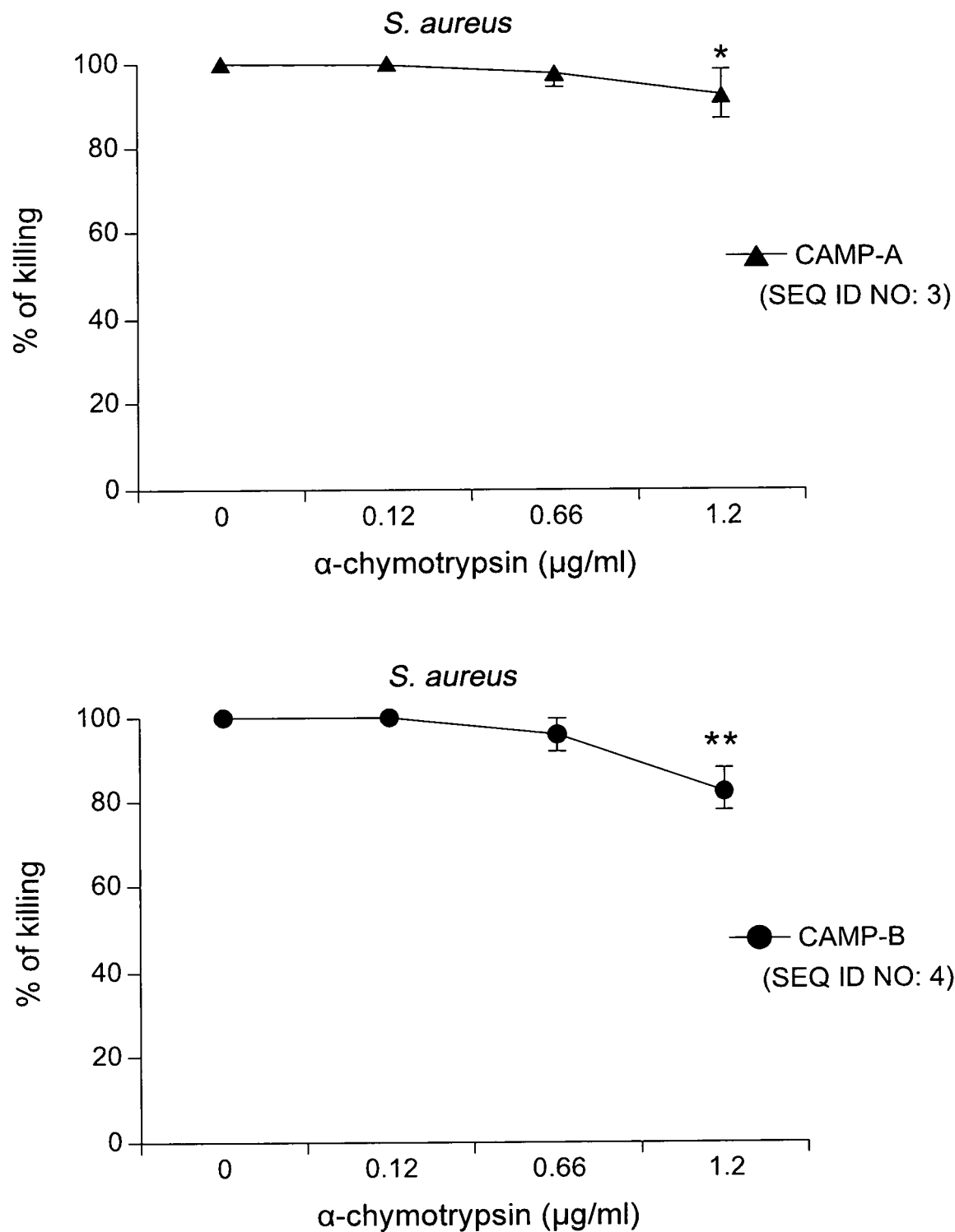
FIG. 7D is a graph showing antimicrobial activity of CAMP-A (SEQ ID NO: 3) and CAMP-B (SEQ ID NO: 4) against *S. aureus* post-digestion by α-chymotrypsin at the concentration of 0.12, 0.66, and 1.2 µg/ml, in accordance with an aspect of the present invention.

The resistance of CAMP-A (SEQ ID NO: 3) and CAMP-B (SEQ ID NO: 4), two peptides exhibiting strong antimicrobial activity and salt-resistance, to various proteases is shown in the data of FIGS. 7A-7D. The results indicated that CAMP-A (SEQ ID NO: 3) and CAMP-B (SEQ ID NO: 4) were partially digested by α-chymotrypsin at protease concentrations of 0.12 to 1.2 µg/ml, as indicated by the presence of peptide bands with lower molecular weight than that of the untreated peptides (FIGS. 7A and 7B). The antimicrobial activity of CAMP-A (SEQ ID NO: 3) and CAMP-B (SEQ ID NO: 4) against *P. aeruginosa* appeared to decrease after digestion (FIG. 7C). The digested peptides retained, about 90% (at 0.12 µg/ml), 80% (at 0.66 µg/ml), and 30% (at 1.2 µg/ml) of the killing activity of the untreated CAMP-A (SEQ ID NO: 3) or CAMP-B (SEQ ID NO: 4). Anti-*Staphylococcus* activity was mildly affected only when the CAMP-A (SEQ ID NO: 3) and CAMP-B (SEQ ID NO: 4) were treated with the highest concentration (1.2 µg/ml) of α-chymotrypsin (FIG. 7D). CAMP-A (SEQ ID NO: 3) and CAMP-B (SEQ ID NO: 4) did not appear to be cleaved by metalloproteinases matrilysin, elastase, and cathepsin B at protease concentrations up to 20 µg/ml. Treatment with these proteases did not affect the antimicrobial activity of CAMP-A (SEQ ID NO: 3) and CAMP-B (SEQ ID NO: 4) (data not shown).

Example Two

Properties of Antimicrobial Agents Comprising a Longer Polypeptide, or a Peptidomimetic of the Polypeptide To demonstrate the accuracy in which the peptides were selected and identified, descriptions of experiments that were conducted and their respective results are provided herein. Experiments were conducted to illustrate the properties robust antimicrobial activity, improved salt resistance, increased protease resistance, and reduced cytotoxicity regarding peptides, said peptides including the amino acid sequences of SEQ ID NOs: 5, 6, 7, and 8.

Statistical analysis on some or all of the data in Example Two may include the following. Data were presented as the means±standard deviation (SD). Differences between groups were analyzed by student's t-test or one-way analysis of variance (ANOVA) followed by Duncan's test for multiple comparisons using software SPSS version 19.0 (IBM Corp., Armonk, N.Y.). Differences at p<0.05 level were considered statistically significant, and at p<0.01 level were considered extremely significant.

Example Two

Design and Synthesis of Antimicrobial Agent

The three dimensional structures of AvBDs (SEQ ID NOs: 5, 6, 7, 8, 9, 10, 11, 12, AND 13) were predicted by using the 1-TASSER program (http://zhanglab.ccmb.med.u-mich.eduii-TASSER). The distribution of positively charged amino acids were evaluated using PyMOL (https://www.pymol.org/). Group 1 analogues, including AvBD-12A1 (SEQ ID NO: 6), AvBD-12A2 (SEQ ID NO: 7) and AvBD-12A3 (SEQ ID NO: 8), were predicted to be linear peptides, in which the six cysteines ($C^1C^2C^3C^4C^5C^6$ or C5C12C17C27C34C35) were replaced with structurally similar amino acid residues (alanine and serine) as follows: AvBD-12A1 (SEQ ID NO: 6): A5A12A17A27A34A35, AvBD-12A2 (SEQ ID NO: 7) S5S12S17A27A34A35, and AvBD-12A3 (SEQ ID NO: 8): A5A12A17S27S34S35. Additional modifications were introduced to these analogues to alter peptide hydrophobicity and charge. In AvBD-12A1 (SEQ ID NO: 6), four negatively charged amino acid residues (D3D8E21E29) were replaced with one polar and three hydrophobic amino acid residues (H3V8L21E29). In AvBD-12A2 (SEQ ID NO: 7) and AvBD-12A3 (SEQ ID NO: 8), D3D8E21E29 were substituted with positively charged residues R3K8K21R29. Group 2 analogues, including AvBD-12A4 (SEQ ID NO: 9), AvBD-12A5 (SEQ ID NO: 10) and AvBD-12A6 (SEQ ID NO: 11), exhibited a reduced number of disulfide bridges. To remove disulfide bridges, the cysteine residues ($C^1C^2C^3C^4C^5C^6$ or C5C12C17C27C34C35) of AvBD-12 (SEQ ID NO: 5) were replaced with isosteric a-aminobutyric acids (Abu, U) to create AvBD-12A4 (SEQ ID NO: 9) (U5C12C17C27U34C35), AvBD-12A5 (SEQ ID NO: 10) (U5U12C17U27U34C35), and AvBD-12A6 (SEQ ID NO: 13) (U5U12U17U27U34U35), for example. Group 3 analogues included a hybrid polypeptide, AvBD-12/6 (SEQ ID NO: 12). The hybrid analogue was designed using the backbone of AvBD-12 (SEQ ID NO: 5), in which the negatively charged amino acid residues (D3D8E21E29) of AvBD-12 (SEQ ID NO: 5) were replaced with amino acids (H3Q8Y21S29) of AvBD-6 (SEQ ID NO: 13) at the corresponding positions. The hydrophobicity and charge of the analogues at neutral pH were calculated using Peptide 2.0 (http://peptide2.com) and Peptide property calculator (PepCalc.com), respectively.

All peptides were custom synthesized using a solid phase 9-fluorenylmethoxycarbonyl (Fmoc) method and purified by reversed-phase high performance liquid chromatography (RP-HPLC) (Lifetein, Hillsborough, N.J.). The analogues AvBD-12A4 (SEQ ID NO: 9), AvBD-12A5 (SEQ ID NO: 10), AvBD-12/6 (SEQ ID NO: 12), AvBD-6 (SEQ ID NO: 13) and AvBD-12 (SEQ ID NO: 5) with varying numbers of cysteine residues were subjected to oxidative folding as described previously. Electrospray ionization mass spectrometry (ESI-MS) was performed to confirm the correct formation of disulfide bridges between $Cys^1$-$Cys^5$ $Cys^2$-$Cys^4$ and $Cys^3$-$Cys^6$. The purity of the synthetic analogues was about or more than 98.5%, as verified by liquid chromatography-mass spectrometry (LC-MS) (Lifetein, Hillsborough, N.J.).

Substitutions of $C^1C^2C^3C^4C^5C^6$ (or C5C12C17C27C34C35) by A5A12A17A27A34A35 (AvBD-12A1 [SEQ ID NO: 6]) is believed to have eliminated three disulfide bridges and elevated hydrophobicity from 33% (AvBD-12 [SEQ ID NO: 5]) to 47%. Additionally, H3V8L21I29 for D3D8E21E29 substitutions increased hydrophobicity to 53% and net positive charge from +1 (AvBD-12 [SEQ ID NO: 5]) to +5 (AvBD-12A1 [SEQ ID NO: 6]). Changes from $C^1C^2C^3C^4C^5C^6$ to S5S12S17A27A34A35 (AvBD-12A2 [SEQ ID NO: 7]) or A5A12A17S27S34S35 (AvBD-12A3 [SEQ ID NO: 8]) and D3D8E21E29 to R3K8K21R29 (AvBD-12A2 [SEQ ID NO: 7] and AvBD-12A3 [SEQ ID NO: 8]) is believed to have eliminated all three disulfide bridges and increased hydrophobicity from 33% to 40% and net positive charge from +1 to +9. It is predicted that AvBD-12A4 (SEQ ID NO: 9), AvBD-12A5 (SEQ ID NO: 10), and AvBD-12A6 (SEQ ID NO: 11) lost disulfide bridge(s) $C^{1-5}$; $C^{1-5}$ and $C^{2-4}$; $C^{1-5}$, $C^{2-4}$, and $C^{3-6}$; respectively. The C to U changes are not believed to have affected hydrophobicity and/or net charge. The hybrid AvBD-12/6 (SEQ ID NO: 13), having a backbone of AvBD-12 (SEQ ID NO: 5) and positively charged amino acids (H3Q8Y21S29) of AvBD-6 (SEQ ID NO: 13), appeared to retain the parent peptides' hydrophobicity (33%) and a net charge (+5), relative to the parent peptides AvBD-6 (SEQ ID NO: 13) (+7) and AvBD-12 (SEQ ID NO: 5) (+1). The sequence, charge, hydrophobicity, and/or number of disulfide bridges of the peptides and AvBD-12 (SEQ ID NO: 5) and AvBD-6 (SEQ ID NO: 13) are listed in Table 4:

TABLE 4

Amino acid sequences

| Defensin | Amino acid sequence [a, b, c] | Charge | # of S-S bonds | Hydrophobicity |
|---|---|---|---|---|
| AvBD-12 SEQ ID NO: 5 | GPDSC$^1$NHDRGLC$^2$RVGNC$^3$NPGEYL AKYC$^4$FEPVILC$^5$C$^6$KPLSPTPTKT | +1 | 3 | 33% |
| AvBD-12-A1 SEQ ID NO: 6 | GPHSA NHVRGLA RVGNA NPGLYLAKYA FIPVILA A KPLSPTPTKT | +5 | 0 | 53% |

TABLE 4 -continued

Amino acid sequences

| Defensin | Amino acid sequence [a, b, c] | Charge | # of S-S bonds | Hydrophobicity |
|---|---|---|---|---|
| AvBD-12-A2 SEQ ID NO: 7 | GPRSS NHKRGLS RVGNS NPGKYLAKYA FRPVILA A KPLSPTPTKT | +9 | 0 | 40% |
| AvBD-12-A3 SEQ ID NO: 8 | GPRSA NHKRGLA RVGNA NPGKYLAKYS FRPVILS S KPLSPTPTKT | +9 | 0 | 40% |
| AvBD-12-A4 SEQ ID NO: 9 | GPDSU NHDRGLC$^2$RVGNC$^3$NPGEYLAKYC$^4$ FEPVILU C$^6$KPLSPTPTKT | +1 | 2 | 33% |
| AvBD-12-A5 SEQ ID NO: 10 | GPDSU NHDRGLU$^2$RVGNC$^3$NPGEYLAKYU FEPVILU C$^6$KPLSPTPTKT | +1 | 1 | 33% |
| AvBD-12-A6 SEQ ID NO: 11 | GPDSU NHDRGLU RVGNU NPGEYLAKYU FEPVILU U KPLSPTPTKT | +1 | 0 | 33% |
| AvBD-12/6 SEQ ID NO: 12 | GPHSC$^1$NHQRGLC$^2$RVGNC$^3$NPGYYLAKYC$^4$ FSPVILC$^5$C$^6$KPLSPTPTKT | +5 | 3 | 33% |
| AvBD-6 SEQ ID NO: 13 | SPIHAC$^1$RYQRGVC$^2$1PGPC$^3$RVVPYYRVG SC$^4$GSGLKSC$^5$C$^6$VRNRWA | +7 | 3 | 33% |

[a] Disulfide bridges (S-S) between C$^{1-5}$, C$^{2-4}$, C$^{3-6}$.
[b] U: α-aminobutyric acid.
[c] Acidic amino acids, basic amino acids, and cysteines are highlighted in blue, red, and green color, respectively. C$^1$C$^2$C$^3$C4$^6$ or C5 C12 C17 C27 C34 C35.

Figure 8A:
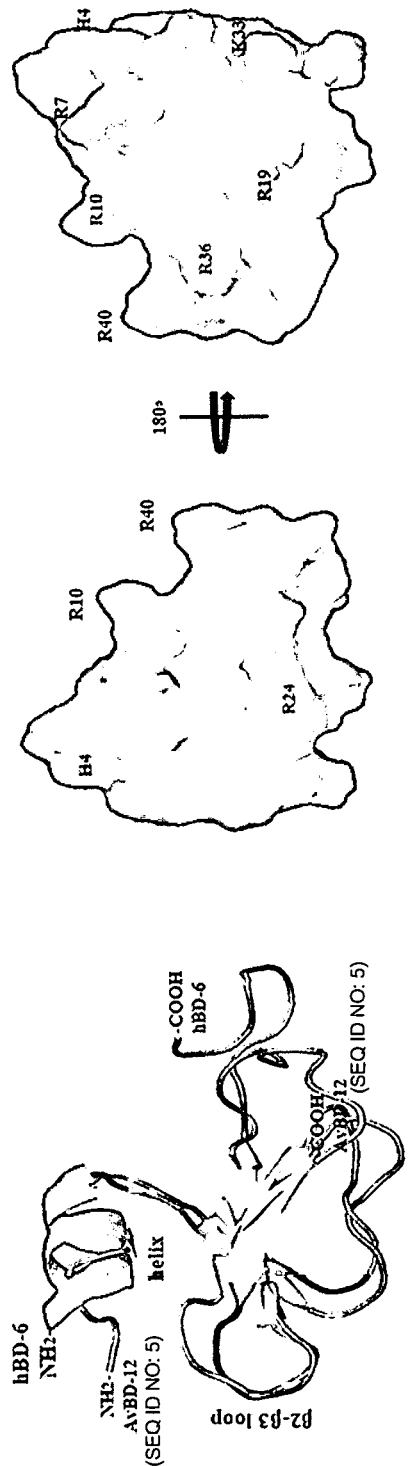
FIG. 8A shows I-TASSER predicted three dimensional structures of AvBD-12 (SEQ ID NO: 5) and hBD-6, superimposed, and the distribution of positively and negatively charged amino acid residues, in accordance with an aspect of the present invention.
Figure 8B:
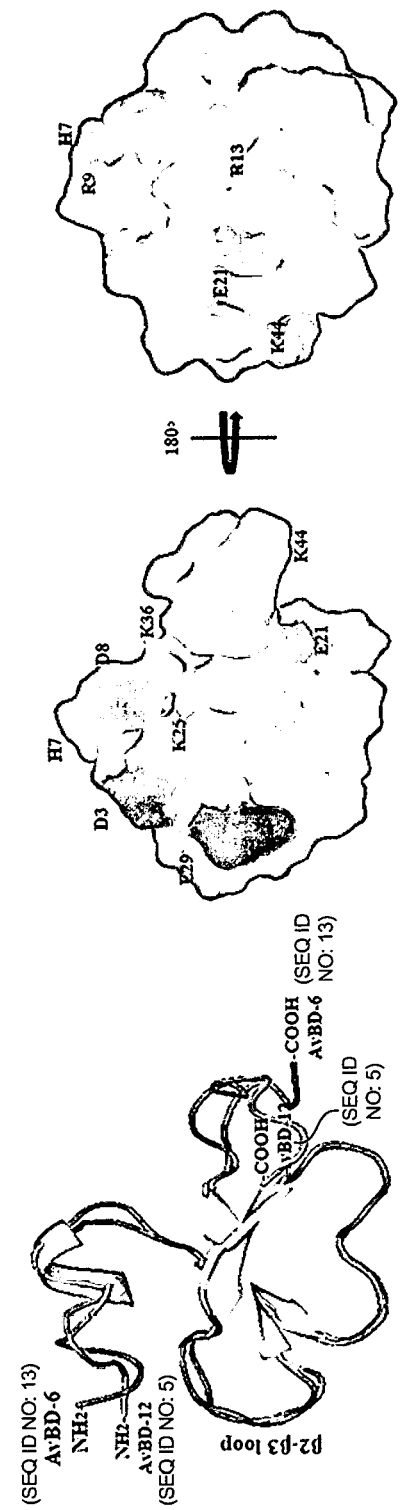
FIG. 8B shows I-TASSER predicted three dimensional structures of AvBD-12 SEQ ID NO: 5) and AvBD-6 (SEQ ID NO: 13), superimposed, and the distribution of positively charged, wherein basic and acidic amino acids are highlighted in red and blue, respectively, in accordance with an aspect of the present invention.
Figure 9B:
FIG. 9B shows an enlarged view of the P2-P3 loop in AvBD-12A2 (SEQ ID NO: 7) wherein the hydrogen bond between the —C═O group of F28 main chain and the —NH group of R29 side chain causes the arginine residue folding back, in accordance with an aspect of the present invention.
Figure 9C:
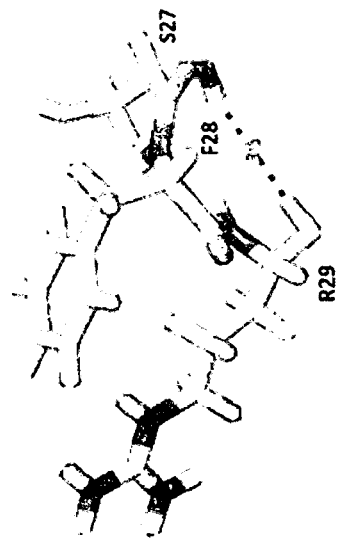
FIG. 9C shows an enlarged view of the P2-P3 loop in AvBD-12A3 (SEQ ID NO: 8) wherein the CHO interactions between S27-OH groups and the —CH groups on the aromatic ring of F28 result in an outward protrusion of R29 and a parallel twist of F28 aromatic ring, in accordance with an aspect of the present invention.
Figure 9A:
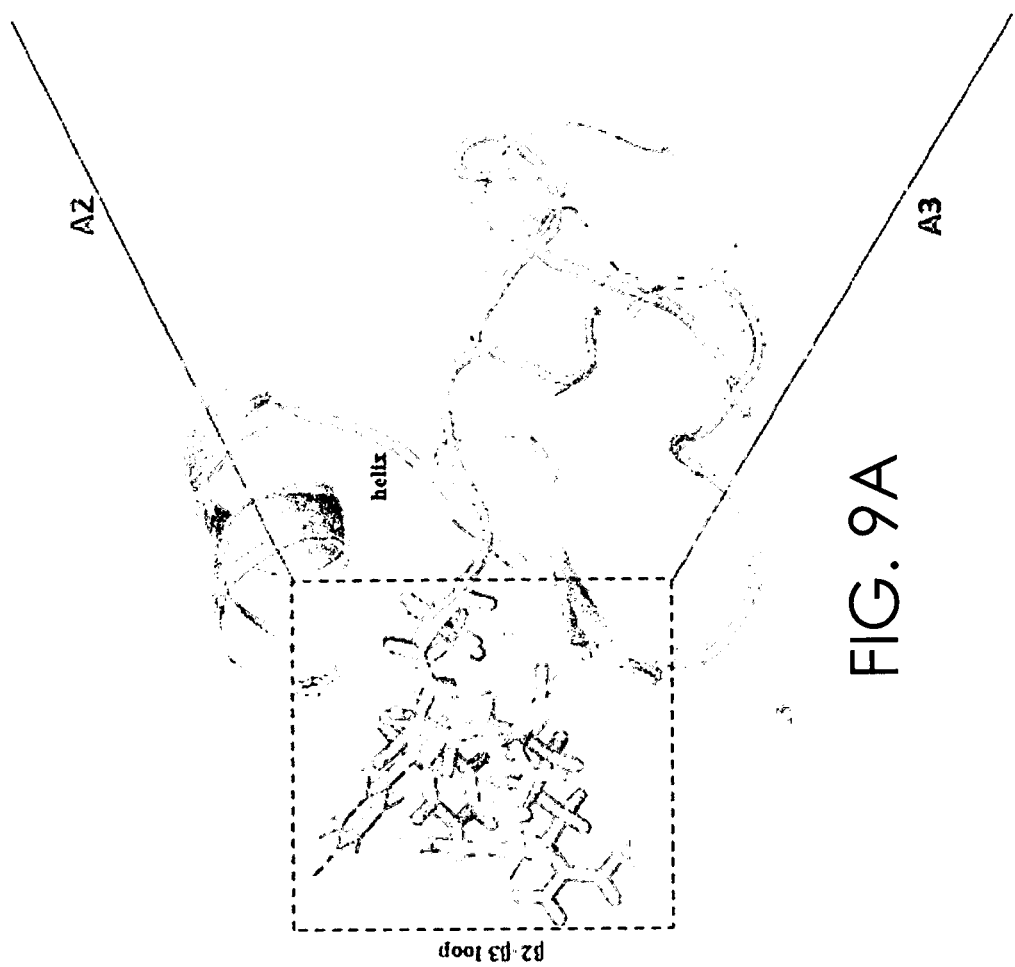
FIG. 9A shows the superimposition of the JJ2-JJ3 loop in AvBD-12A2 (SEQ ID NO: 7) (green) and AvBD-12A3 (SEQ ID NO: 8) (red) and visual comparison of the structure of the P2-P3 loop in each of AvBD-12A2 (SEQ ID NO: 7) and AvBD-12A3 (SEQ ID NO: 8), in accordance with an aspect of the present invention.

Superimposition of the predicted three dimensional structures of AvBD-12 (SEQ ID NO: 5) and the structure of human P-defensin 6 (hBD6) revealed a similar N-terminal alpha-helix and an adjacent P2-P3 loop, in addition to conserved internal P-sheet domains (FIGS. 8A and 8B). The alpha-helix and P2-P3 loop have been identified by NMR spectroscopy as a contiguous binding surface for human CCR2. A comparison of the predicted three dimensional structures of AvBD-6 (SEQ ID NO: 13) and AvBD-12 (SEQ ID NO: 5) showed only the P2-P3 loop in AvBD-6 (SEQ ID NO: 13). AvBD-6 (SEQ ID NO: 13) had an N-terminal coil turn instead of the alpha-helix. Peptide charge distribution analysis indicated that positively charged amino acid residues (H4R7R10R38R40) in the N-termini and C-termini of AvBD-6 (SEQ ID NO: 13) formed a cluster, and that positively charged residues (H7R9K36) of AvBD-12 (SEQ ID NO: 5) were separated by negatively charged residues (FIGS. 8A and 8B). The N-terminal alpha-helix and the P2-P3 loop were observed in the predicted structures of AvBD-12A2 (SEQ ID NO: 7) and AvBD-12A3 (SEQ ID NO: 8). A difference in the P2-P3 loop between AvBD-12A2 (SEQ ID NO: 7) and AvBD-12A3 (SEQ ID NO: 8) was predicted (FIG. 9A). Based on the predictions for AvBD-12A2 (SEQ ID NO: 7), the —C═O group in the main chain of F28 formed a hydrogen bond with the —NH group in the side chain of R29, resulting in the fold-back of R29 side-chain (FIG. 9B). Based on the predictions for AvBD-12A3 (SEQ ID NO: 8), there appeared to be no hydrogen bond formation between R29 and F28. Instead, there appeared to be C—H/O interactions between the —CH groups in the aromatic it ring of F28 and the —C═O group of F28, as well as the —CH group in the side chain of S27. In view of this prediction, the side chain of R29 is believed to protrude toward the surface of the AvBD-12A3 (SEQ ID NO: 8) peptide and the aromatic ring of F28 in AvBD-12A3 (SEQ ID NO: 8) turned in parallel with R29 side chain (FIG. 9C).

Example Two

Antimicrobial Activity Assay and Results

*Escherichia coli* (ATCC 25922), *Pseudomonas aeruginosa* (ATCC 27853), *Salmonella enteric* serovar *Typhimurium* (ATCC 14028) and *Staphylococcus aureus* (ATCC 29213) were used to assess the antimicrobial activity of AvBD analogues (SEQ ID NOs: 5, 6, 7, 8, 9, 10, 11, 12, and 13). All bacterial strains were grown on Luria-Bertani (LB) agar plates or Trypticase Soy Agar with 5% Sheep Blood (TSA, Thermo Fisher Scientific) plates at 37° C. Antimicrobial activity was determined by a colony counting assay. In brief, bacteria were suspended in 100-fold diluted Mueller Hinton broth with 5 mM NaCl (minimal growth medium) to obtain a final bacterial concentration of $2 \times 10^5$ CFU/ml. Twenty-five microliters of bacterial suspension and 25 μl of AvBD analogue (SEQ ID NOs: 5, 6, 7, 8, 9, 10, 11, 12, and 13) solution were mixed in the wells of a 96-well polypropylene microtiter plate (Nunc™, Thermo Fisher Scientific). The final peptide concentrations were 2, 4, 8, 16, 32, 64 and 128 μg/ml. The minimal growth medium without AvBD peptide (SEQ ID NO: 5, 6, 7, 8, 9, 10, 11, 12, and 13) was included as a negative control. The bacterial-peptide mixtures were incubated at 37° C. for 2 hours, 10-fold serially diluted and plated on LB agar plates. The numbers of bacterial colonies were enumerated after 16 hours of incubation at 37° C. Antimicrobial activity was expressed as percent of killing using the following formula: $(\text{CPU}_{control} - \text{CFU}_{treated})/\text{CFU}_{control} \times 100\%$. To assess the resistance of AvBD analogues (SEQ ID NOs: 5, 6, 7, 8, 9, 10, 11, 12, and 13) to sodium chloride (NaCl), antimicrobial assays were carried out in the presence of 5 mM, 50 mM, 100 mM or 150 mM NaCl. All assays were performed in triplicate.

Group 1 analogues (AvBD-12A1 [SEQ ID NO: 6], AvBD-12A2 [SEQ ID NO: 7], AvBD-12A3 [SEQ ID NO: 8]) with increased net positive charge and hydrophobicity were significantly (p<0.05) more effective than the parent peptide AvBD-12 (SEQ ID NO: 5) in killing *E. coli* (FIG. 10A), *S.*

Figure 10A:
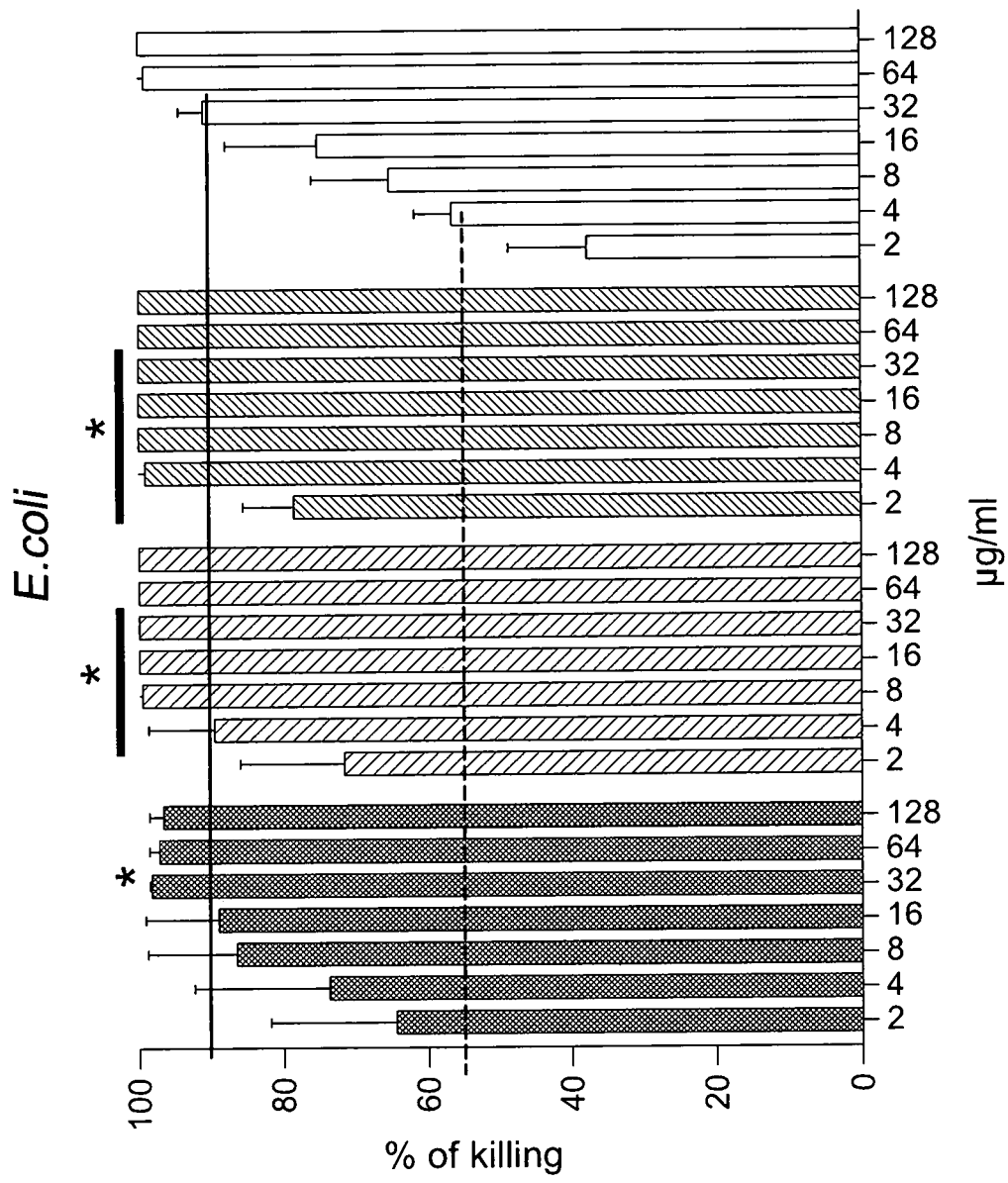
FIG. 10A is a bar graph showing the antimicrobial activity of group 1 analogues (AvBD-12A1 [SEQ ID NO: 6], AvBD-12A2 [SEQ ID NO: 7], AvBD-12A3 [SEQ ID NO: 8]) as percent of killing compared to non-AvBD treated control against *E. coli* when said bacteria ($10^5$ CFU/ml) were incubated with peptides at various concentrations, ranging from 2 to 128 µg/ml at 37° C. for 2 hours, in accordance with an aspect of the present invention.
Figure 10B:
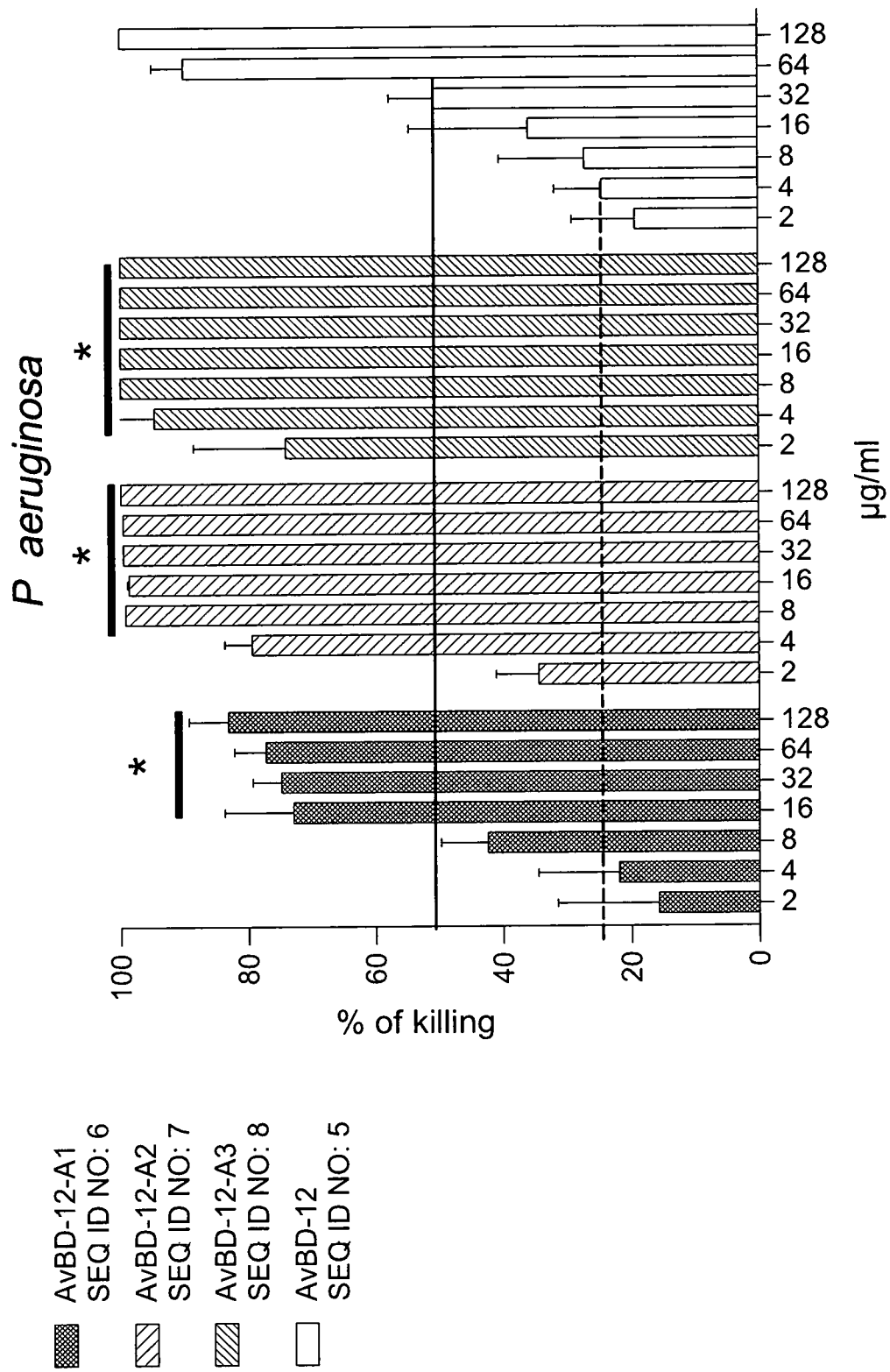
FIG. 10B is a bar graph showing the antimicrobial activity of group 1 analogues (AvBD-12A1 [SEQ ID NO: 6], AvBD-12A2 [SEQ ID NO: 7], AvBD-12A3 [SEQ ID NO: 8]) as percent of killing compared to non-AvBD treated control against *P. aeruginosa* when said bacteria ($10^5$ CFU/ml) were incubated with peptides at various concentrations, ranging from 2 to 128 µg/ml at 37° C. for 2 hours, in accordance with an aspect of the present invention.
Figure 10C:
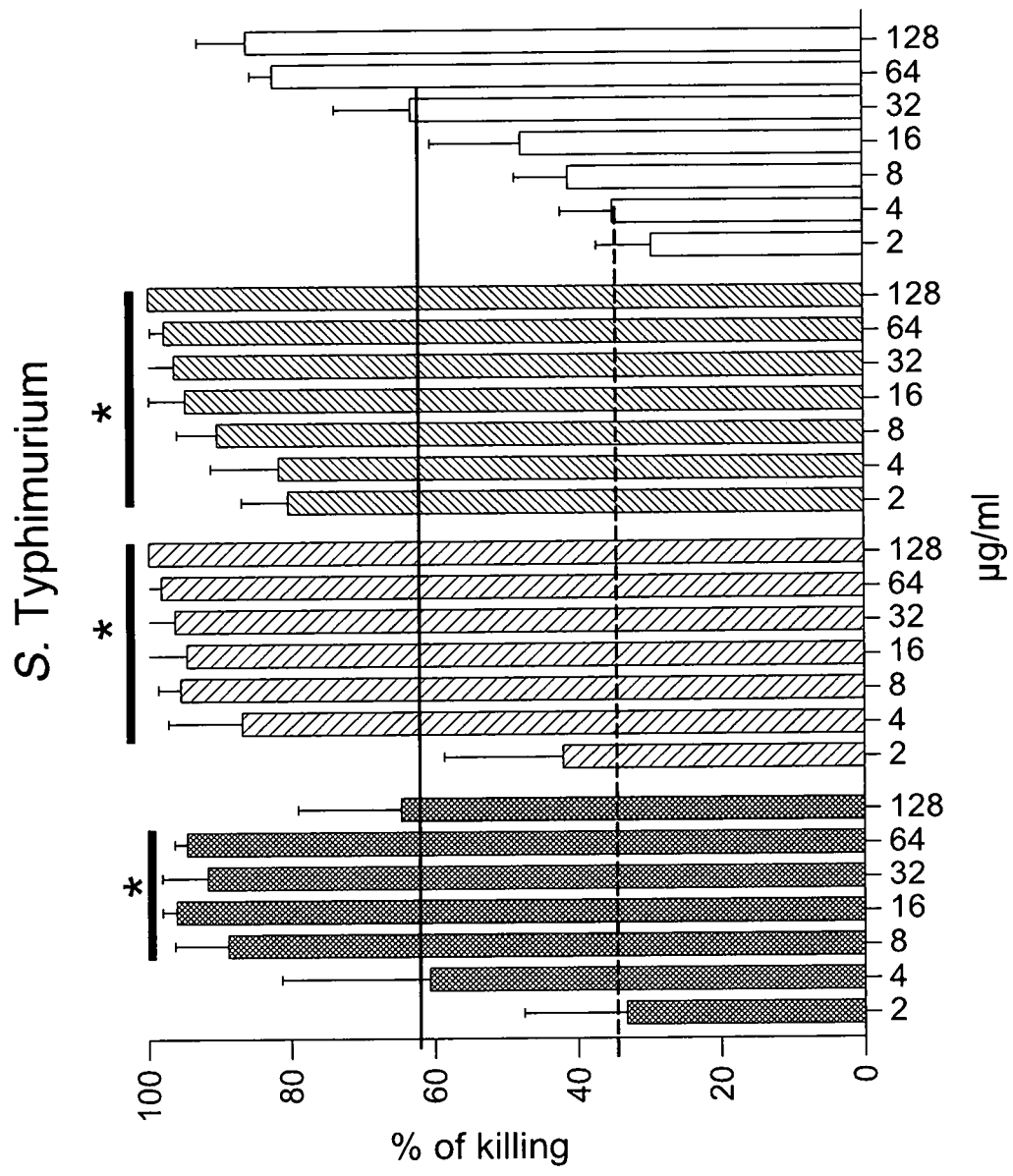
FIG. 10C is a bar graph showing the antimicrobial activity of group 1 analogues (AvBD-12A1 [SEQ ID NO: 6], AvBD-12A2 [SEQ ID NO: 7], AvBD-12A3 [SEQ ID NO: 8]) as percent of killing compared to non-AvBD treated control against *S. Typhimurium* when said bacteria ($10^5$ CFU/ml) were incubated with peptides at various concentrations, ranging from 2 to 128 µg/ml at 37° C. for 2 hours, in accordance with an aspect of the present invention.
Figure 10D:
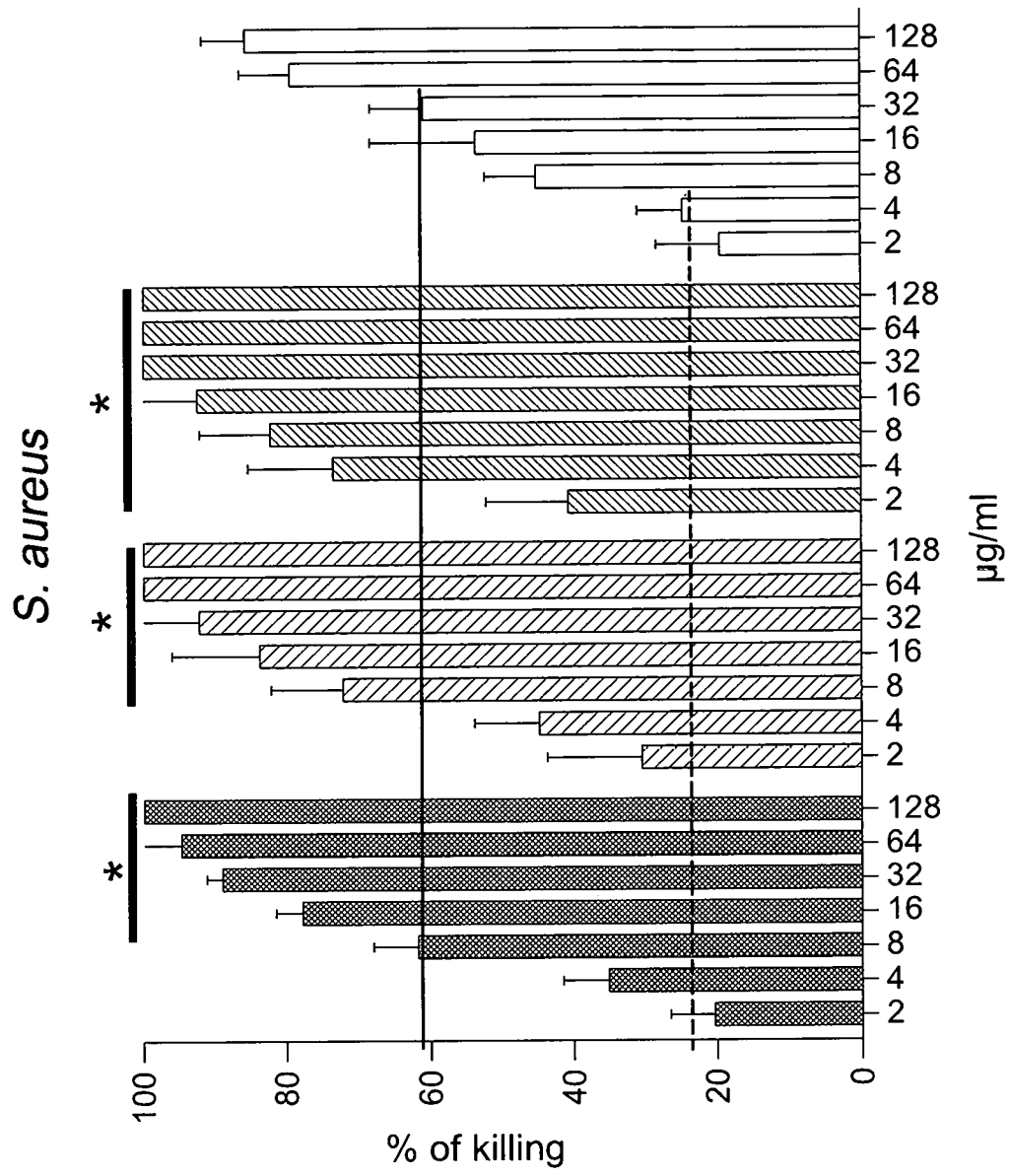
FIG. 10D is a bar graph showing the antimicrobial activity of group 1 analogues (AvBD-12A1 [SEQ ID NO: 6], AvBD-12A2 [SEQ ID NO: 7], AvBD-12A3 [SEQ ID NO: 8]) as percent of killing compared to non-AvBD treated control against *S. aureus* when said bacteria ($10^5$ CFU/ml) were incubated with peptides at various concentrations, ranging from 2 to 128 µg/ml at 37° C. for 2 hours, in accordance with an aspect of the present invention.
Figure 11A:
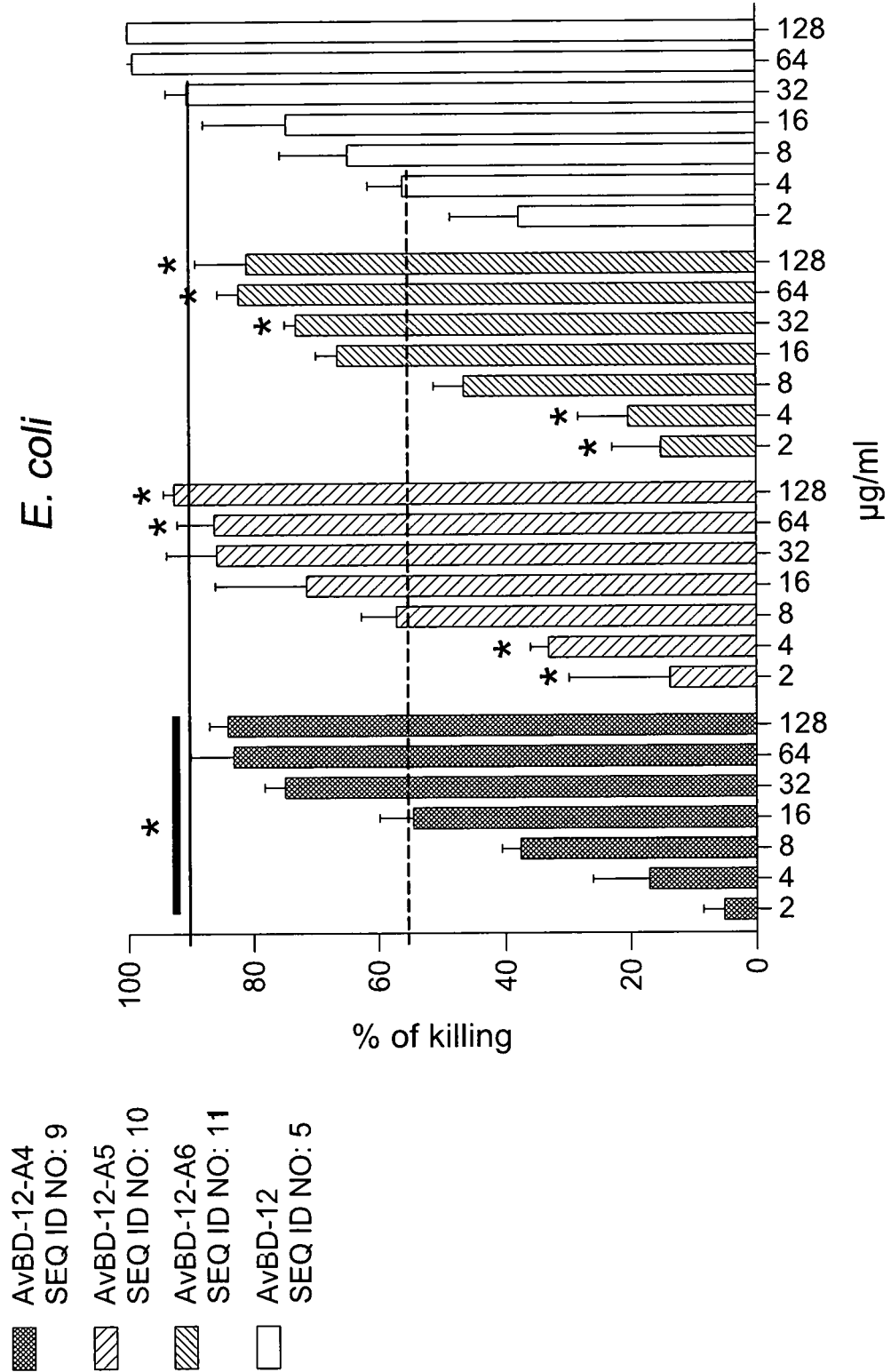
FIG. 11A is a bar graph showing the antimicrobial activity of group 2 analogues (AvBD-12A4 [SEQ ID NO: 9], AvBD-12A5 [SEQ ID NO: 10], AvBD-12A6 [SEQ ID NO: 11]) against *E. coli* when said bacteria ($10^5$ CFU/ml) were incubated with peptides at various concentrations, ranging from 2 to 128 µg/ml at 37° C. for 2 hours, in accordance with an aspect of the present invention.
Figure 11B:
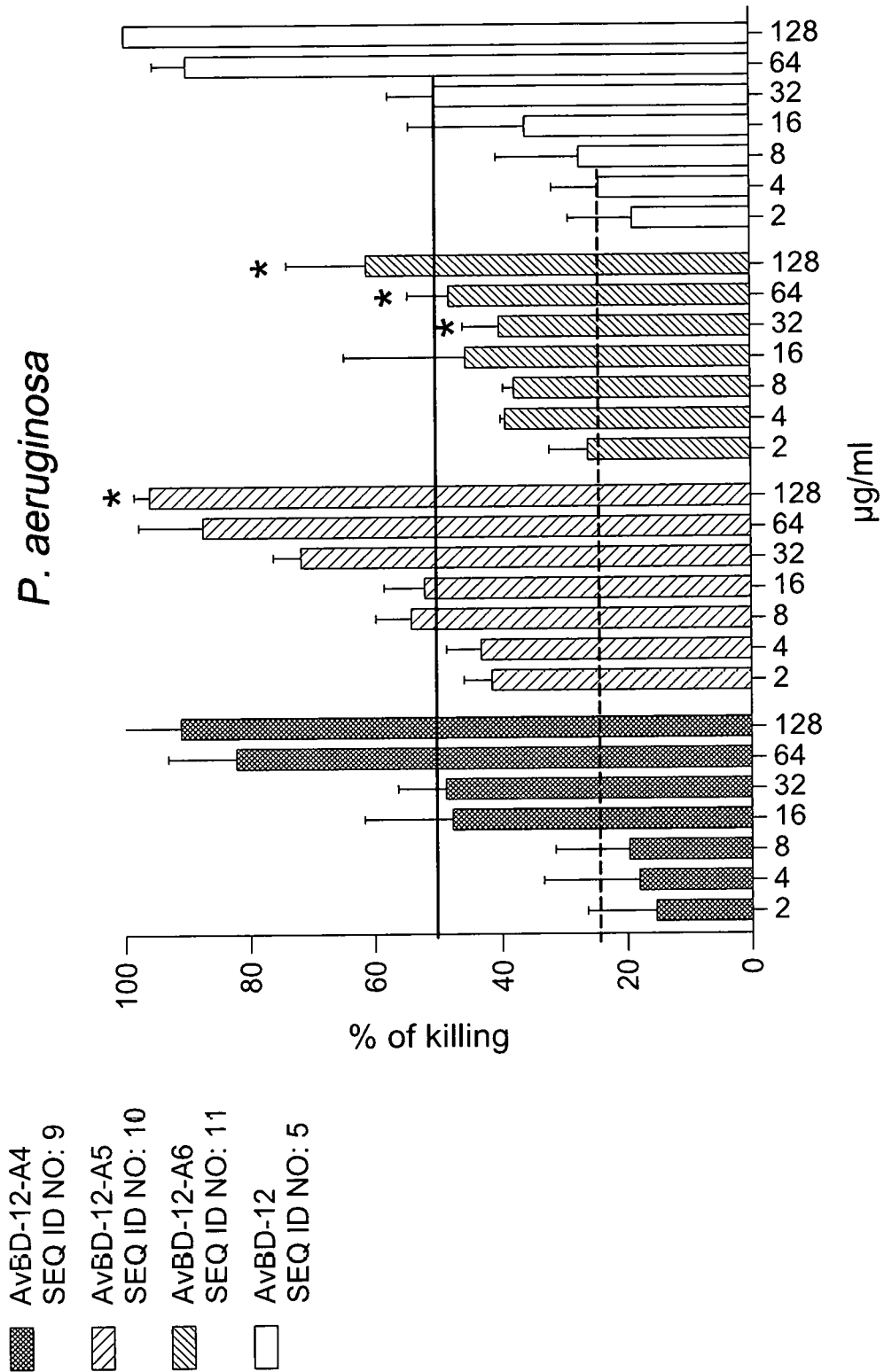
FIG. 11B is a bar graph showing the antimicrobial activity of group 2 analogues (AvBD-12A4 [SEQ ID NO: 9], AvBD-12A5 [SEQ ID NO: 10], AvBD-12A6 [SEQ ID NO: 11]) against *P. aeruginosa* when said bacteria ($10^5$ CFU/ml) were incubated with peptides at various concentrations, ranging from 2 to 128 µg/ml at 37° C. for 2 hours, in accordance with an aspect of the present invention.
Figure 11C:
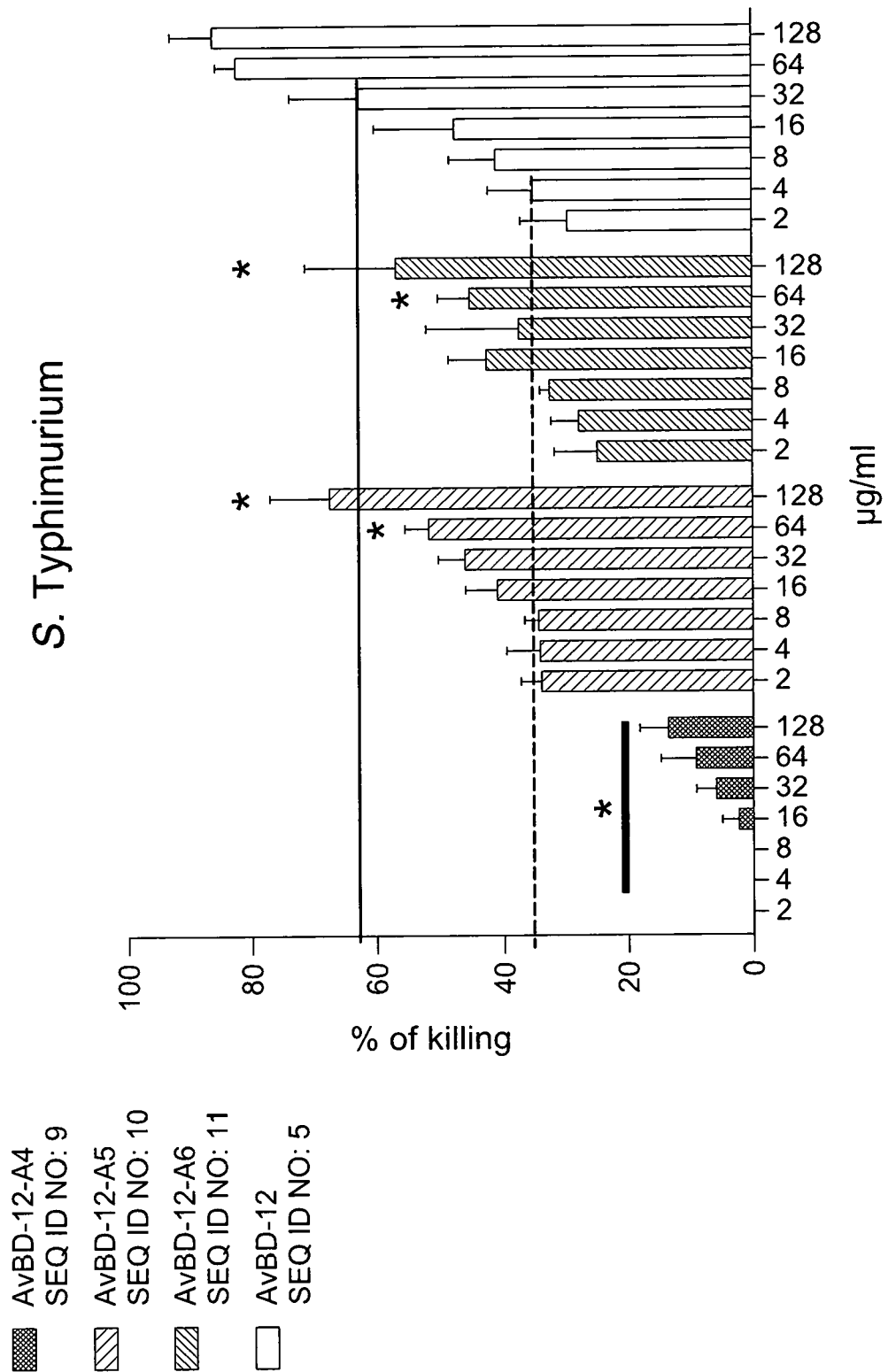
FIG. 11C is a bar graph showing the antimicrobial activity of group 2 analogues (AvBD-12A4 [SEQ ID NO: 9], AvBD-12A5 [SEQ ID NO: 10], AvBD-12A6 [SEQ ID NO: 11]) against *S. Typhimurium* when said bacteria ($10^5$ CFU/ml) were incubated with peptides at various concentrations, ranging from 2 to 128 µg/ml at 37° C. for 2 hours, in accordance with an aspect of the present invention.
Figure 11D:
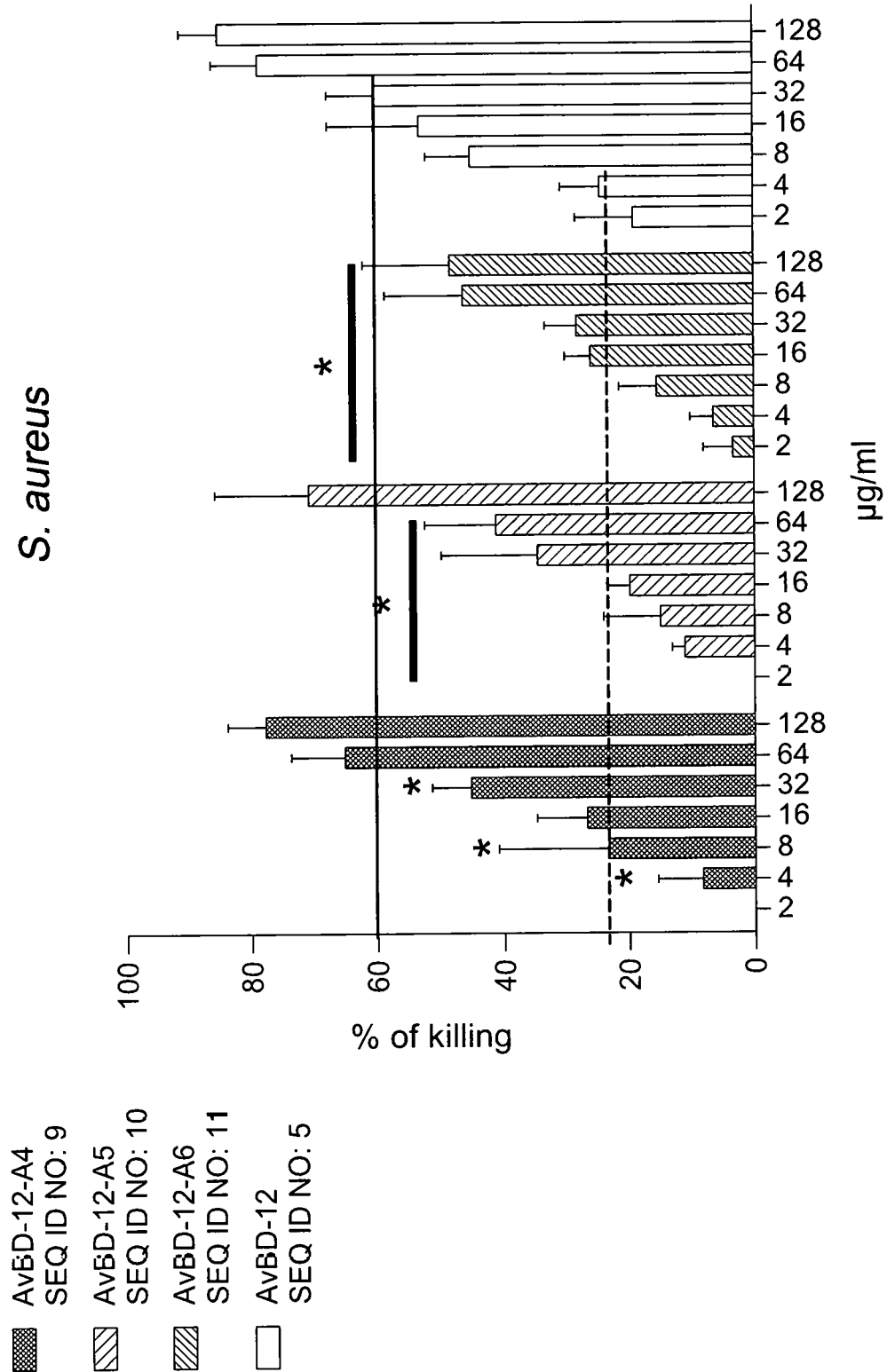
FIG. 11D is a bar graph showing the antimicrobial activity of group 2 analogues (AvBD-12A4 [SEQ ID NO: 9], AvBD-12A5 [SEQ ID NO: 10], AvBD-12A6 [SEQ ID NO: 11]) against *S. aureus* when said bacteria ($10^5$ CFU/ml) were incubated with peptides at various concentrations, ranging from 2 to 128 µg/ml at 37° C. for 2 hours, in accordance with an aspect of the present invention.
Figure 12A:
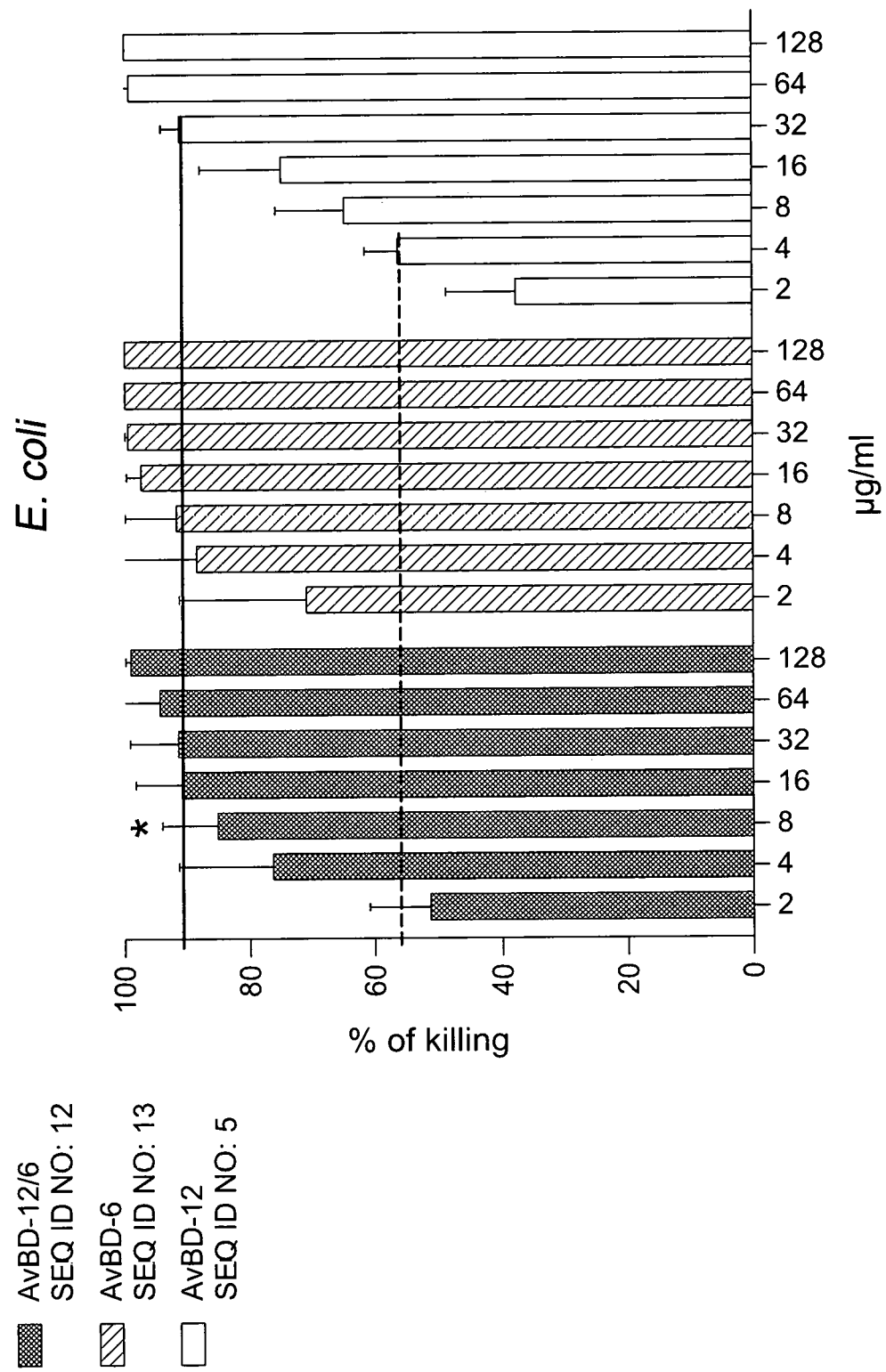
FIG. 12A is a bar graph showing the antimicrobial activity of hybrid peptide AvBD-12/6 (SEQ ID NO: 12) as percent of killing compared to non-AvBD treated control against *E. coli* when said bacteria ($10^5$ CFU/ml) were incubated with peptides at various concentrations, ranging from 2 to 128 µg/ml at 37° C. for 2 hours, in accordance with an aspect of the present invention.
Figure 12B:
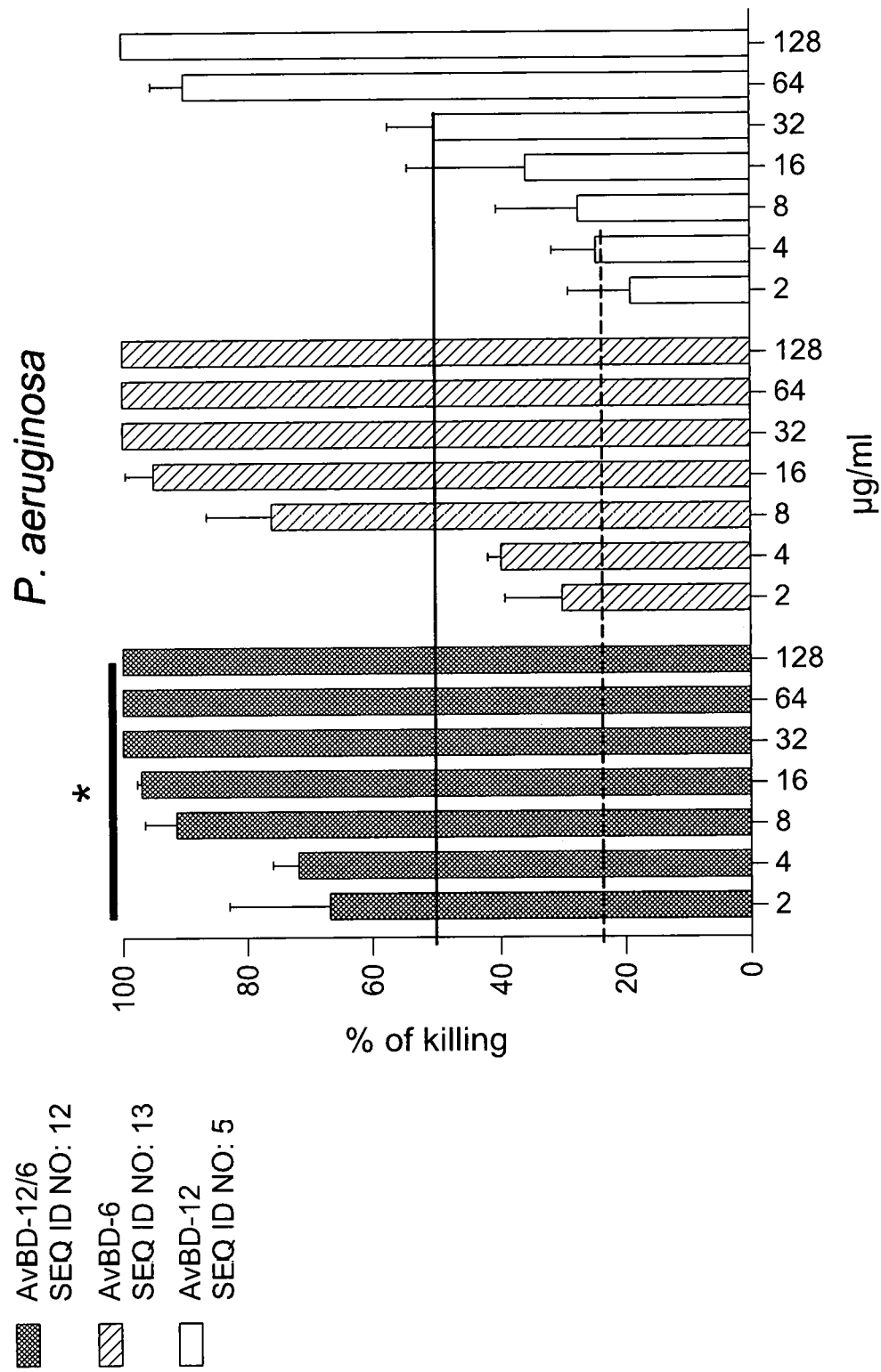
FIG. 12B is a bar graph showing the antimicrobial activity of hybrid peptide AvBD-12/6 (SEQ ID NO: 12) presented as percent of killing compared to non-AvBD treated control against *P. aeruginosa* when said bacteria ($10^5$ CFU/ml) were incubated with peptides at various concentrations, ranging from 2 to 128 µg/ml at 37° C. for 2 hours, in accordance with an aspect of the present invention.
Figure 12C:
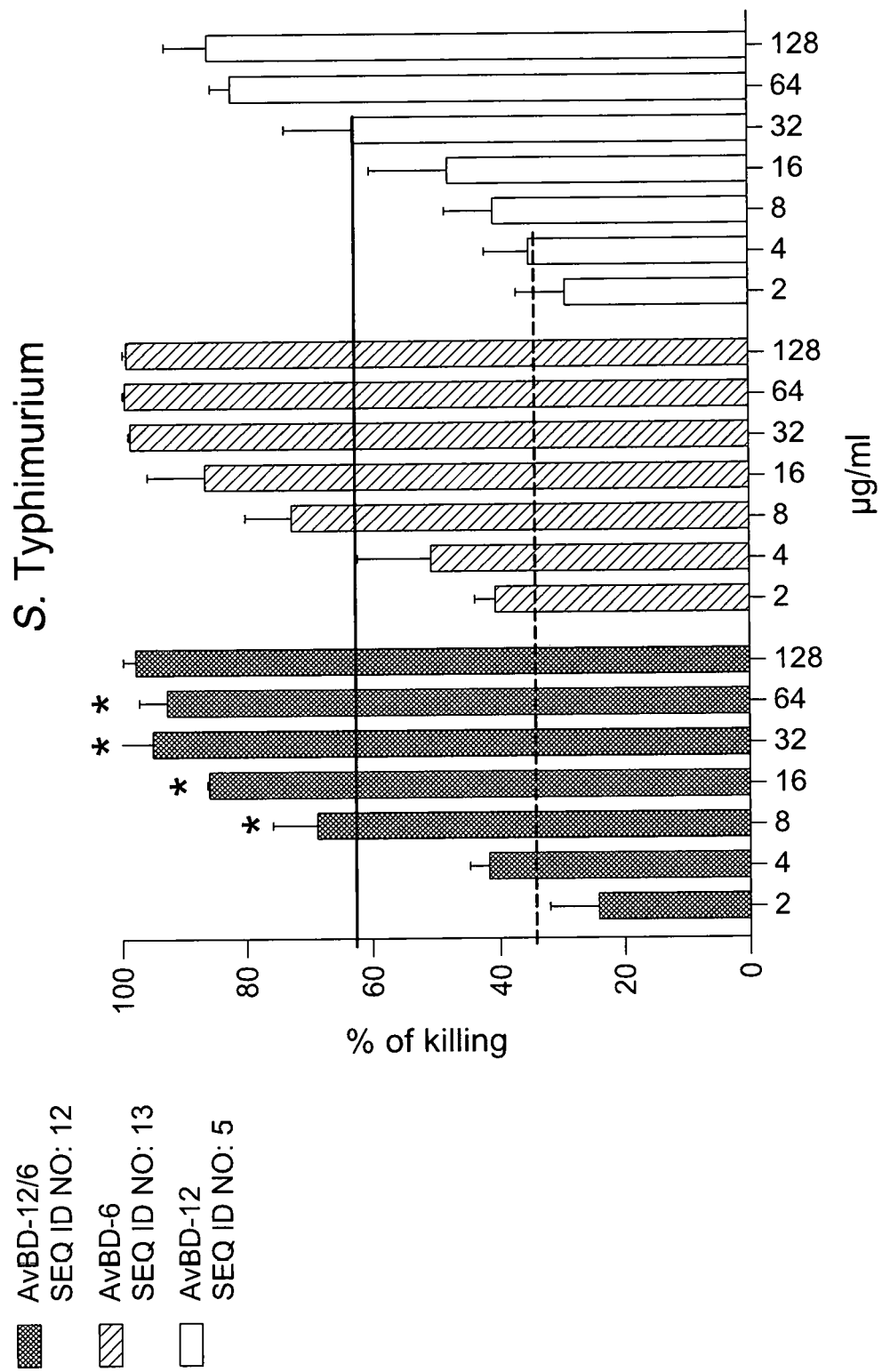
FIG. 12C is a bar graph showing the antimicrobial activity of hybrid peptide AvBD-12/6 (SEQ ID NO: 12) presented as percent of killing compared to non-AvBD treated control against *S. Typhimurium* when said bacteria ($10^5$ CFU/ml) were incubated with peptides at various concentrations, ranging from 2 to 128 µg/ml at 37° C. for 2 hours, in accordance with an aspect of the present invention.
Figure 12D:
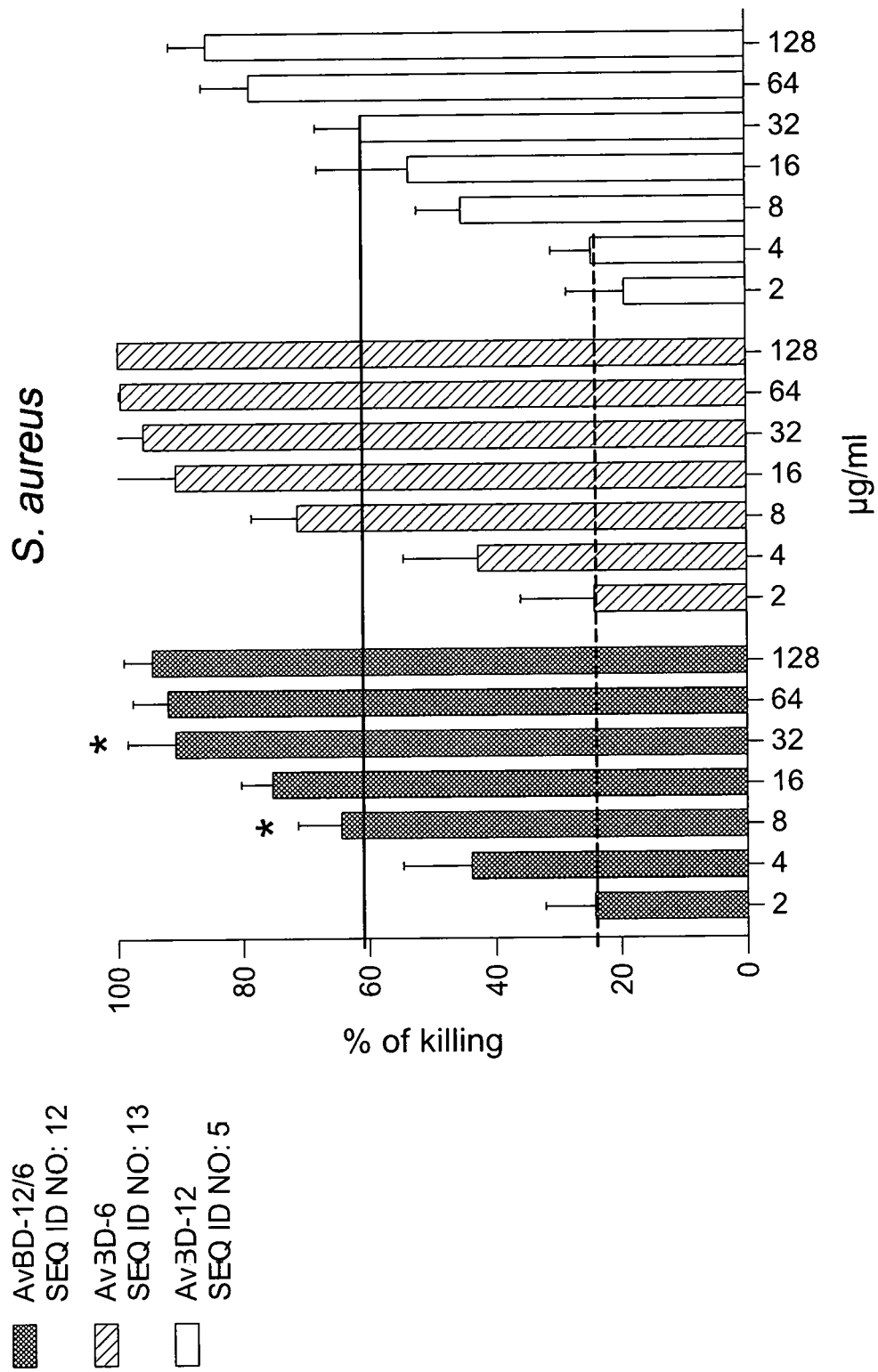
FIG. 12D is a bar graph showing the antimicrobial activity of hybrid peptide AvBD-12/6 (SEQ ID NO: 12) presented as percent of killing compared to non-AvBD treated control against *S. aureus* when said bacteria ($10^5$ CFU/ml) were incubated with peptides at various concentrations, ranging from 2 to 128 µg/ml at 37° C. for 2 hours, in accordance with an aspect of the present invention.

Typhimurium (FIG. 10C), P. aeruginosa (FIG. 10B), and S. aureus (FIG. 10D). At 16 µg/ml, AvBD-12 (SEQ ID NO: 5), AvBD-12A1 (SEQ ID NO: 6), AvBD-12A2 (SEQ ID NO: 7) and AvBD-12A3 (SEQ ID NO: 8) killed 74.4%, 88.6%, 100%, 100% of E. coli; 47.3%, 95.6%, 93.9%, and 93.9% S. Typhimurium; 35.5%, 72.3%, 98%, and 100% of P. aeruginosa; and 52.9%, 77.2%, 83.1%, and 91.7% of S. aureus, respectively. AvBD-12A2 (SEQ ID NO: 7) and AvBD-12A3 (SEQ ID NO: 8) with a net positive charge of about +9 and hydrophobicity of about 40%, were determined to be more effective than AvBD-12A1 (SEQ ID NO: 6), which exhibited a hydrophobicity about 53% and a net charge of about +5. AvBD-12A2 (SEQ ID NO: 7) and AvBD-12A3 (SEQ ID NO: 8), which appeared to have the same or similar net charge and hydrophobicity but non-identical locations of alanine/serine residues, exhibited distinct killing activity against E. coli or P. aeruginosa (FIGS. 10A-B). The bactericidal potency of Group-1 analogues may be ranked, generally, as AvBD-12A3 (SEQ ID NO: 8) >AvBD-12A2 (SEQ ID NO: 7) >AvBD-12A1 (SEQ ID NO: 6) >AvBD-12 (SEQ ID NO: 5). Of the bacterial species tested, E. coli and P. aeruginosa were more susceptible than S. Typhimurium and S. aureus to AvBD-12A3 at medium concentrations, ranging from 8 µg/ml to 32 µg/ml (FIGS. 10C-D).

Group 2 analogues, including AvBD12-A4 (SEQ ID NO: 9), AvBD-12A5 (SEQ ID NO: 10), and AvBD-12A6 (SEQ ID NO: 11), exhibited similar killing activity to that of AvBD-12 (SEQ ID NO: 5) (see FIGS. 11A, 11B, 11C, and 11D). AvBD-12A4 (SEQ ID NO: 9), which is predicted to have one less disulfide bridge (C1-C5 or C5-C34), exhibited a somewhat reduced killed activity than that of AvBD-12 (SEQ ID NO: 5) against S. Typhimurium (p<0.05).

The Group 3 analogue, AvBD-12/6 (SEQ ID NO: 12), predicted to have the backbone of AvBD-12 (SEQ ID NO: 5) and positively charged amino acid residues of AvBD-6 (SEQ ID NO: 13), exhibited killing activities similar to that of AvBD-6 (SEQ ID NO: 13) (see FIGS. 12A, 12B, 12C, and 12D).

Example Two

Microbial Inhibitory Concentration Assay and Results

The minimum inhibitory concentrations (MIC) of AvBDs (SEQ ID NOs: 5, 6, 7, 8, 9, 10, 11, 12, and 13) were determined under low salt and standard conditions according to the guidelines of the Clinical and Laboratory Standards Institute (CLSI). To determine MIC at low salt condition (5 mM NaCl, referred to as "MIC-1s"), peptides were 2-fold serially diluted (2 to 256 µg/ml) in a 96-well microtiter plate. An equal volume (1l1) of bacterial suspension was added to each well of the plate. The final bacterial concentration in the wells was $5 \times 10^5$ CFU/ml. The plate was incubated at 37° C. for 16 to 24 hours and the lowest concentration that completely or near-completely prevented visible bacteria growth was recorded. To complement MIC-1s assays, the minimum bactericidal concentrations (MBC) were evaluated by sub-culturing the contents of the first two clear wells obtained in the MIC-1s assay onto LB agar plates. All assays were conducted in triplicate. The lowest peptide concentration inhibiting about, at least, or more than 99% of bacterial growth was defined as MBC-1s. The analogues were regarded as bactericidal when the MBC was determined to be no more than four times the MIC.

The MIC-1s of AvBD-12A1 (SEQ ID NO: 6), AvBD-12A2 (SEQ ID NO: 7), and AvBD-12A3 (SEQ ID NO: 8) against E. coli, S. Typhimurium, and P. aeruginosa were 2-fold to 16-fold below that of AvBD-12 (SEQ ID NO: 5), confirming an improved antimicrobial property of these analogues. The MIC-1s of the analogues against P. aeruginosa were 2 to 8-fold below that of AvBD-6 (SEQ ID NO: 13). The ratio of MBC-1s/MIC-1s was about equal to or below 4:1 for AvBD-12A2 (SEQ ID NO: 7) and AvBD-12A3 (SEQ ID NO: 8) against the three Gram negative bacterial species tested, suggesting a bactericidal action. The MIC-1s for each of AvBD-12A4 (SEQ ID NO: 9), AvBD-12A5 (SEQ ID NO: 10), and AvBD-12A6 (SEQ ID NO: 11), exhibiting 2, 1, or 0 disulfide bridges, respectively, was higher than that of AvBD-12 (SEQ ID NO: 5) and AvBD-6 (SEQ ID NO:13). The MIC-1s of the analogues was determined to be negatively correlated with the net positive charge. The correlation co-efficiencies (r) for E. coli, S. Typhimurium, P. aeruginosa, and S. aureus were −0.7388, p<0.05; −0.8545, p<0.01; −0.8545, p<0.01; and −0.8727, p<0.01, respectively.

Next, the MICs of AvBD-12A3 (SEQ ID NO: 8) and the parent peptides AvBD-6 (SEQ ID NO: 13) and AvBD-12 (SEQ ID NO: 5) were evaluated under conditions outlined in CLSI guidelines. Somewhat high MICs (128 to 256 µg/ml or above) were obtained (Table 5) (contd on next page).

TABLE 5

Minimum Inhibitory Concentration and Minimum Bactericidal Concentration

| | Bacteria (strain) | | | | | | | | | | | |
|---|---|---|---|---|---|---|---|---|---|---|---|---|
| | E. coli (ATCC 25922) | | | S. Typhimurium (ATCC 14028) | | | P. aeruginosa (ATCC 27853) | | | S. aureus (ATCC 29213) | | |
| Defensins | MIC-Is | MBC-Is | MIC | MIC-Is | MBC-Is | MIC | MIC-Is | MBS-Is | MIC | MIC-Is | MBC-Is | MIC |
| AvBD-12-A1 SEQ ID NO: 6 | 8 | 32 | N/A | 32 | 128 | N/A | 32 | 256 | N/A | 256 | >256 | N/A |
| AVBD-12-A2 SEQ ID NO: 7 | 4 | 16 | N/A | 16 | 64 | N/A | 16 | 32 | N/A | 256 | 256 | N/A |
| AvBD-12-A3 SEQ ID NO: 8 | 4 | 16 | 128 | 16 | 64 | >256 | 8 | 16 | >256 | 128 | 256 | >256 |
| AvBD-12-A4 SEQ ID NO: 9 | 128 | >256 | N/A | 256 | >256 | N/A | 256 | >256 | N/A | >256 | >256 | N/A |
| AvBD-12-A5 SEQ ID NO: 10 | 64 | 256 | N/A | 256 | >256 | N/A | 256 | >256 | N/A | >256 | >256 | N/A |
| AvBD-12-A6 SEQ ID NO: 11 | 64 | 256 | N/A | 256 | >256 | N/A | 256 | >256 | N/A | >256 | >256 | N/A |

TABLE 5-continued

Minimum Inhibitory Concentration and Minimum Bactericidal Concentration

| | Bacteria (strain) | | | | | | | | | | |
|---|---|---|---|---|---|---|---|---|---|---|---|
| | E. coli (ATCC 25922) | | | S. Typhimurium (ATCC 14028) | | | P. aeruginosa (ATCC 27853) | | | S. aureus (ATCC 29213) | | |
| Defensins | MIC-Is | MBC-Is | MIC | MIC-Is | MBC-Is | MIC | MIC-Is | MBS-Is | MIC | MIC-Is | MBC-Is | MIC |
| AvBD-12/6 SEQ ID NO: 12 | 8 | 32 | 256 | 16 | 64 | >256 | 64 | 256 | >256 | 256 | 256 | 256 |
| AvBD-6 SEQ ID NO: 13 | 4 | 16 | 128 | 16 | 64 | >256 | 64 | 128 | >256 | 256 | 256 | 256 |
| AvBD-12 SEQ ID NO: 5 | 32 | 128 | 256 | 128 | 256 | >256 | 128 | >256 | >256 | 256 | 256 | >256 |

Example Two

Antimicrobial Activity in the Presence of Salts and Results

Figure 13A:
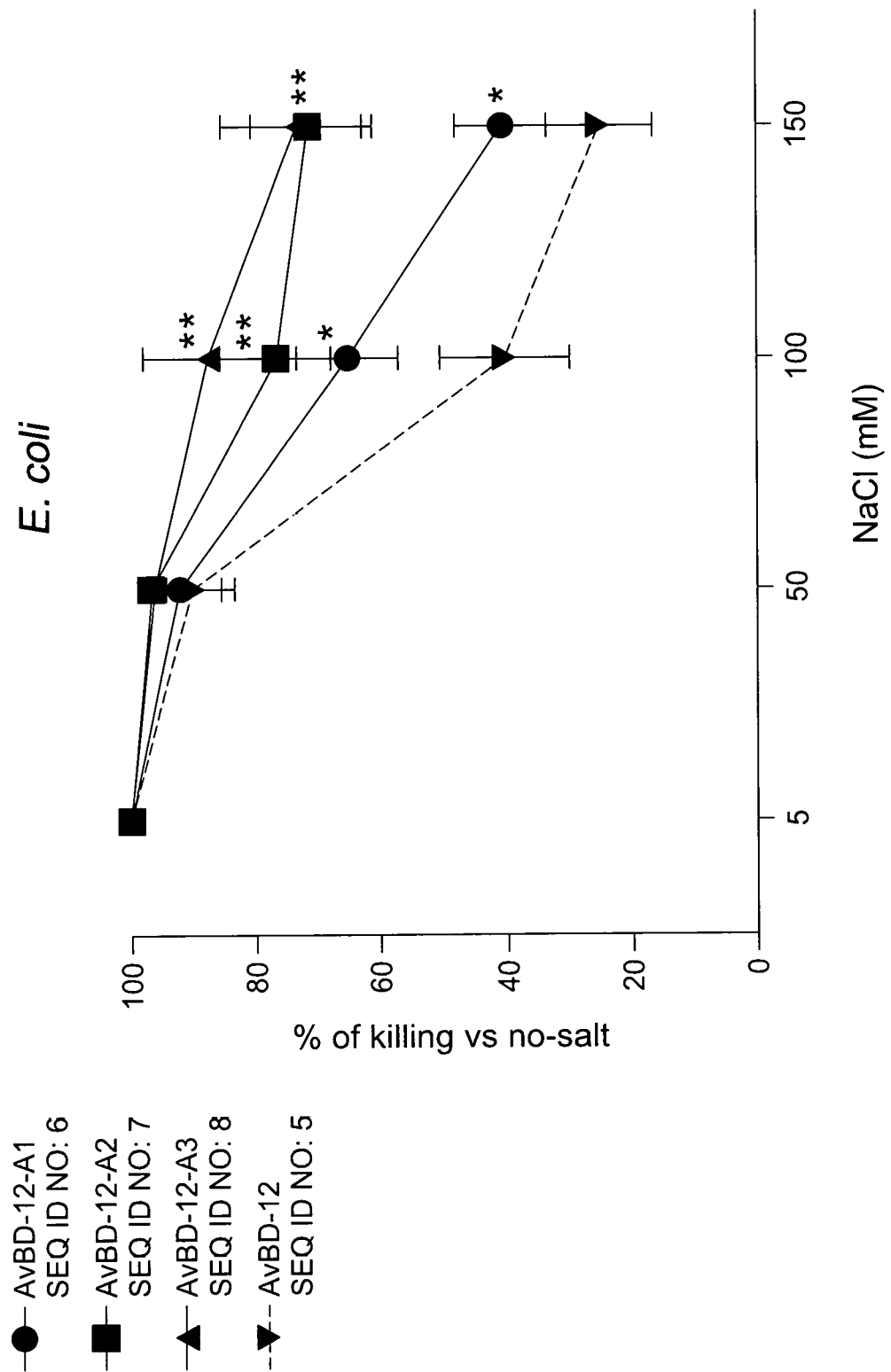
FIG. 13A is a graph showing the effect of NaCl on the antimicrobial activity of group 1 analogues (AvBD-12A1 [SEQ ID NO: 6], AvBD-12A2 [SEQ ID NO: 7], AvBD-12A3 [SEQ ID NO: 8]) when *E. coli* was treated with group one analogues at 16 µg/ml in the presence of 5 mM, 50 mM, 100 mM or 150 mM NaCl, in accordance with an aspect of the present invention.
Figure 13B:
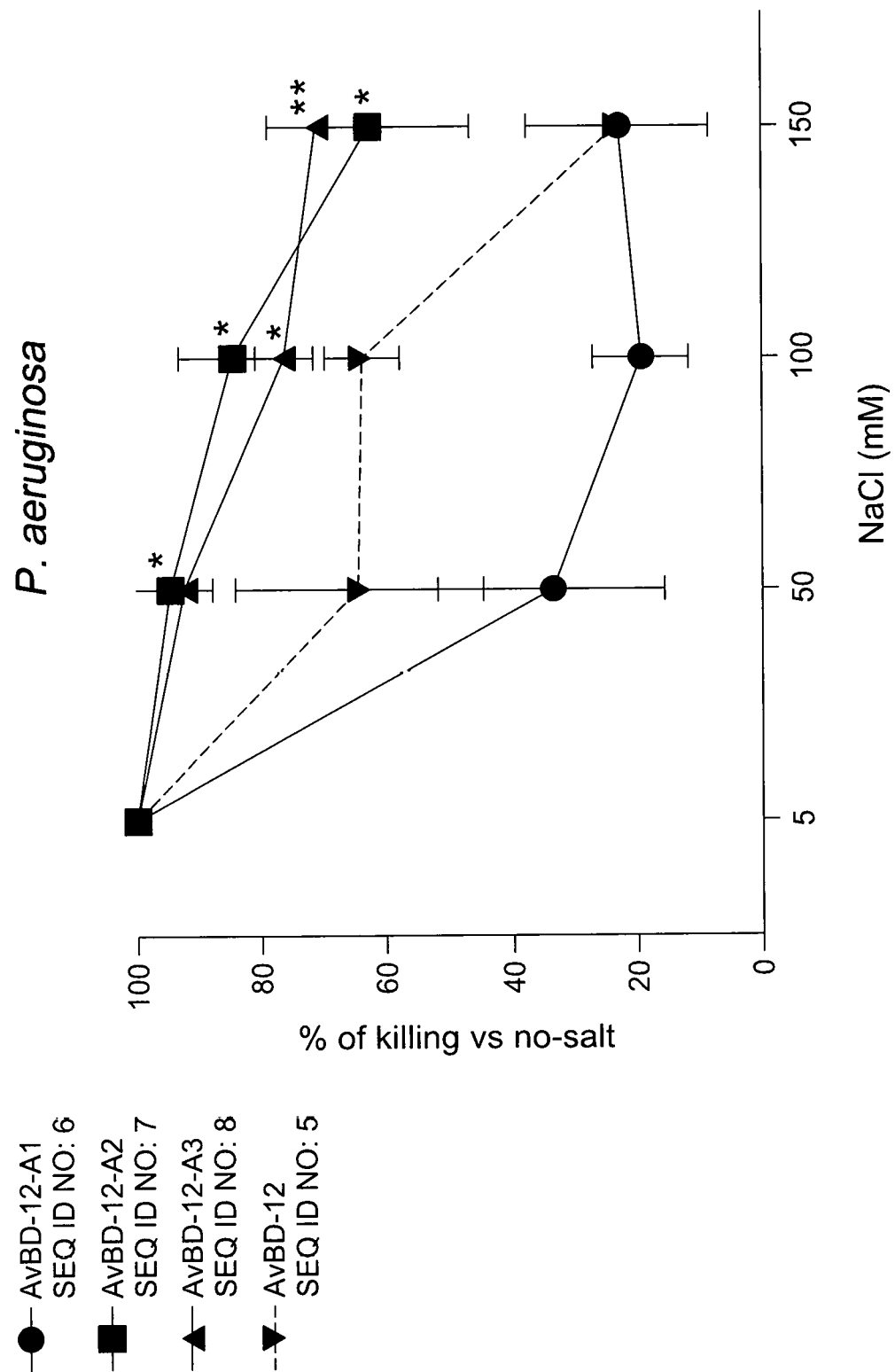
FIG. 13B is a graph showing the effect of NaCl on the antimicrobial activity of group 1 analogues (AvBD-12A1 [SEQ ID NO: 6], AvBD-12A2 [SEQ ID NO: 7], AvBD-12A3 [SEQ ID NO: 8]) when *P. aeruginosa* was treated with group one analogues at 32 µg/ml in the presence of 5 mM, 50 mM, 100 mM or 150 mM NaCl, in accordance with an aspect of the present invention.
Figure 13C:
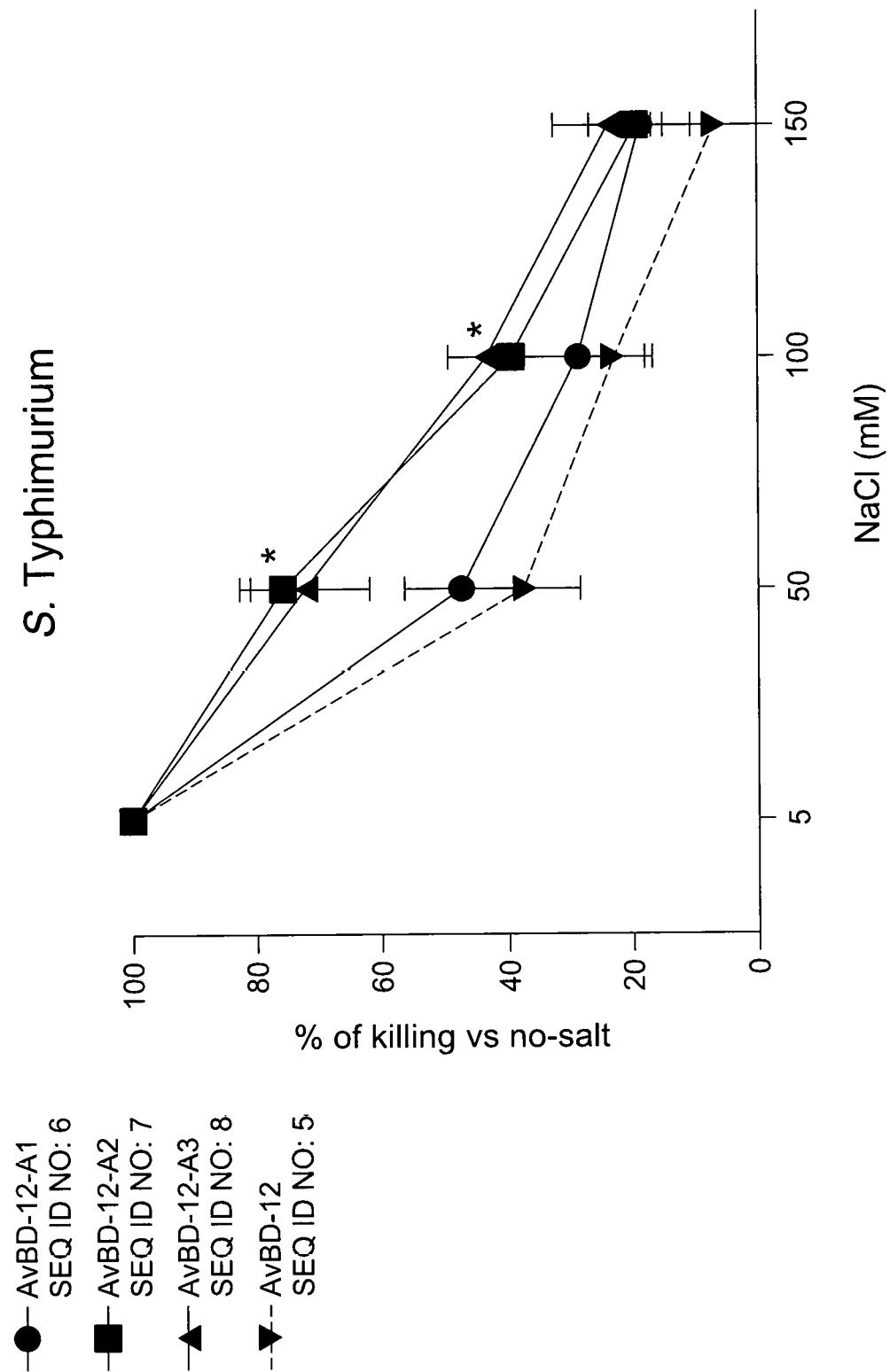
FIG. 13C is a graph showing the effect of NaCl on the antimicrobial activity of group one AvBDs when *S. Typhimurium* was treated with group one analogues at 32 µg/ml in the presence of 5 mM, 50 mM, 100 mM or 150 mM NaCl, in accordance with an aspect of the present invention.
Figure 13D:
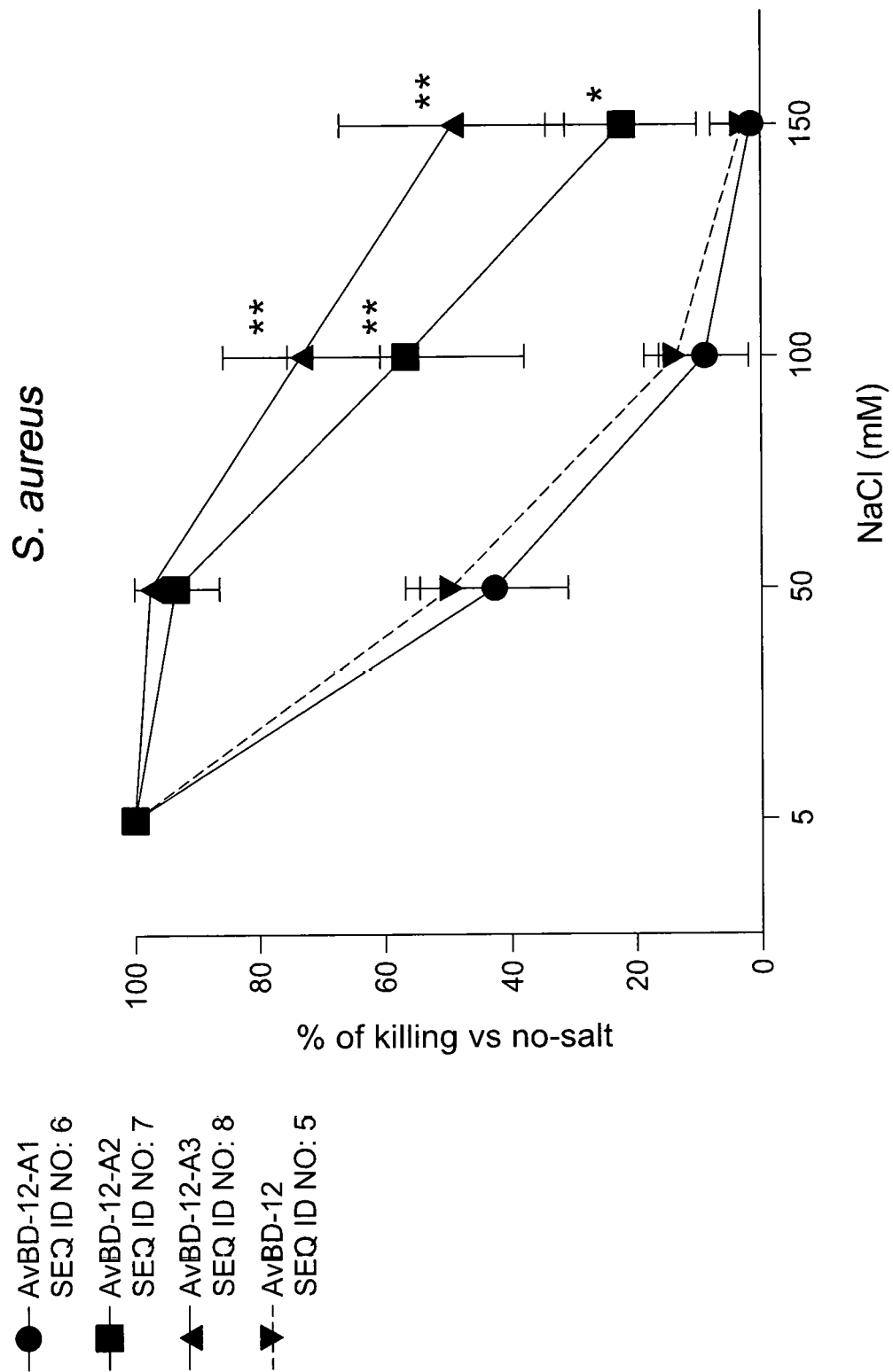
FIG. 13D is a graph showing the effect of NaCl on the antimicrobial activity of group 1 analogues (AvBD-12A1 [SEQ ID NO: 6], AvBD-12A2 [SEQ ID NO: 7], AvBD-12A3 [SEQ ID NO: 8]) when *S. aureus* was treated with group one analogues at 64 µg/ml in the presence of 5 mM, 50 mM, 100 mM or 150 mM NaCl, in accordance with an aspect of the present invention.
Figure 14A:
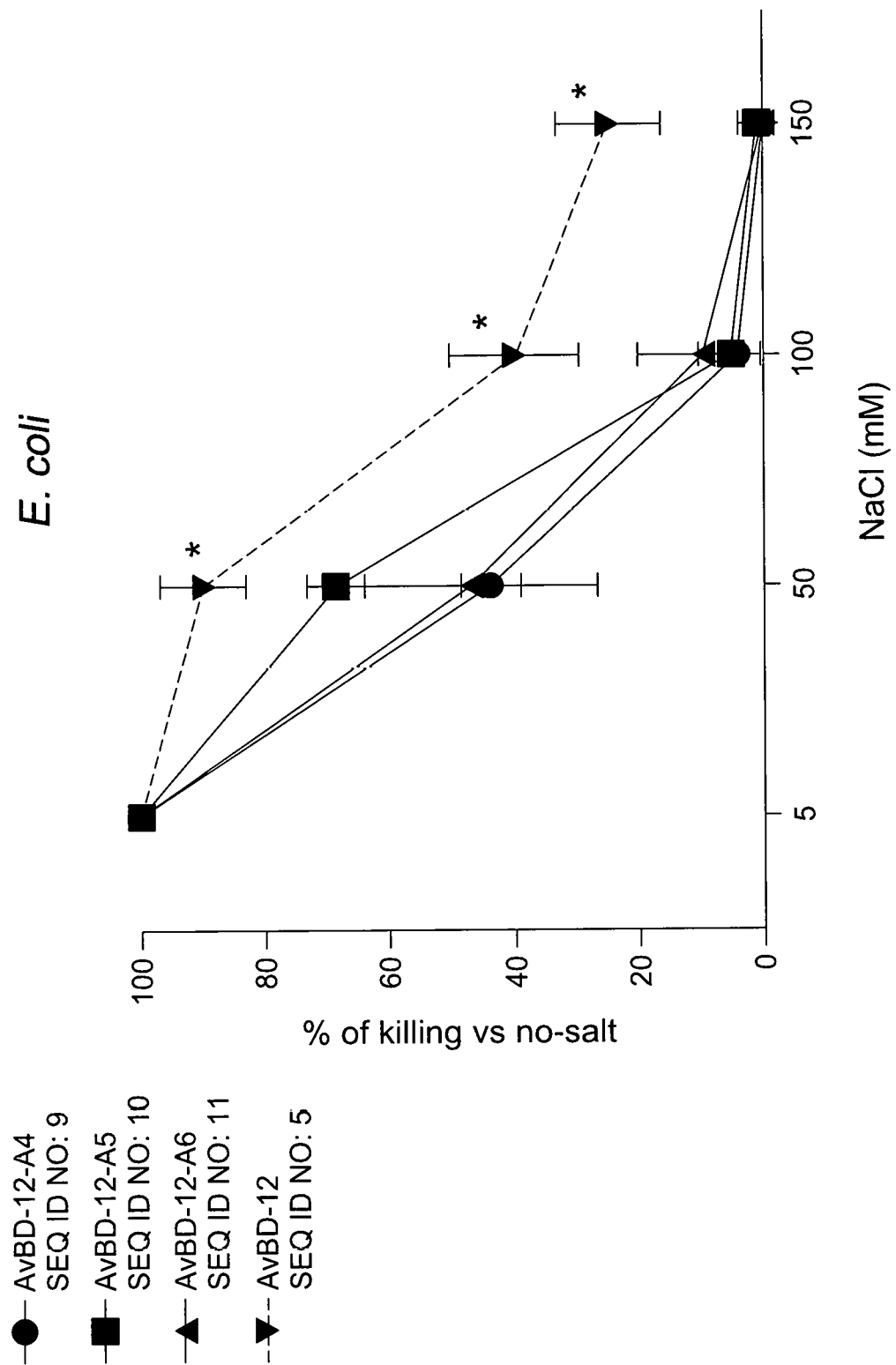
FIGS. 14A-14D are graphs showing the effect of NaCl on the antimicrobial activity of group 2 analogues (AvBD-12A4 [SEQ ID NO: 9], AvBD-12A5 [SEQ ID NO: 10], AvBD-12A6 [SEQ ID NO: 11]) expressed as percent of killing compared to the no-salt control, when various bacteria were treated with group two analogues in the presence of 5 mM, 50 mM, 100 mM or 150 mM NaCl; in accordance with an aspect of the present invention.
Figure 14B:
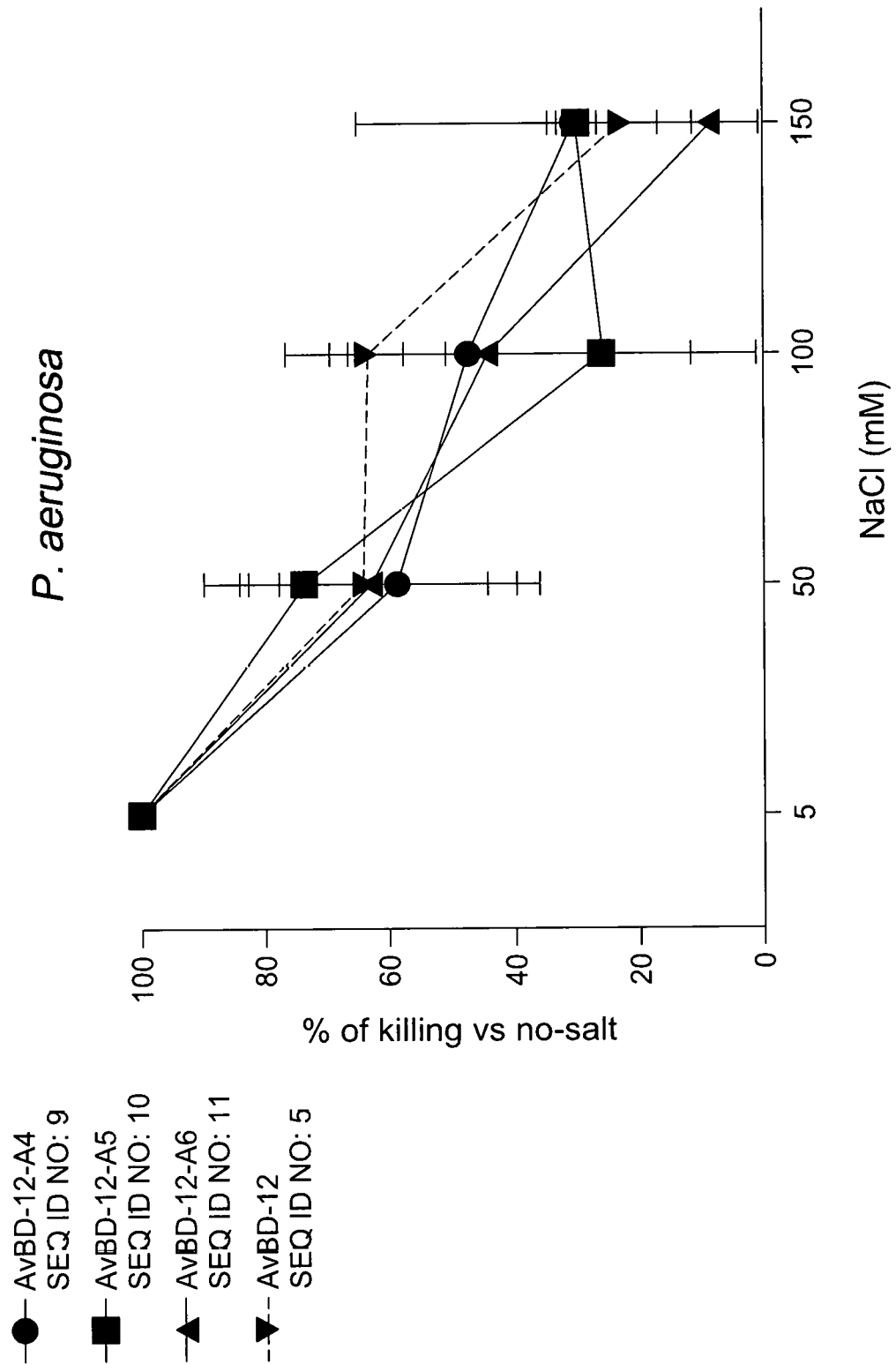
Figure 14C:
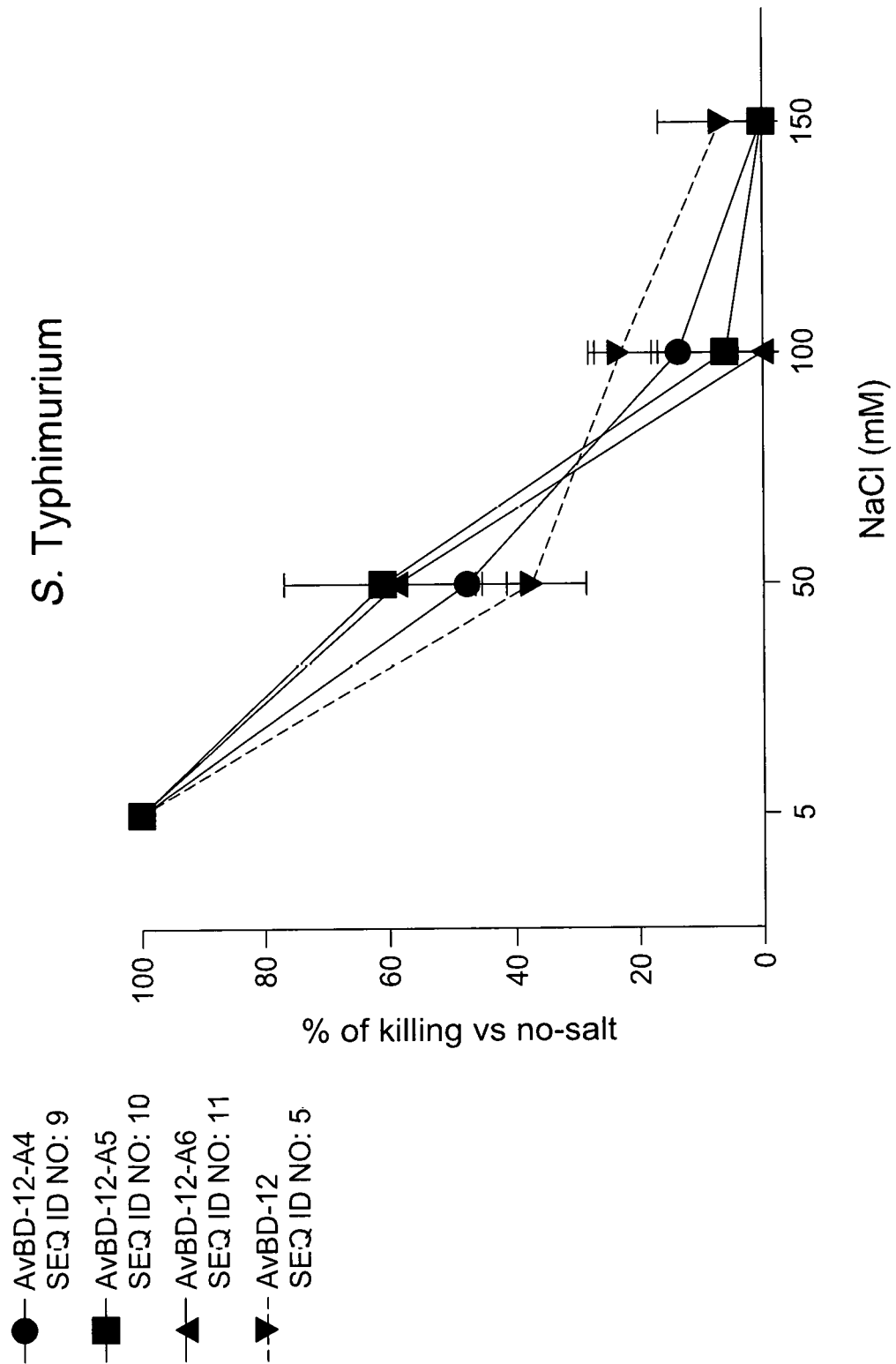
Figure 14D:
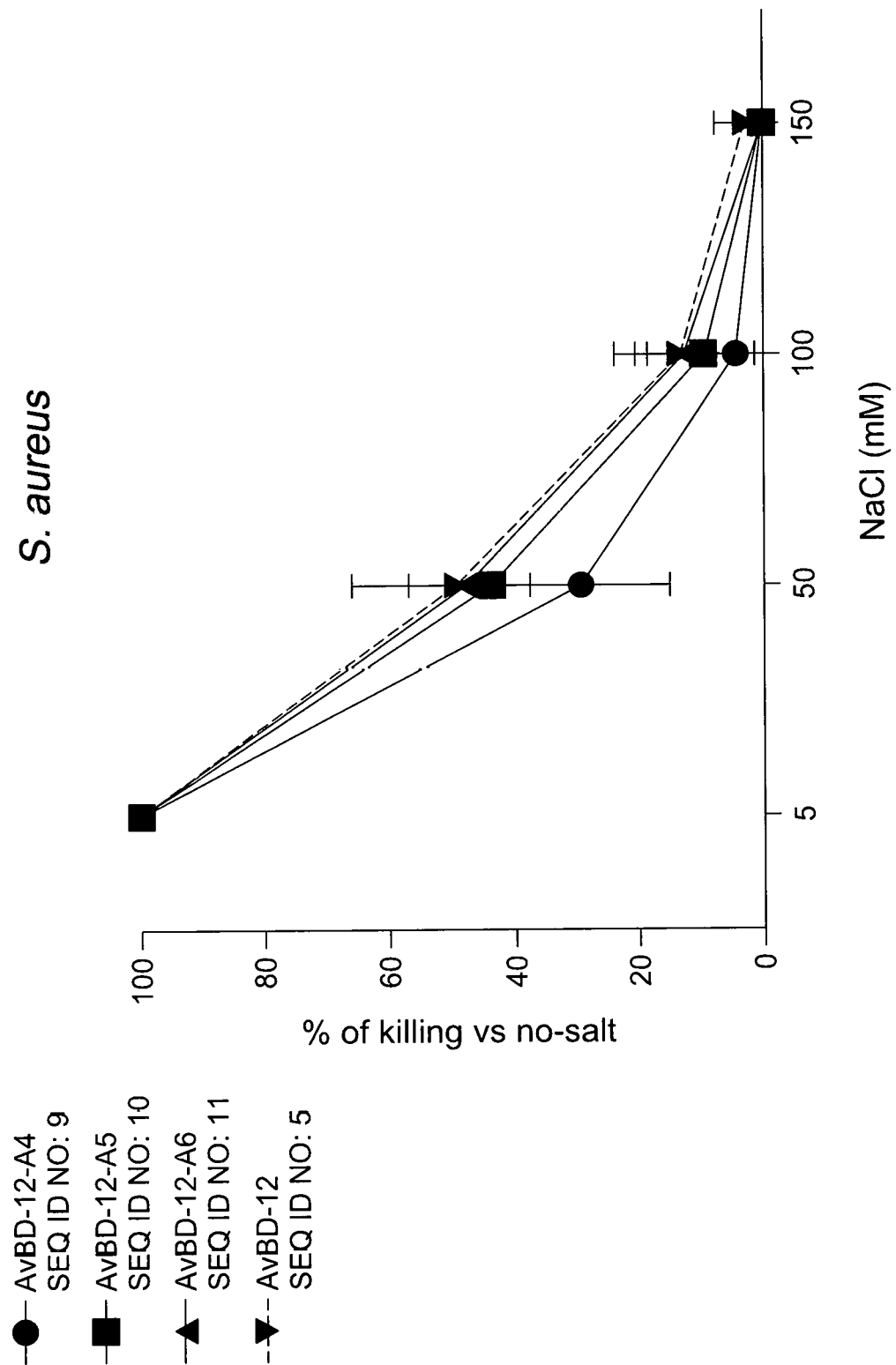
Figure 15A:
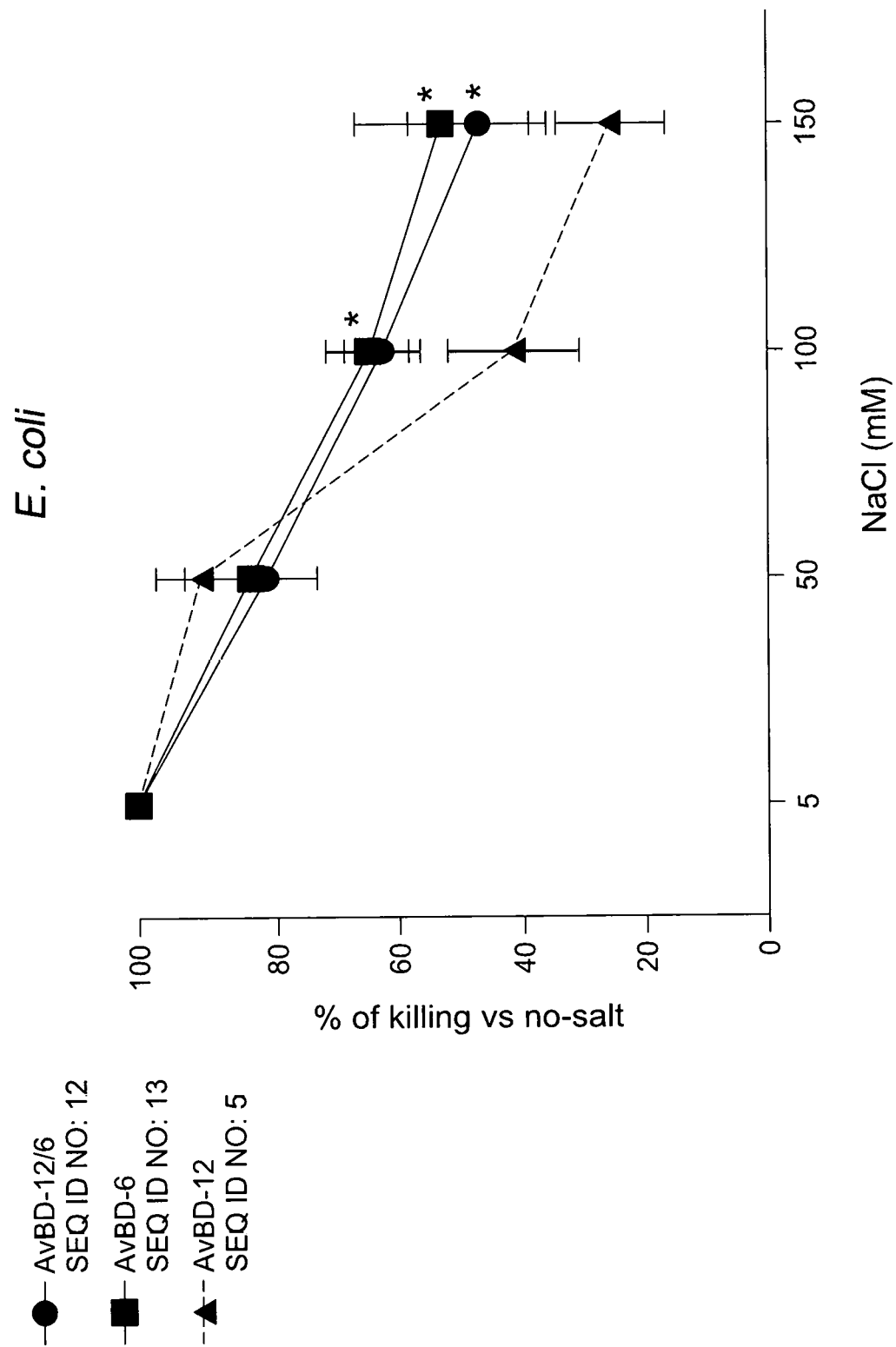
FIGS. 15A-15D are graphs showing the effect of NaCl on the antimicrobial activity of group 3 analogue AvBD-12/6 (SEQ ID NO: 12) when various bacteria were treated with AvBDs in the presence of 5 mM, 50 mM, 100 mM or 150 mM NaCl; in accordance with an aspect of the present invention.
Figure 15B:
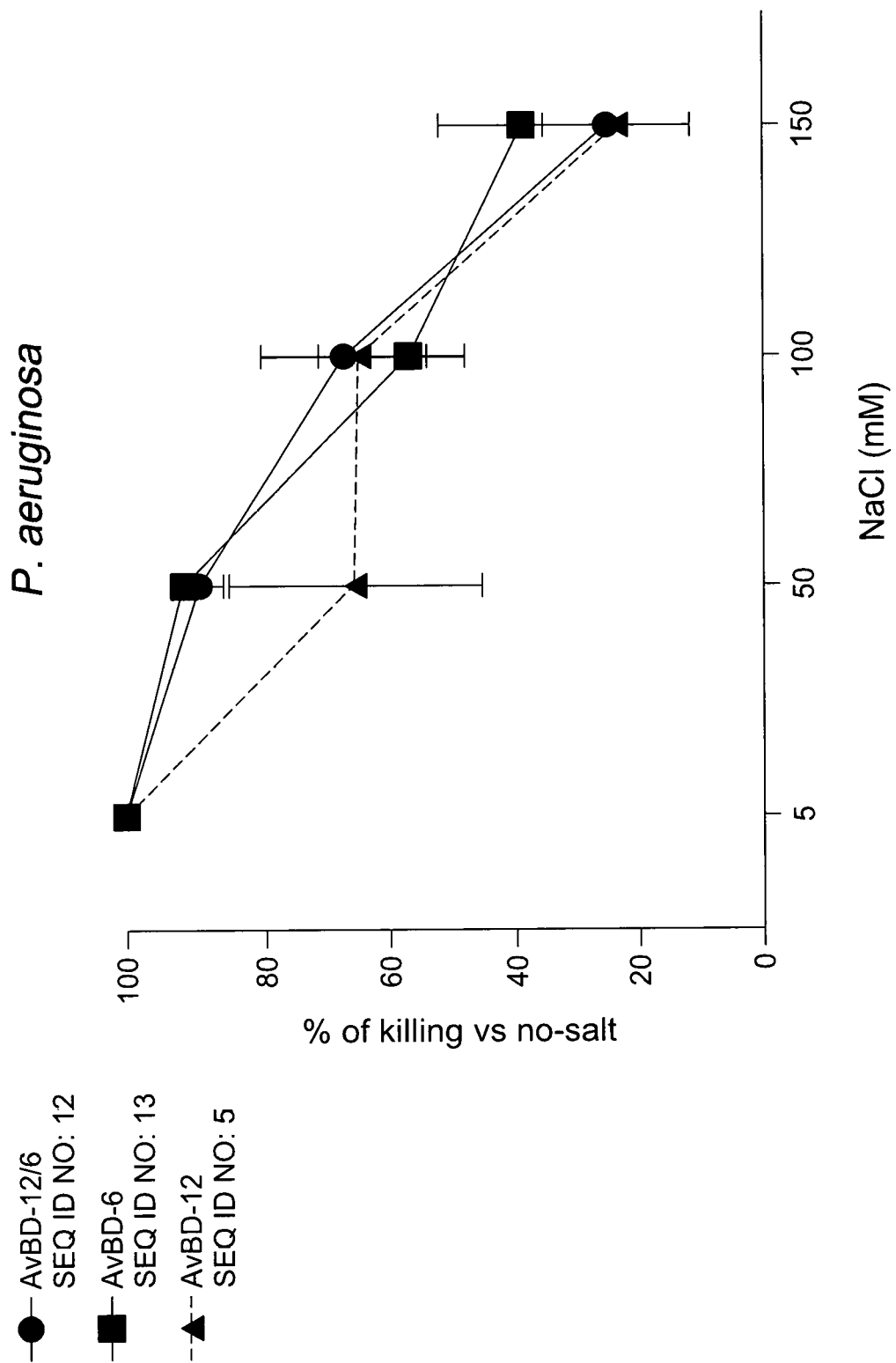
Figure 15C:
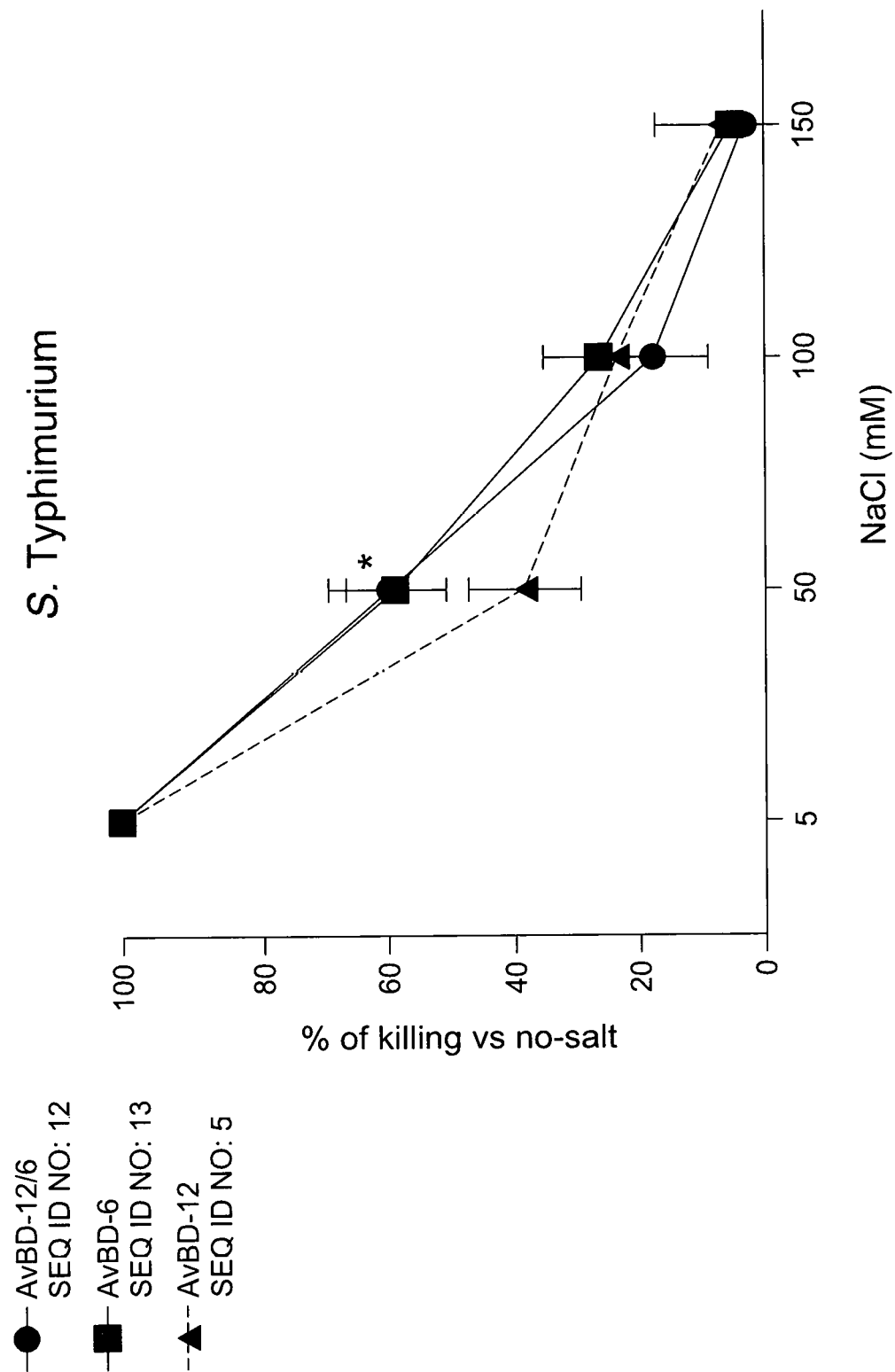
Figure 15D:
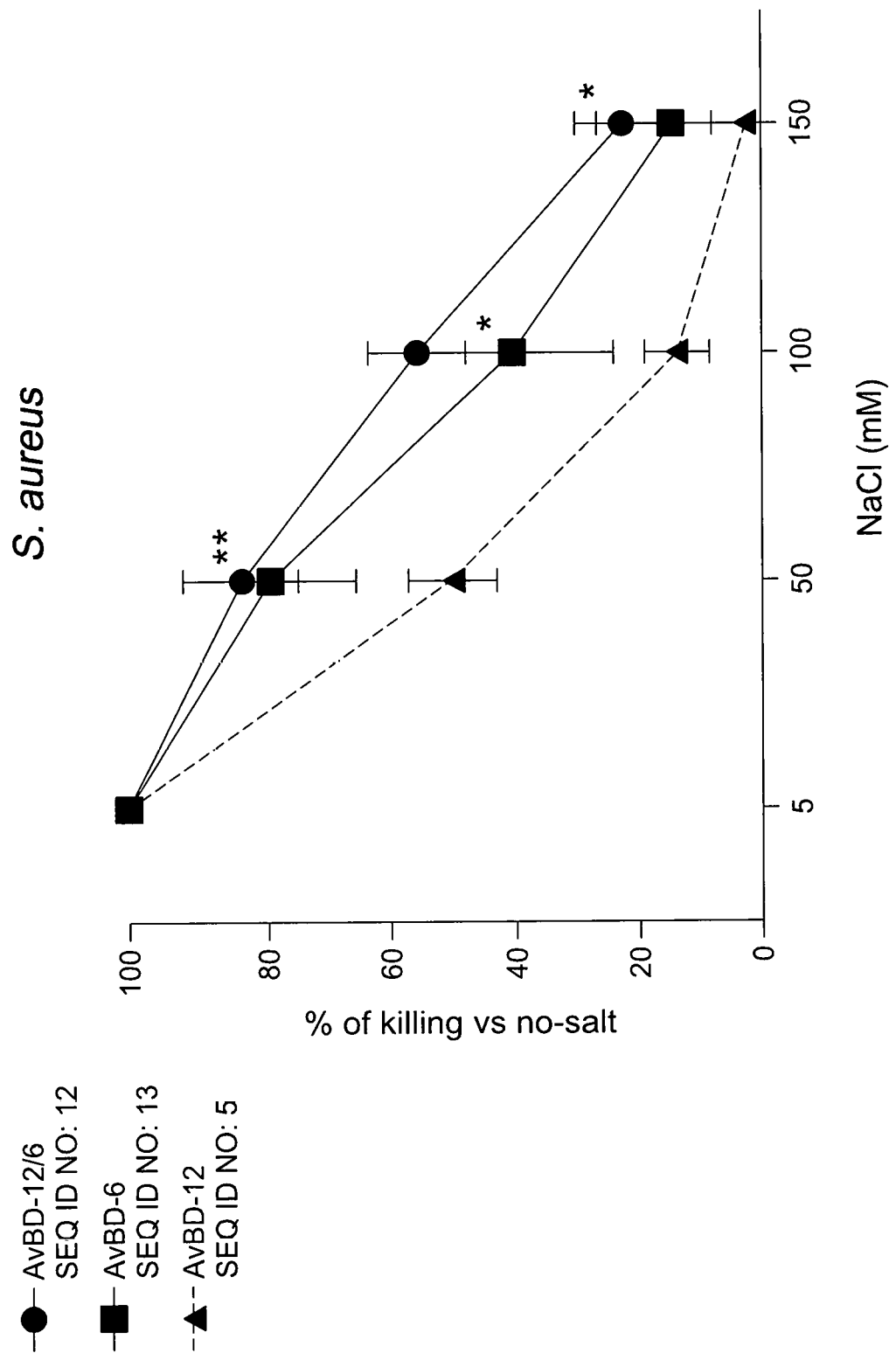

The impact of NaCl on the killing activity of AvBDs (SEQ ID NO: 5, 6, 7, 8, 9, 10, 11, 12, and 13) was assessed at NaCl concentrations ranging from 5 to 150 mM. Increasing NaCl concentration had less adverse impact on the killing activity of the AvBD-12A2 (SEQ ID NO: 7) and AvBD-12A3 (SEQ ID NO: 8) analogues, which exhibited a net positive charge about +9 and hydrophobicity about 40% (FIGS. 13A, 13B, 13C, and 13D). The killing activity of AvBD-12A1 (SEQ ID NO: 6), having a hydrophobicity of about 53%, exhibited some impact from NaCl, compared to AvBD-12 (SEQ ID NO: 5) (FIGS. 13A, 13B, 13C, and 13D). Susceptibility to salts was also influenced by the bacterial species under investigation. At 150 mM NaCl, AvBD-12A2 (SEQ ID NO: 7) and AvBD-12A3 (SEQ ID NO: 8) retained approximately 80% of killing activity against E. coli (FIG. 13A) and P. aeruginosa (FIG. 13B) and retained 30% to 60% of killing activity against S. Typhimurium (FIG. 13C) and S. aureus (FIG. 13D). AvBD-12A4 (SEQ ID NO: 9), AvBD-12A5 (SEQ ID NO: 10), and AvBD-12A6 (SEQ ID NO: 11) exhibited some impact on killing activity due to salt (FIGS. 14A, 14B, 14C, and 14D). The killing activity of AvBD-12/6 (SEQ ID NO: 12) in the presence of salt appeared to more likely resemble the killing activity of AvBD-6 (SEQ ID NO: 13) in salt than that of AvBD-12 (SEQ ID NO: 5) (FIGS. 15A, 15B, 15C, and 15D).

Cell Cytotoxicity Assay and Results

Chicken macrophage cell lines MQ-NCSU and HD11 were maintained in RPMI-1640 media supplemented with 10% fetal bovine serum (FBS), 2% chicken serum, 100 U/ml penicillin and 100 μg/ml streptomycin (Sigma-Aldrich) at 37° C. in humidified air with 5% $CO_2$. CHO-K1 cells were cultured in the same media without 2% chicken serum. For CCR2-transfected CHO-K1 cells, medium was supplemented with 500 μg/ml G418 was added (Sigma-Aldrich). Murine immature dendritic cell line JAWSII (ATCC CRL-11904™) was cultured in Alpha minimum essential medium containing 4 mM L-glutamine, 1 mM sodium pyruvate, 5 ng/ml murine Granulocyte macrophage colony-stimulating factor (GM-CSF), 20% FBS, 100 U/ml penicillin and 100 μg/ml streptomycin at 37° C. in humidified air with 5% $CO_2$. The cell cytotoxicity was determined using the MTT (3-(4, 5-dimethylthiazol-2-yl)-2,5-diphenyltetrazolium bromide cell proliferation assay according to the manufacturer's instruction (Thermo Fisher Scientific). Briefly, cells ($5 \times 10^3$ cells/well) were seeded in 96-well tissue culture plates, incubated overnight and treated with the analogues at concentrations of 4, 16, 64 and 256 μg/ml for 4, 12, 24 and 48 hours at 37° C. After treatment, 20 of 12 mM MTT solution was added to each well. The plate was incubated for 4 hours and read at 540 nm. Viability was expressed as percentage of viable cells relative to the untreated control. The experiments were performed in triplicate.

Figure 18A:
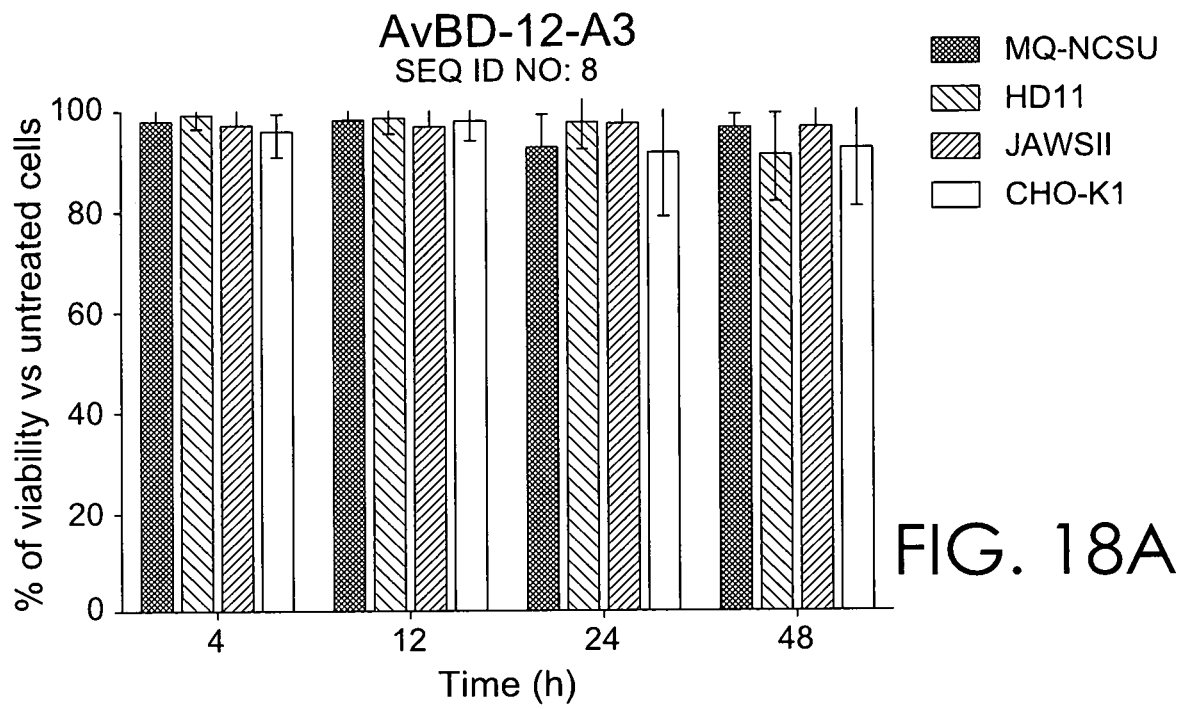
FIGS. 18A-18B are bar graphs showing the cytotoxic effects of 256 µg/ml of AvBD-12A3 (SEQ ID NO: 8) and AvBD-12/6 (SEQ ID NO: 12) on the metabolic activity of MQ-NCSU, HD11, JAWSII and CHO-K1 cells after 4, 12, 24 and 48 hours of incubation, expressed as the percentage of viability relative to an untreated control, in accordance with an aspect of the present invention.
Figure 18B:
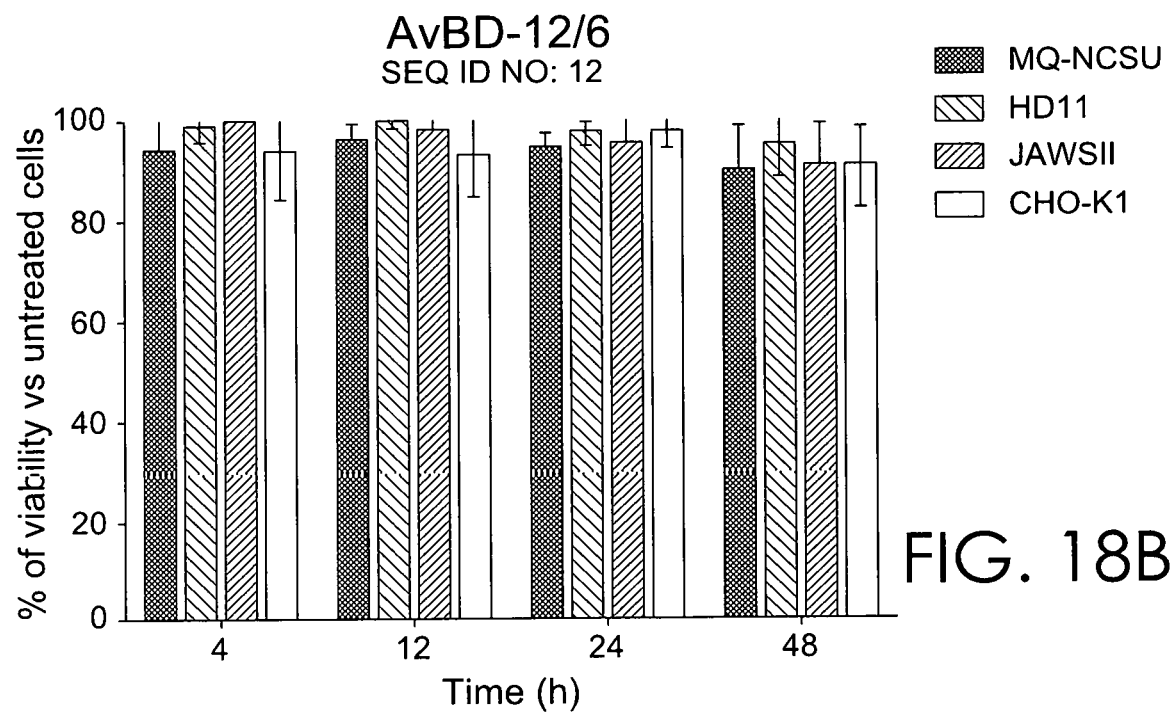

Cell cytotoxicity of AvBD-12A3 (SEQ ID NO: 8) (+9) and AvBD-12/6 (SEQ ID NO: 12) (+5) was determined. Exposure of chicken macrophage cell lines HD11 and MQ-NCSU, murine dendritic cell line JAWSII and CHO-K1 cells to the analogues at concentrations of 4, 16, 64, 256 μg/ml for 4, 12, 24, and 48 hour did not appear to have any effect on cell viability. Data on the highest peptide concentration (256 μg/ml) at various exposure times were presented in FIGS. 18A and 18B.

Example Two

Chemotaxis Assay and Results

Migration of JAWSII and CCR2-CHO-K1 cells in response to the analogues was determined using a 48-well microchemotaxis chamber technique as previously described. For JAWSII cells, chemotaxis buffer (Minimum Essential Medium containing 0.1% BSA, 100 U/ml penicillin, and 100 μg/ml streptomycin) and bacterial peptide N-Formyl-methionyl-leucyl-phenylalanine (fMLF, Sigma-Aldrich) were included as negative and positive controls, respectively. The results were presented as chemotactic index (C.I.). C.I.=number of migrated cells induced by the analogues/number of migrated cells induced by chemotactic buffer. The assay was repeated five times.

Figure 16A:
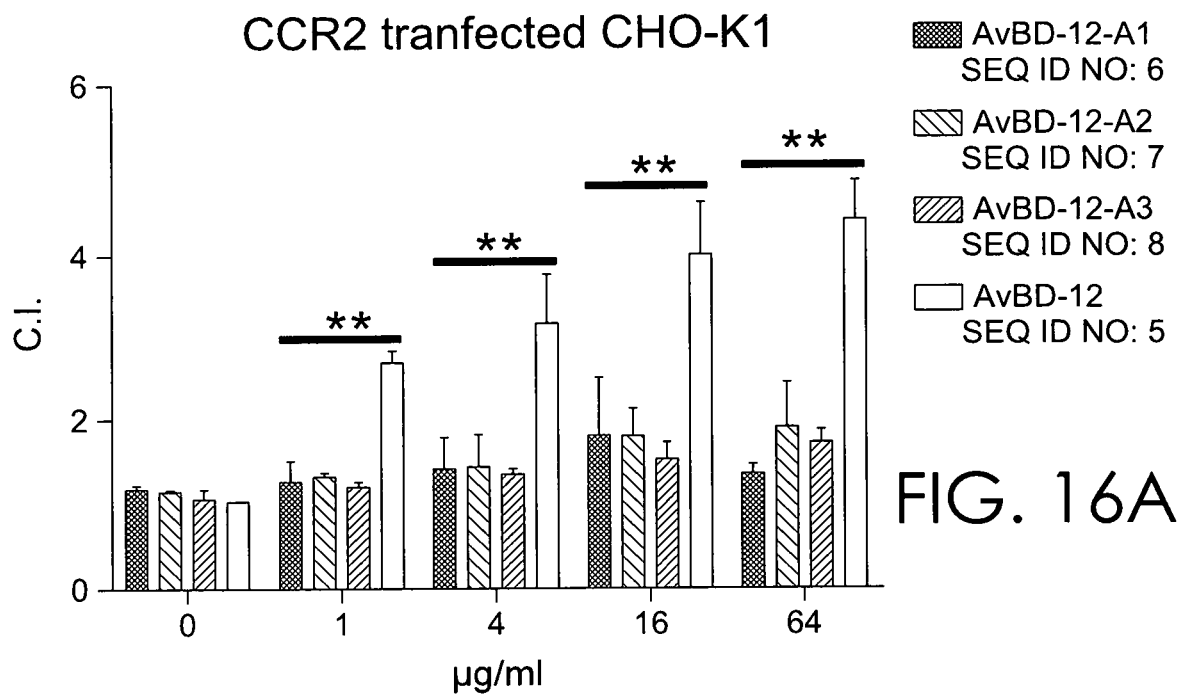
FIG. 16A is a bar graph showing chemotactic activity of AvBD-12A1 (SEQ ID NO: 6), AvBD-12A2 (SEQ ID NO: 7), AvBD-12A3 (SEQ ID NO: 8), and AvBD-12 (SEQ ID NO: 5) for CCR2 transfected CHO-K1 cells, expressed as chemotactic index, in accordance with an aspect of the present invention.
Figure 16B:
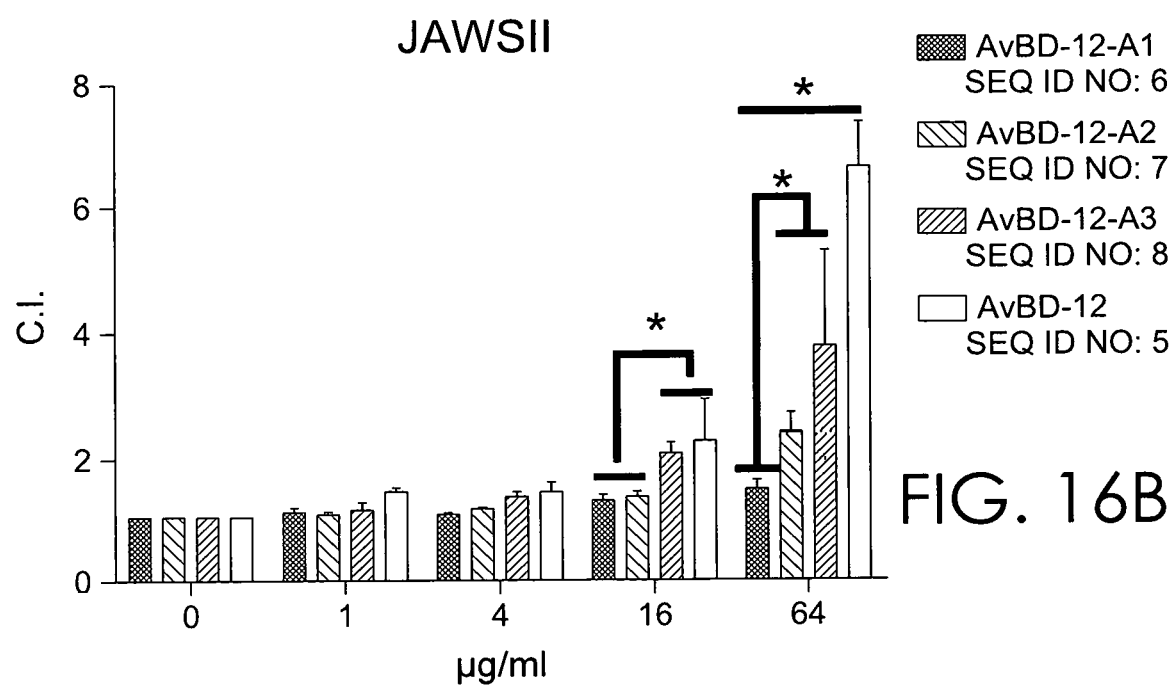
FIG. 16B is a bar graph showing chemotactic activity of AvBD-12A1 (SEQ ID NO: 6), AvBD-12A2 (SEQ ID NO: 7), AvBD-12A3 (SEQ ID NO: 8), and AvBD-12 (SEQ ID NO: 5) for mouse immature dendritic immature JAWSII cells, expressed as chemotactic index, in accordance with an aspect of the present invention.
Figure 16C:
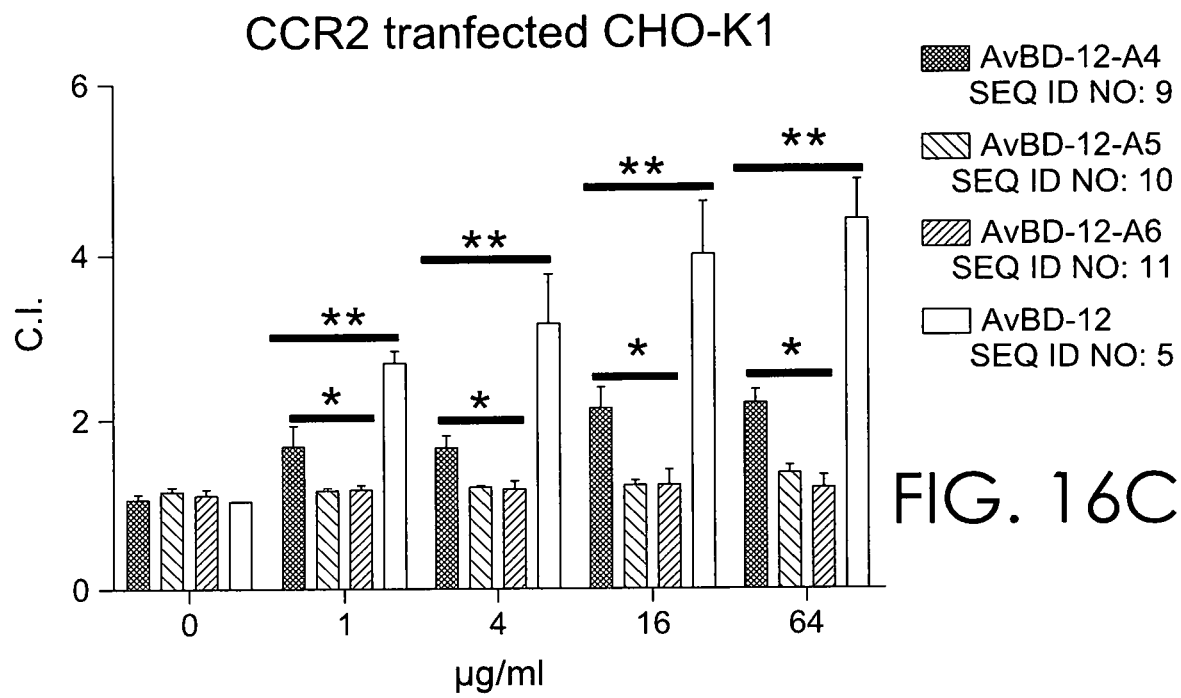
FIG. 16C is a bar graph showing chemotactic activity of AvBD-12A4 (SEQ ID NO: 9), AvBD-12A5 (SEQ ID NO: 10), AvBD-12A6 (SEQ ID NO: 11), and AvBD-12 (SEQ ID NO: 5) for CCR2 transfected CHO-K1 cells, expressed as chemotactic index, in accordance with an aspect of the present invention.
Figure 16D:
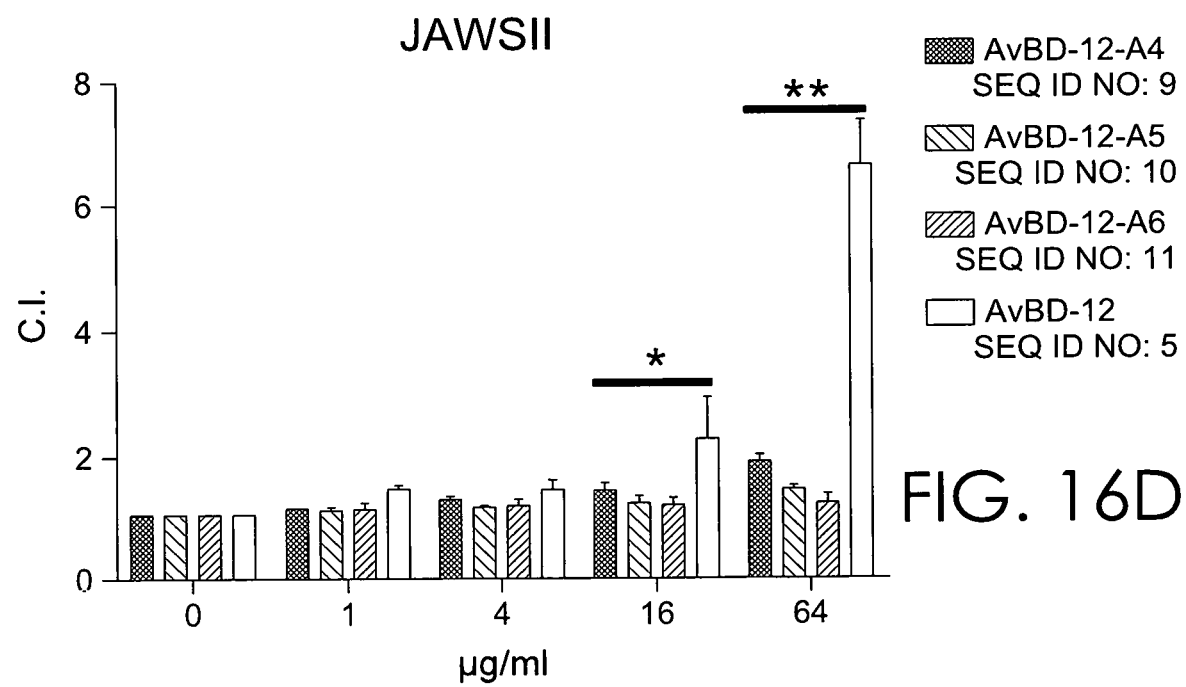
FIG. 16D is a bar graph showing chemotactic activity of AvBD-12A4 (SEQ ID NO: 9), AvBD-12A5 (SEQ ID NO: 10), AvBD-12A6 (SEQ ID NO: 11), and AvBD-12 (SEQ ID NO: 5) for mouse immature dendritic immature JAWSII cells, expressed as chemotactic index, in accordance with an aspect of the present invention.
Figure 16E:
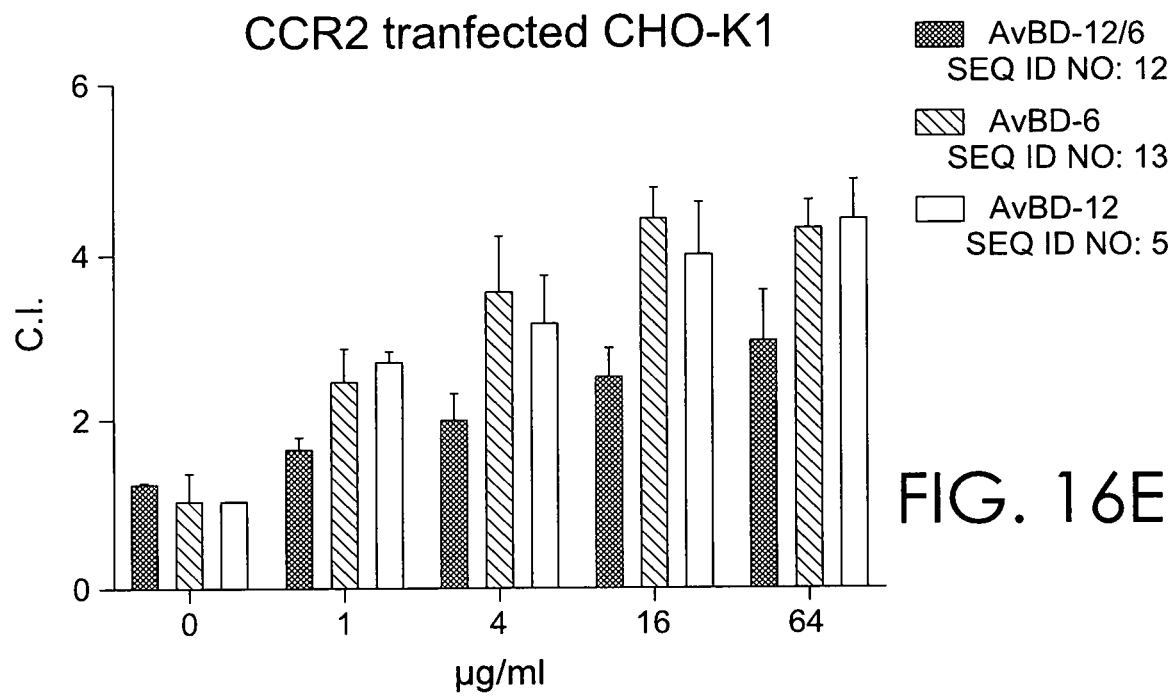
FIG. 16E is a bar graph showing chemotactic activity of AvBD-12/6 (SEQ ID NO: 12), AvBD-6 (SEQ ID NO: 13), and AvBD-12 (SEQ ID NO: 5) for CCR2 transfected CHO-K1 cells, expressed as chemotactic index, in accordance with an aspect of the present invention.
Figure 16F:
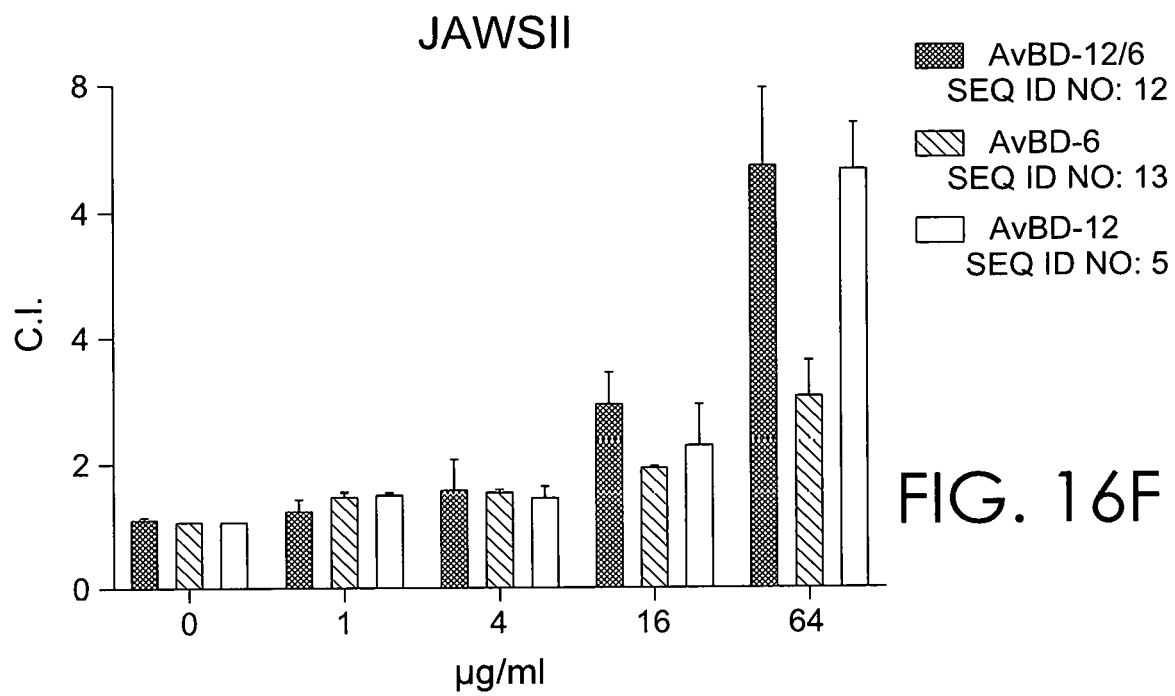
FIG. 16F is a bar graph showing chemotactic activity of AvBD-12/6 (SEQ ID NO: 12), AvBD-6 (SEQ ID NO: 13), and AvBD-12 (SEQ ID NO: 5) for mouse immature dendritic immature JAWSII cells, expressed as chemotactic index, in accordance with an aspect of the present invention.

Group 1 analogues AvBD-12A1 (SEQ ID NO: 6), AvBD-12A2 (SEQ ID NO: 7), and AvBS-12A3 (SEQ ID NO: 8), showed mild or little chemotactic activity for CCR2-CHO cells (FIG. 16A). AvBD-12A2 (SEQ ID NO: 7) and AvBD-12A3 (SEQ ID NO: 8) at 64 μg/ml demonstrated mild (C.I.=2.37; 35.90/o of wild type) and modest (C.I.=3.74; 56.6% of wild type) chemotactic activity, respectively, for JAWSII cells (FIG. 16B). Analogues AvBD-12A4 (SEQ ID NO: 9) exhibited mild chemotactic activity for CCR2-CHO (C.I.=1.48 to 2.18) and JAWSII cells (C.I.=1.05 to 1.86), relative to the chemotactic index of parent peptide AvBD-12 (SEQ ID NO: 5) ($p<0.01$, FIGS. 16C and 16D). AvBD-12A5 (SEQ ID NO: 10) and AvBD-12A6 (SEQ ID NO: 11) did not appear to exhibit chemotactic activity for CCR2-CHO-K1 and JAWSII cells (FIGS. 16C and 16D). The Group 3 analogue, AvBD-12/6 (SEQ ID NO: 12), retained the chemotactic function of the backbone peptide AvBD-12 (SEQ ID NO: 5) (FIGS. 16E and 16F).

Scanning Electron Microscopy (SEM)

SEM was performed according the procedure described by Coho et al. (Muscol. Immunology,2015, 8(6):1360-1372). *S. Typhimurium* were cultured in Mueller-Hinton (MH) broth to mid-log phase and harvested by centrifugation at 5000 g for 10 minutes. Cell pellets were washed twice with 10 mM PBS and re-suspended at a final number of $10^8$ CFU. The cell suspension was incubated with 1×MIC-1s of AvBD-12A3 (SEQ ID NO: 8), AvBD-12/6 (SEQ ID NO: 12) and wild-type AvBD-6 (SEQ ID NO: 13) and AvBD-12 (SEQ ID NO: 5) at 37° C. for 30 minutes. Bacterial pellets were fixed in 500 ml of 2.5% (v/v) glutaraldehyde in 0.2 M cacodylate buffer at 4° C. overnight, washed twice with 0.2 M cacodylate buffer and dehydrated through ethanol gradient (30%, 50%, 70%, 90%, 100% and 100%) for 15 minutes in each gradient. The samples were then transferred to a mixture (1:1, v/v) of ethanol and tertiary butanol and then pure tertiary butanol for 20 minutes in each. After gold coating, the specimens were observed using a scanning electron microscope (Hitachi S-4700, Japan).

Figure 17C:
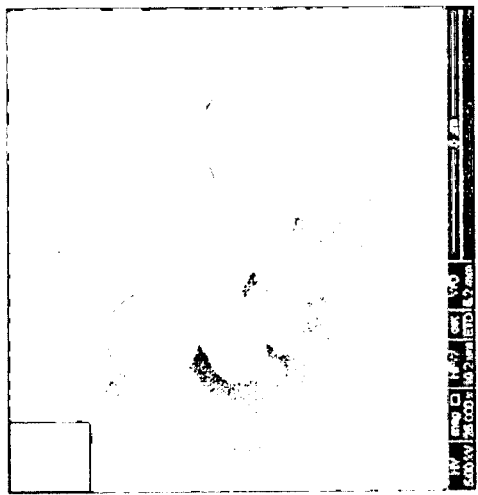
FIG. 17C depicts a scanning electron microscopy (SEM) image of mid-logarithmic-phase *S. Typhimurium* cells ($10^8$ CFU) treated with AvBD-12 (SEQ ID NO: 5) at a final concentration of 1×MIC-1s for 30 min, in accordance with an aspect of the present invention.
Figure 17F:
FIG. 17F depicts a scanning electron microscopy (SEM) image of mid-logarithmic-phase *S. Typhimurium* cells treated with PBS, in accordance with an aspect of the present invention.
Figure 17B:
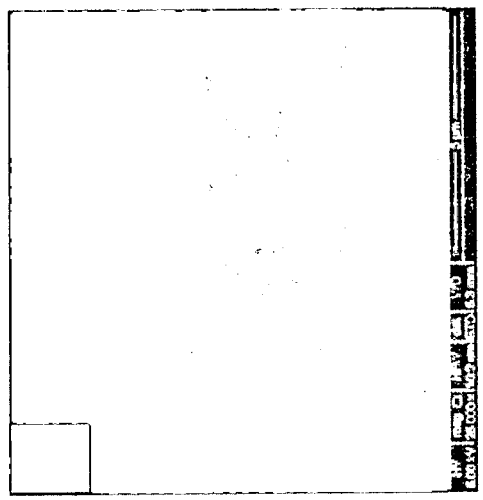
FIG. 17B depicts a scanning electron microscopy (SEM) image of mid-logarithmic-phase *S. Typhimurium* cells ($10^8$ CFU) treated with AvBD-12/6 (SEQ ID NO: 12) at a final concentration of 1×MIC-1s for 30 min, in accordance with an aspect of the present invention.
Figure 17E:
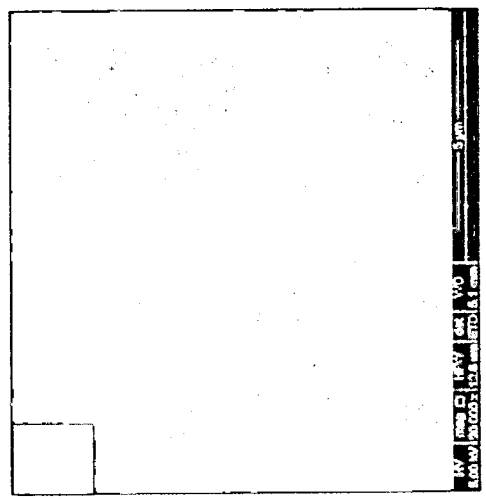
FIG. 17E depicts a scanning electron microscopy (SEM) image of stationary phase *S. Typhimurium* cells, in accordance with an aspect of the present invention.
Figure 17A:
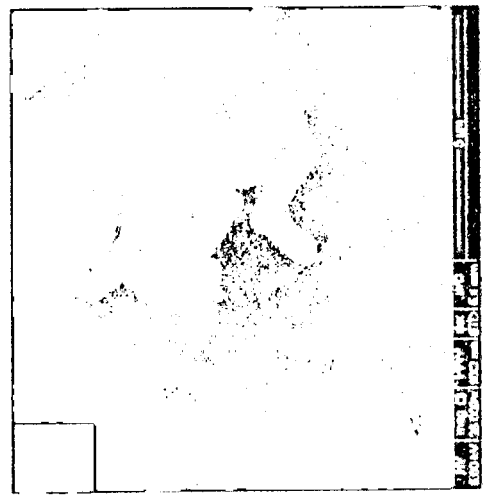
FIG. 17A depicts a scanning electron microscopy (SEM) image of mid-logarithmic-phase *S. Typhimurium* cells ($10^8$ CFU) treated with AvBD-12A3 (SEQ ID NO: 8) at a final concentration of 1×MIC-1s for 30 min. in accordance with an aspect of the present invention.
Figure 17D:
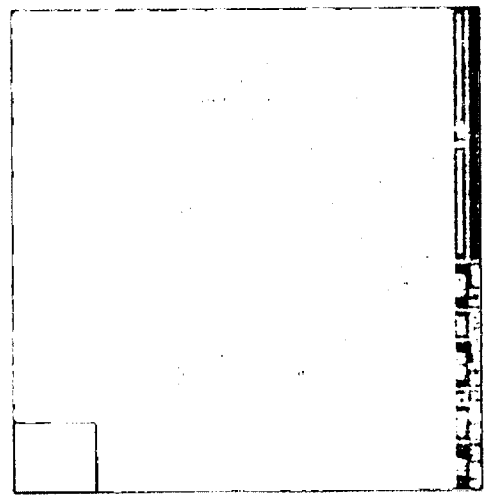
FIG. 17D depicts a scanning electron microscopy (SEM) image of mid-logarithmic-phase *S. Typhimurium* cells ($10^8$ CFU) treated with AvBD-6 (SEQ ID NO: 13) at a final concentration of 1×MIC-1s for 30 min, in accordance with an aspect of the present invention.

Bacteria treated with AvBD-12A3 (SEQ ID NO: 8) (FIG. 17A), AvBD-12/6 (SEQ ID NO: 12) (FIG. 17B), AvBD-12 (SEQ ID NO: 5) (FIG. 17C), and AvBD-6 (SEQ ID NO: 13) (FIG. 17D) displayed cell membrane damage. Normal death of bacteria from stationary phase (FIG. 17E) showed loss of intracellular content and uniform membrane structure. Bacteria treated with PBS showed normal size and intact structure (FIG. 17F).

The present invention has been described in relation to particular aspects, which are intended in all respects to be illustrative rather than restrictive. Further, the present invention is not limited to these aspects, but variations and modifications may be made without departing from the scope of the present invention.

The present disclosure can also be described in accordance with the following numbered clauses:

Clause 1. A composition comprising: an antimicrobial agent, the antimicrobial agent comprising a polypeptide having less than 40 amino acids, and a net positive charge of at least about 3 at a pH of 7.0 and a hydrophobicity of greater than 25%.

Clause 2. The composition according to clause 1, wherein the polypeptide has a net positive charge of from 3-9.

Clause 3. The composition according to any of clauses 1 and 2, wherein the polypeptide has a net positive charge of from 4-7.

Clause 4. The composition according to any of clauses 1-3, wherein the polypeptide has a hydrophobicity of about 25% to about 50%.

Clause 5. The composition according to any of clauses 1-4, wherein the polypeptide has at least 10 amino acids.

Clause 6. The composition according to any of clauses 1-5, wherein the polypeptide has less than 30 amino acids.

Clause 7. The composition according to any of clauses 1-6, wherein the polypeptide has 10 to 30 amino acids.

Clause 8. The composition according to any of clauses 1-7, wherein the polypeptide has at least one C-terminal tryptophan amino acid.

Clause 9. The composition according to any of clauses 1-8, wherein the polypeptide has at least three C-terminal tryptophan amino acids.

Clause 10. The composition according to any of clauses 1-9, wherein the polypeptide comprises L-amino acids.

Clause 11. The composition according to any of clauses 1-9, wherein the polypeptide comprises D-amino acids.

Clause 12. The composition according to any of clauses 1-11, wherein at least a portion of the polypeptide is adapted to form an alpha-helical structure in physiological conditions.

Clause 13. The composition according to any of clauses 1-12, wherein the polypeptide comprises an amino acid sequence having at least 80%, 90%, 95%, and/or 99% sequence identity to at least one of the following:

```
                                    (SEQ ID NO: 1)
RKFLRRRGEVAHFSQKSLGLYCWWW;

(SEQ ID NO: 2)
PIHRRIPPRWPRLKRRW;

(SEQ ID NO: 3)
LRRLKPLIRPWLRPLRRWWW;
and (SEQ ID NO: 4)
RRRWRKRRWWW.
```

Clause 14. The composition according to any of clauses 1-12, wherein the polypeptide is selected from the group consisting of:

```
                                    (SEQ ID NO: 1)
RKFLRRRGEVAHFSQKSLGLYCWWW;

(SEQ ID NO: 2)
PIHRRIPPRWPRLKRRW;

(SEQ ID NO: 3)
LRRLKPLIRPWLRPLRRWWW;
and (SEQ ID NO: 4)
RRRWRKRRWWW.
```

Clause 15. The composition according to any of clauses 1-14, wherein an N-terminal amino acid of the polypeptide is acetylated.

Clause 16. The composition according to any of clauses 1-15, wherein a C-terminal amino acid of the polypeptide is amidated.

Clause 17. The composition according to any of clauses 1-16, further comprising a pharmaceutically acceptable carrier.

Clause 18. The composition according to any of clauses 1-17, wherein the polypeptide exhibits a Minimum Inhibitory Concentration of less than 250 µg/ml, 150 µg/ml, and/or 75 µg/ml against *P. aeruginosa* as determined according to the Antimicrobial Activity Assay specified Example One.

Clause 19. The composition according to any of clauses 1-18, wherein the polypeptide exhibits a Minimum Inhibitory Concentration of less than 250 µg/ml, 150 µg/ml, and/or 75 µg/ml against *S. pseudintermedius* as determined according to the Antimicrobial Activity Assay specified in Example One.

Clause 20. The composition according to any of clauses 1-19, for use as: an antibiotic or component of an antibiotic composition; a food preservative or component of a food preservative composition; a vaccine preservative or component of a vaccine preservative composition; and/or a vaccine adjuvant or a component of a vaccine adjuvant composition.

Clause 21. A composition comprising: an antimicrobial agent, the antimicrobial agent comprising: a) a polypeptide having a sequence with at least 80%, 90%, 95%, 99%, or 100% sequence identity to one or more of:

RKFLRRRGEVAHFSQKSLGLYCWWW (SEQ ID NO: 1); PIHRRIPPRWPRLKRRW (SEQ ID NO: 2); LRRLKP-LIRPWLRPLRRWWW (SEQ ID NO: 3); and RRRWRKRRWWW (SEQ ID NO: 4), or b) a peptidomimetic of the polypeptide.

Clause 22. The composition according to clause 21, wherein the peptidomimetic comprises one or more D-amino acids.

Clause 23. The composition according to any of clauses 21 and 22, wherein the peptidomimetic comprises at least one peptoid.

Clause 24. The composition according to any of clauses 21-23, wherein the peptidomimetic comprises at least one β-peptide.

Clause 25. The composition according to any of clauses 21-24, wherein an N-terminal amino acid of the polypeptide is acetylated.

Clause 26. The composition according to any of clauses 21-25, wherein a C-terminal amino acid of the polypeptide is amidated.

Clause 27. The composition according to any of clauses 21-26, further comprising a pharmaceutically acceptable carrier.

Clause 28. The composition according to any of clauses 21-27, wherein the polypeptide exhibits a Minimum Inhibitory Concentration of less than 250 µg/ml, 150 µg/ml, and/or 75 µg/ml against *P. aeruginosa* as determined according to the Antimicrobial Activity Assay specified in Example One.

Clause 29. The composition according to any of clauses 21-28, wherein the polypeptide exhibits a Minimum Inhibitory Concentration of less than 250 µg/ml, 150 µg/ml, and/or 75 µg/ml against *S. pseudintermedius* as determined according to the Antimicrobial Activity Assay specified in Example One.

Clause 30. The composition according to any of clauses 21-29, for use as: an antibiotic or component of an antibiotic composition; a food preservative or component of a food preservative composition; a vaccine preservative or component of a vaccine preservative composition; and/or a vaccine adjuvant or a component of a vaccine adjuvant composition.

Clause 31. A composition comprising: a synthetic avian beta-defensin analogue comprising a polypeptide having a net positive charge of at least about 5 and a hydrophobicity greater than about 33%.

Clause 32. The composition according to clause 31, wherein the polypeptide has a net positive charge of about 7 to about 9.

Clause 33. The composition according any of clauses 31 and 32, wherein the polypeptide has a net positive charge of about 9.

Clause 34. The composition according any of clauses 31-33, the polypeptide having a hydrophobicity of about 40% or more.

Clause 35. The composition according any of clauses 31-34, the polypeptide having about 40 to about 50 amino acids.

Clause 36. The composition according to any of clauses 31-35, wherein the polypeptide has about 70% to about 90% sequence identity to the wild type avian beta-defensin 12 polypeptide sequence:

(SEQ ID NO: 5)
GPDSCNHDRGLCRVGNCNPGEYLAKYCFEPVILCCKPLSPTPTKT.

Clause 37. The composition according to any of clauses 31-36, wherein the polypeptide does not contain cysteine.

Clause 38. The composition according to any of clauses 31-37, wherein the polypeptide comprises a sequence having at least about 90% sequence identity to one of:

(SEQ ID NO: 6)
GPHSANHVRGLARVGNANPGLYLAKYAFIPVILAAKPLSPTPTKT;

(SEQ ID NO: 7)
GPRSSNHKRGLSRVGNSNPGKYLAKYAFRPVILAAKPLSPTPTKT;
and (SEQ ID NO: 8)
GPRSANHKRGLARVGNANPGKYLAKYSFRPVILSSKPLSPTPTKT.

Clause 39. The composition according to any of clauses 31-38, wherein the polypeptide is selected from the group consisting of:

(SEQ ID NO: 6)
GPHSANHVRGLARVGNANPGLYLAKYAFIPVILAAKPLSPTPTKT;

(SEQ ID NO: 7)
GPRSSNHKRGLSRVGNSNPGKYLAKYAFRPVILAAKPLSPTPTKT;
and (SEQ ID NO: 8)
GPRSANHKRGLARVGNANPGKYLAKYSFRPVILSSKPLSPTPTKT.

Clause 40. The composition according to any of clauses 31-39, wherein the composition exhibits about an 80% killing of *E. coli* in 150 mM NaCl when the polypeptide is present in a concentration of 16 µg/ml, and/or exhibits about an 80% killing of *P. aeruginosa* in 150 mM NaCl when the polypeptide is present in a concentration of 32 µg/ml, as determined by the Antimicrobial Activity Assay of Example Two.

Clause 41. A composition comprising: a synthetic avian beta-defensin analogue comprising a polypeptide having about 30 to about 50 amino acids, wherein the polypeptide has a net positive charge of about 7 to about 9 and a hydrophobicity of at least about 40%, wherein the polypeptide exhibits about an 80% killing of *E. coli* in 150 mM NaCl, when present in a concentration of 16 µg/ml, and/or exhibits an 80% killing of *P. aeruginosa* in 150 mM NaCl, when present in a concentration of 32 µg/ml, as determined by the Antimicrobial Activity Assay of Example Two.

Clause 42. The composition according to clause 41, wherein the polypeptide comprises a sequence selected from the group consisting of:

(SEQ ID NO: 6)
GPHSANHVRGLARVGNANPGLYLAKYAFIPVILAAKPLSPTPTKT;

(SEQ ID NO: 7)
GPRSSNHKRGLSRVGNSNPGKYLAKYAFRPVILAAKPLSPTPTKT;

(SEQ ID NO: 8)
GPRSANHKRGLARVGNANPGKYLAKYSFRPVILSSKPLSPTPTKT;

and a sequence having at least about 90% sequence identity to one of SEQ ID NOs: 6, 7, or 8.

Clause 43. The composition according to any of clauses 41 and 42, wherein the polypeptide does not contain cysteine.

Clause 44. An antimicrobial composition comprising: a pharmaceutically acceptable carrier; and a synthetic avian beta-defensin analogue comprising a polypeptide having a net positive charge of at least about 5 and a hydrophobicity greater than about 33%.

Clause 45. The antimicrobial composition according to clause 44, wherein the polypeptide has a net positive charge of about 9 and a hydrophobicity of about 40% or more.

Clause 46. The antimicrobial composition according to any of clauses 44 and 45, wherein the polypeptide does not contain cysteine.

Clause 47. The antimicrobial composition according to any of clauses 44-46, wherein the polypeptide has about 70% to about 90% sequence identity to the wild type avian beta-defensin 12 polypeptide sequence:

```
                                            (SEQ ID NO: 5)
GPDSCNHDRGLCRVGNCNPGEYLAKYCFEPVILCCKPLSPTPTKT.
```

Clause 48. The antimicrobial composition according to any of clauses 44-47, wherein the polypeptide comprises a sequence having at least about 90% sequence identity to one of:

```
                                            (SEQ ID NO: 6)
GPHSANHVRGLARVGNANPGLYLAKYAFIPVILAAKPLSPTPTKT;

(SEQ ID NO: 7)
GPRSSNHKRGLSRVGNSNPGKYLAKYAFRPVILAAKPLSPTPTKT;
and (SEQ ID NO: 8)
GPRSANHKRGLARVGNANPGKYLAKYSFRPVILSSKPLSPTPTKT.
```

Clause 49. The antimicrobial composition according to any of clauses 44-48, wherein the antimicrobial composition exhibits about an 80% killing of *E. coli* in 150 mM NaCl, when the polypeptide is present in a concentration of 16 μg/ml, and/or exhibits about an 80% killing of *P. aeruginosa* in 150 mM NaCl, when the linear polypeptide is present in a concentration of 32 μg/ml, as determined by the Antimicrobial Activity Assay of the Second Example.

Clause 50. The antimicrobial composition according to any of clauses 44-49, wherein the polypeptide is selected from the group consisting of:

```
                                            (SEQ ID NO: 6)
GPHSANHVRGLARVGNANPGLYLAKYAFIPVILAAKPLSPTPTKT;

(SEQ ID NO: 7)
GPRSSNHKRGLSRVGNSNPGKYLAKYAFRPVILAAKPLSPTPTKT;
and (SEQ ID NO: 8)
GPRSANHKRGLARVGNANPGKYLAKYSFRPVILSSKPLSPTPTKT.
```

Clause 51. The composition according to any one of clauses 31-43, wherein the polypeptide comprises L-amino acids.

Clause 52. The antimicrobial composition according to any one of clauses 44-50, wherein the polypeptide comprises L-amino acids.

Clause 53. The composition according to any one of clauses 31-43, wherein the polypeptide comprises D-amino acids.

Clause 54. The antimicrobial composition according to any one of clauses 44-50, wherein the polypeptide comprises D-amino acids.

Clause 55. The composition according to any one of clauses 31-43, 51, and 53, for use as: an antibiotic or component of an antibiotic composition; a food preservative or component of a food preservative composition; a vaccine preservative or component of a vaccine preservative composition; and/or a vaccine adjuvant or a component of a vaccine adjuvant composition.

Clause 56. A composition comprising: a synthetic avian beta-defensin analogue comprising: a) a polypeptide having a net positive charge of at least about 5 and a hydrophobicity greater than about 33%; or b) a peptidomimetic of the polypeptide.

Clause 57. The composition according to clause 56, wherein the peptidomimetic comprises D-amino acids.

---

What is claimed is:

1. A composition comprising:
an antimicrobial agent, the antimicrobial agent comprising a polypeptide having less than 40 amino acids, and a net positive charge of at least 3 at a pH of 7.0 and a hydrophobicity of greater than 25%, wherein the polypeptide comprises an amino acid sequence having at least 80% sequence identity to at least one of the following:

RKFLRRRGEVAHFSQKSLGLYCWWW; (SEQ ID NO: 1)

PIHRRIPPRWPRLKRRW; (SEQ ID NO: 2)

LRRLKPLIRPWLRPLRRWWW; (SEQ ID NO: 3)
or

RRRWRKRRWWW. (SEQ ID NO: 4)

2. The composition of claim 1, wherein the polypeptide exhibits a Minimum Inhibitory Concentration of less than 250 µg/ml against *P. aeruginosa* as determined according to the Antimicrobial Activity Assay.

3. The composition of claim 1, wherein the polypeptide has a sequence with at least 95% sequence identity to one or more of:

RKFLRRRGEVAHFSQKSLGLYCWWW; (SEQ ID NO: 1)

PIHRRIPPRWPRLKRRW; (SEQ ID NO: 2)

LRRLKPLIRPWLRPLRRWWW; (SEQ ID NO: 3)
or

RRRWRKRRWWW. (SEQ ID NO: 4)

4. The composition of claim 1, wherein the polypeptide has a sequence with at least 99% sequence identity to one or more of:

RKFLRRRGEVAHFSQKSLGLYCWWW; (SEQ ID NO: 1)

PIHRRIPPRWPRLKRRW; (SEQ ID NO: 2)

LRRLKPLIRPWLRPLRRWWW; (SEQ ID NO: 3)
or

RRRWRKRRWWW. (SEQ ID NO: 4)

5. A composition comprising:
an antimicrobial agent, the antimicrobial agent comprising:
a) a polypeptide having a sequence with at least 80% sequence identity to one or more of:

RKFLRRRGEVAHFSQKSLGLYCWWW; (SEQ ID NO: 1)

PIHRRIPPRWPRLKRRW; (SEQ ID NO: 2)
or

LRRLKPLIRPWLRPLRRWWW; (SEQ ID NO: 3)

or
b) a peptidomimetic of the polypeptide.

6. The composition of claim 5, wherein an N-terminal amino acid of the polypeptide is acetylated.

7. The composition of claim 5, wherein a C-terminal amino acid of the polypeptide is amidated.

8. The composition of claim 5, further comprising a pharmaceutically acceptable carrier.

9. The composition of claim 5, wherein the polypeptide exhibits a Minimum Inhibitory Concentration of less than 250 µg/ml against *P. aeruginosa* as determined according to the Antimicrobial Activity Assay.

10. The composition of claim 5, wherein the polypeptide has less than 40 amino acids, a net positive charge of at least 3 at a pH of 7.0, and a hydrophobicity of greater than 25%.

11. The composition of claim 5, wherein the polypeptide has a sequence with at least 95% sequence identity to one or more of:

RKFLRRRGEVAHFSQKSLGLYCWWW; (SEQ ID NO: 1)

PIHRRIPPRWPRLKRRW; (SEQ ID NO: 2)
or

LRRLKPLIRPWLRPLRRWWW. (SEQ ID NO: 3)

12. The composition of claim 5, wherein the polypeptide has a sequence with at least 99% sequence identity to one or more of:

```
                                       (SEQ ID NO: 1)
RKFLRRRGEVAHFSQKSLGLYCWWW;

(SEQ ID NO: 2)
PIHRRIPPRWPRLKRRW;
or (SEQ ID NO: 3)
LRRLKPLIRPWLRPLRRWWW.
```

13. The composition of claim 5, wherein the polypeptide is one of:

```
                                       (SEQ ID NO: 1)
RKFLRRRGEVAHFSQKSLGLYCWWW;

(SEQ ID NO: 2)
PIHRRIPPRWPRLKRRW;
or (SEQ ID NO: 3)
LRRLKPLIRPWLRPLRRWWW.
```

14. A composition comprising:
an antimicrobial agent, the antimicrobial agent comprising:
  a) a polypeptide having a sequence with at least 95% sequence identity to one or more of:

```
                                       (SEQ ID NO: 1)
RKFLRRRGEVAHFSQKSLGLYCWWW;

(SEQ ID NO: 2)
PIHRRIPPRWPRLKRRW;

(SEQ ID NO: 3)
LRRLKPLIRPWLRPLRRWWW;
or (SEQ ID NO: 4)
RRRWRKRRWWW;
``` or
  b) a peptidomimetic of the polypeptide.

15. The composition of claim 14, wherein an N-terminal amino acid of the polypeptide is acetylated.

16. The composition of claim 14, wherein a C-terminal amino acid of the polypeptide is amidated.

17. The composition of claim 14, further comprising a pharmaceutically acceptable carrier.

18. The composition of claim 14, wherein the polypeptide has a sequence with at least 99% sequence identity to one or more of:

```
                                       (SEQ ID NO: 1)
RKFLRRRGEVAHFSQKSLGLYCWWW;

(SEQ ID NO: 2)
PIHRRIPPRWPRLKRRW;

(SEQ ID NO: 3)
LRRLKPLIRPWLRPLRRWWW;
or (SEQ ID NO: 4)
RRRWRKRRWWW.
```

19. The composition of claim 14, wherein the polypeptide is one of:

```
                                       (SEQ ID NO: 1)
RKFLRRRGEVAHFSQKSLGLYCWWW;

(SEQ ID NO: 2)
PIHRRIPPRWPRLKRRW;

(SEQ ID NO: 3)
LRRLKPLIRPWLRPLRRWWW;
or (SEQ ID NO: 4)
RRRWRKRRWWW.
```

* * * * *